United States Patent
Witters et al.

(10) Patent No.: US 11,486,001 B2
(45) Date of Patent: Nov. 1, 2022

(54) METHODS AND COMPOSITIONS FOR SEQUENCING COMPLEMENTARY POLYNUCLEOTIDES

(71) Applicant: Singular Genomics Systems, Inc., La Jolla, CA (US)

(72) Inventors: Daan Witters, San Diego, CA (US); Eli N. Glezer, Del Mar, CA (US); Allen Lipson, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 17/666,458

(22) Filed: Feb. 7, 2022

(65) Prior Publication Data

US 2022/0259648 A1    Aug. 18, 2022

Related U.S. Application Data

(60) Provisional application No. 63/183,585, filed on May 3, 2021, provisional application No. 63/163,638, filed on Mar. 19, 2021, provisional application No. 63/147,167, filed on Feb. 8, 2021.

(51) Int. Cl.
  *C12Q 1/6869* (2018.01)
  *C12Q 1/6834* (2018.01)

(52) U.S. Cl.
  CPC ......... *C12Q 1/6869* (2013.01); *C12Q 1/6834* (2013.01)

(58) Field of Classification Search
  CPC .......................... C12Q 1/6869; C12Q 1/6834
  See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,641,658 A | 6/1997 | Adams et al. |
| 5,763,594 A | 6/1998 | Hiatt et al. |
| 5,808,045 A | 9/1998 | Hiatt et al. |
| 5,872,244 A | 2/1999 | Hiatt et al. |
| 6,232,465 B1 | 5/2001 | Hiatt et al. |
| 7,057,026 B2 | 6/2006 | Barnes et al. |
| 7,115,400 B1 | 10/2006 | Adessi et al. |
| 7,435,572 B2 | 10/2008 | Bitinaite |
| 7,541,444 B2 | 6/2009 | Milton et al. |
| 7,790,418 B2 | 9/2010 | Mayer |
| 9,139,874 B2 | 9/2015 | Myers et al. |
| 9,334,531 B2 | 5/2016 | Li et al. |
| 9,371,557 B2 | 6/2016 | Li et al. |
| 10,738,072 B1 | 8/2020 | Graham et al. |
| 2003/0207290 A1 | 11/2003 | Kenten et al. |
| 2008/0009420 A1 | 1/2008 | Schroth et al. |
| 2009/0118128 A1 | 5/2009 | Liu et al. |
| 2012/0238738 A1 | 9/2012 | Hendrickson |
| 2014/0322759 A1 | 10/2014 | Skirgaila et al. |
| 2014/0329698 A1* | 11/2014 | Bignell ................ C12Q 1/6855 506/4 |
| 2014/0336057 A1 | 11/2014 | Rigatti et al. |
| 2016/0256846 A1 | 9/2016 | Smith et al. |
| 2017/0145500 A1 | 5/2017 | Myers et al. |
| 2018/0258472 A1 | 9/2018 | Glezer |
| 2018/0274024 A1 | 9/2018 | Ju et al. |
| 2020/0181692 A1* | 6/2020 | Oberstrass ........... C12Q 1/6848 |
| 2021/0189460 A1* | 6/2021 | Hosono ................ C12Q 1/6869 |

FOREIGN PATENT DOCUMENTS

| | | |
|---|---|---|
| WO | WO 1996/007669 A1 | 3/1996 |
| WO | WO 2004/018497 A2 | 3/2004 |
| WO | WO 2017/205336 | 11/2017 |

OTHER PUBLICATIONS

Bains, W. and Smith, GC. (Dec. 1, 1988) "A novel method for nucleic acid sequence determination." Journal of Theoretical Biology, 135.3:303-307.
Bentley, Dr. et al. (Nov. 6, 2008) "Accurate whole human genome sequencing using reversible terminator chemistry." Nature, 456. 7218: 53-59.
Berger, M. et al. (2000) "Universal bases for hybridization, replication and chain termination." Nucleic Acids Research, 28.15:2911-2914.
De Costa et al. (Mar. 2013) "Evaluating the Effect of Ionic Strength on Duplex Stability for PNA Having Negatively or Positively Charged Side Chains." PLoS One, 8.3:e58670.
Dohm, JC. et al. (Sep. 2008) "Substantial biases in ultra-short read data sets from high-throughput DNA sequencing." Nucleic Acids Research, 36.16:e105.
Drmanac, S. et al. (1998) "Accurate sequencing by hybridization for DNA diagnostics and individual genomics." Nature Biotechnology, 16.1:54-58.
Fodor, SPA. et al. (1991) "Light-Directed, Spatially Addressable Parallel Chemical Synthesis." Science, 251.4995:767-773.
Liang, F. et al. (2013) "Universal base analogues and their applications in DNA sequencing technology." Royal Society of Chemistry Advances, 3:14910-28.
Loakes, D. (2001) "The applications of universal DNA base analogues." Nucleic Acids Research, 29.12:2437-2447.
Rattray, AJ. and Strathern, JN. (2003) "Error-Prone DNA Polymerases: When Making a Mistake is the Only Way to Get Ahead." Annual Review of Genetics, 37:31-66.
Ronaghi, M. et al. (1998) "A Sequencing Method Based on Real-Time Pyrophosphate." Science, 281.5375:363-365.
Ronaghi, M. et al. (1996) "Real-Time DNA Sequencing Using Detection of Pyrophosphate Release." Analytical Biochemistry, 242.1:84-89.
Ronaghi, M. et al. (2001) "Pyrosequencing Sheds Light on DNA Sequencing." Genome Research, 11:3-11.
Shendure, J. et al. (2005) "Accurate Multiplex Polony Sequencing of an Evolved Bacterial Genome." Science, 309:1728-1732.

(Continued)

*Primary Examiner* — Cynthia B Wilder
(74) *Attorney, Agent, or Firm* — Mintz, Levin, Cohn, Ferris, Glovsky and Popeo, P.C.

(57) ABSTRACT

Disclosed herein, inter alia, are substrates, kits, and efficient methods of preparing and sequencing two or more regions of a double-stranded polynucleotide.

30 Claims, 32 Drawing Sheets

Specification includes a Sequence Listing.

(56) References Cited

OTHER PUBLICATIONS

International Search Report dated May 5, 2022, for PCT Application No. PCT/US2022/015527, filed Feb. 7, 2022, 4 pages.
Written Opinion dated May 5, 2022, for PCT Application No. PCT/US2022/015527, filed Feb. 7, 2022, 8 pages.

* cited by examiner

METHODS AND COMPOSITIONS FOR SEQUENCING COMPLEMENTARY POLYNUCLEOTIDES

CROSS-REFERENCES TO RELATED APPLICATIONS

This application claims the benefit of U.S. Provisional Application No. 63/147,167, filed Feb. 8, 2021; U.S. Provisional Application No. 63/163,638, filed Mar. 19, 2021; and U.S. Provisional Application No. 63/183,585, filed May 3, 2021; each of which are incorporated herein by reference in their entirety and for all purposes.

REFERENCE TO SEQUENCE LISTING SUBMITTED ELECTRONICALLY

The Sequence Listing titled 051385-542001US_SEQUENCE_LISTING_ST25.TXT, was created on Feb. 7, 2022 in machine format IBM-PC, MS-Windows operating system, is 17,892 bytes in size, and is hereby incorporated by reference in its entirety for all purposes.

BACKGROUND

Genetic analysis is taking on increasing importance in modem society as a diagnostic, prognostic, and as a forensic tool. DNA sequencing is a fundamental tool in biological and medical research; it is an essential technology for the paradigm of personalized precision medicine. Sanger sequencing, where the sequence of a nucleic acid is determined by selective incorporation and detection of dideoxynucleotides, enabled the mapping of the first human reference genome. While this methodology is still useful for validating newer sequencing technologies, efforts to sequence and assemble genomes using the Sanger method are an expensive and laborious undertaking, requiring specialized equipment and expertise. Next generation sequencing (NGS) methodologies make use of simultaneously sequencing millions of fragments of nucleic acids in a single run. However, traditional next generation sequencing still has shortcomings, such as challenges with detecting rare sequence variants in the context of polymerase errors.

BRIEF SUMMARY

In view of the foregoing, innovative approaches to address issues with existing sequencing technologies are needed. Disclosed herein are solutions to these and other problems in the art which, in embodiments, increase the fidelity and accuracy of high throughput sequencing methods. In certain embodiments, the compositions and methods provided herein reduce the amount of nucleic acid manipulation and duplication required by traditional NGS techniques. Prior to the present disclosure, cluster-based sequencing processes would include cleaving and removing one strand from double-stranded molecules in a cluster before generating a first read, without which the second strand would effectively compete with hybridization of the sequencing primer. Generating a sequencing read for the second (cleaved) strand would then require creating a new complementary strand from the sequenced first strand (i.e., a new second strand). In accordance with various embodiments, the methods disclosed herein permit obtaining sequence information (i.e., reading) from the original first and second strands (e.g., original strands from the initial cluster amplification, or amplicons), thereby reducing the time, reagents, expense, and risk of polymerase errors inherent in previous methods.

In an aspect is a substrate (e.g., a solid support) including a first polynucleotide attached to the substrate; a second polynucleotide attached to the substrate, wherein the second polynucleotide includes a complementary sequence to the first polynucleotide; and a third polynucleotide hybridized to the second polynucleotide. In embodiments, the third polynucleotide is not covalently attached to the substrate.

In an aspect is provided a method of sequencing a template polynucleotide. In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing one or more invasion primers to the second strand, and extending the one or more invasion primers; generating a first sequencing read by hybridizing one or more sequencing primers to the first strand, and extending the one or more first sequencing primers. In embodiments, the invasion primer is not covalently attached to the solid support.

In an aspect is provided a method of generating a template for nucleic acid sequencing reaction. In embodiments, the method includes providing a solid support including a plurality of immobilized oligonucleotide primers attached to the solid support via a linker, wherein the plurality of oligonucleotide primers include a plurality of forward primers and a plurality of reverse primers, amplifying a template nucleic acid by using the oligonucleotide primers attached to the solid support to generate a plurality of double-stranded amplification products, each double-stranded amplification product including a first strand hybridized to a second strand, wherein (i) each double-stranded amplification product includes the template polynucleotide or complement thereof, and (ii) the first strand and second strand are both attached to the solid support; and (iii) generating a first invasion strand hybridized to the second strand by hybridizing one or more invasion primers to the second strand, and extending the one or more invasion primers; thereby generating a template nucleic acid for a nucleic acid sequencing reaction. In embodiments, the method further includes hybridizing one or more sequencing primers to the first strand. In embodiments, the invasion primer is not covalently attached to the solid support.

In another aspect is provided a method including: amplifying a template nucleic acid by using a plurality of oligonucleotide primers attached to a solid support to generate a plurality of double-stranded amplification products, each double-stranded amplification product including a first strand hybridized to a second strand, wherein the first strand and second strand are both attached to the solid support; and generating a first invasion strand hybridized to the second strand by hybridizing one or more invasion primers to the second strand, and extending the one or more invasion primers to produce a single-stranded first strand. In embodiments, the invasion primer is not covalently attached to the solid support.

In an aspect is provided a method of sequencing a double-stranded polynucleotide including a first strand hybridized to a second strand, wherein the first strand and second strand are both attached to a solid support, the method including: i) hybridizing an invasion primer to the second strand and extending the invasion primer with a polymerase, thereby generating an invasion strand; ii) hybridizing a sequencing primer to the first strand; iii) incorporating one or more nucleotides into the sequencing primer with a polymerase to create an extension strand; and iv) detecting the one or more incorporated nucleotides so as to identify each incorporated nucleotide in the extension strand, thereby sequencing the first strand of the double-stranded polynucleotide.

In an aspect is provided a method of forming a plurality of single-stranded polynucleotides attached to a solid support, the method including: contacting a plurality of double-stranded polynucleotides including a first strand hybridized to a second strand with a plurality of invasion primers, wherein the first strand and the second strand are attached to the solid support; hybridizing one or more invasion primers to the second strand; and extending one or more invasion primers hybridized to the second strand with a polymerase to generate one or more invasion strands, displacing the first strand, thereby forming a plurality of single-stranded polynucleotides attached to the solid support.

In another aspect is provided a method of sequencing a template polynucleotide, the method including: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing an invasion primer to the second strand, and extending the invasion primer, wherein the invasion primer is not covalently attached to the solid support; and generating a first sequencing read by hybridizing one or more sequencing primers to the first strand, and extending the one or more first sequencing primers.

BRIEF DESCRIPTION OF THE DRAWINGS

FIG. 1A illustrates two dsDNA duplex strands, each duplex having a first strand hybridized to a second strand, and each strand is attached to the solid support. By way of simplification, only one duplex is shown, however it is understood that a plurality of duplexes (double-stranded amplification products) are present on the solid support, typically in a plurality of localized monoclonal clusters. An invasion oligonucleotide (also referred to herein as an invasion primer or invasion oligo) anneals at the 3' end of one of the strands. After extension of the invasion oligonucleotide has been completed, one strand of the initial dsDNA molecule is now single-stranded and available for a first sequencing read, as shown in FIG. 1B. Also illustrated in FIG. 1B, the sequenced strand may optionally be cleaved at a cleavable site (represented as 'X') and removed, thus leaving the complementary strand available for sequencing. For clarity in the figure, a single X is depicted, however it is understood that the cleavable site may include multiple chemical, enzymatic, or photochemical entities capable of being cleaved.

FIG. 2A shows the fluorescent images for each of the four conditions, as well as a cartoon illustration of the duplex and fluorescently labeled probe under each respective image. FIG. 2B shows the median fluorescent signal and number of identified features for each condition. Condition 4 is a positive control whereby the clusters were converted into ssDNA by cleaving and removing one of the strands from the flow cell surface, followed by labeling the resulting ssDNA molecules with a complementary FAM-labeled DNA probe. Condition 3 is a negative control whereby the amplicon clusters are not subjected to an invasion primer nor extension conditions. Condition 2 reveals that an invasion primer is capable of invading the double-stranded amplification product, but without extension of the invasion primer, the amplicons are not completely accessible to FAM-labeled probes. Condition 1 shows dsDNA clusters that were not cleaved, but were subjected to the methods described herein, such as strand invasion and extension, followed by hybridization of a complementary FAM-labeled DNA probe to the liberated ssDNA strand. The probe is only able to hybridize if a complementary single-stranded region is available. Following probe excitation and image acquisition, Condition 1 and condition 4 show the presence of punctate clusters indicative of successful ssDNA formation using the methods described herein.

FIG. 8A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U' in FIGS. 8A-8C, the cleavable site may be a deoxyuracil (dU) towards the 3' end of the invasion oligo. After runoff extension of the invasion oligonucleotide has been completed, one strand of the initial dsDNA molecule is now single-stranded and available for a first sequencing read, as shown in FIG. 8B. This renders one of the two strands of the original dsDNA amplicon available for hybridization of a sequencing primer to initiate the SBS process. The sequenced strand may further optionally be cleaved at a cleavable site (represented as 'X') and removed, thus leaving the complementary strand available for sequencing, as illustrated in FIG. 8B. Subsequently, the 3' end of the invasion primer may be cleaved at a cleavable site (e.g., nicking the dU using suitable conditions), leaving behind a 5'-phosphate in the invasion strand that can subsequently be degraded with a 5' to 3' exonuclease, allowing for the invasion primer to serve as a sequencing primer for the second strand, as illustrated in FIGS. 8C-8D.

FIG. 9A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U', the cleavable site may be a deoxyuracil (dU) towards the 3' end of the invasion oligo. After runoff extension (i.e., extension to a sufficient length) of the invasion oligonucleotide has been completed, one strand of the initial dsDNA molecule is now single-stranded and available for a first sequencing read, as shown in FIG. 9B. This renders one of the two strands of the original dsDNA amplicon available for hybridization of a sequencing primer to initiate the SBS process. The sequenced strand may further be extended with native dNTPs to complete the extension of the sequenced strand, as illustrated in FIG. 9B as the solid line beyond the star. Further extending the sequencing primer with unmodified nucleotides eliminates any remaining single-stranded region. Subsequently, the 3' end of the invasion primer may be cleaved at a cleavable site (e.g., cleaving the dU using a uracil DNA glycosylase or formamidopyrimidine DNA glycosylase (Fpg) as described herein), leaving behind a 5'-phosphate in the extended part of the invasion primer that can subsequently be degraded with a 5' to 3' exonuclease, allowing for the invasion primer to serve as a sequencing primer for the second strand, as illustrated in FIGS. 9C-9D.

FIG. 10A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U', the cleavable site may be a deoxyuracil (dU) towards the 3' end of the invasion oligo. Following runoff extension of the invasion oligonucleotide, one strand of the initial dsDNA molecule is now single-stranded and available for a first sequencing read, as shown in FIG. 10B. This renders one of the two strands of the original dsDNA amplicon available for hybridization of a sequencing primer to initiate the SBS process. The sequenced strand may further be extended with one or more dideoxynucleotide triphosphates (ddNTPs) to prevent further extension, as illustrated in FIG. 10B as the hexagon. Further extending the sequencing primer with ddNTPs eliminates any prevents any further extension. Subsequently, the cleavable site at the 3' end of the invasion primer may be cleaved (e.g., the dU), leaving behind a 5'-phosphate in the extended part of the invasion primer that can subsequently be degraded with a 5' to 3' exonuclease, allowing for the invasion primer to serve as a sequencing primer for the second strand, as illustrated in FIGS. 10C-10D.

FIG. 11A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U', the cleavable site may be a deoxyuracil (dU) towards the 3' end of the invasion oligo. Runoff extension of the invasion oligonucleotide is then performed with dUTP, dATP, dGTP, and dCTP, leaving one strand of the initial dsDNA molecule single-stranded and available for a first sequencing read, as shown in FIG. 11B. The sequenced strand may optionally further be cleaved at a cleavable site (represented as 'X') and removed, thus leaving the complementary strand available for sequencing, as illustrated in FIG. 11B. Subsequently, the invasion strand may be nicked at internal scissile sites (e.g., resulting from amplification with the dUTP), leaving behind small, low Tm fragments that may be denatured and removed under suitable conditions, as shown in FIG. 11C. Additionally, this cleavage and denaturation step exposes the 3' end of the invasion oligo, allowing for the invasion primer to serve as a sequencing primer for the second strand, as illustrated in FIGS. 11C-11D.

FIG. 12A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U', the cleavable site may be a deoxyuracil (dU) towards the 3' end of the invasion oligo. Runoff extension of the invasion oligonucleotide is then performed with dUTP, dATP, dGTP, and dCTP, leaving one strand of the initial dsDNA molecule single-stranded and available for a first sequencing read, as shown in FIG. 12B. Once the first sequencing read has been obtained, the 3' end of the first sequencing read is capped by ddNTP incorporation. A second sequencing read is then obtained by annealing and extending a second sequencing primer 3' of the terminated first sequencing read. Subsequently, a ddNTP is incorporated into the 3' end of the second sequencing read, and thereafter the invasion strand may be nicked at internal scissile sites (e.g., resulting from amplification with the dUTP), leaving behind small fragments with exposed 5' ends that may be removed under suitable conditions, for example, by lambda exonuclease digestion, as shown in FIGS. 12C-12D. This cleavage and removal step exposes the 3' end of the second strand, making it available for a third sequencing read, as shown in FIG. 12E. Once the third sequencing read has been obtained, the 3' end of the third sequencing read is capped by ddNTP incorporation. A fourth sequencing read is then obtained by annealing and extending a fourth sequencing primer 3' of the terminated third sequencing read, as illustrated in FIG. 12E.

DETAILED DESCRIPTION

Figure 1A:
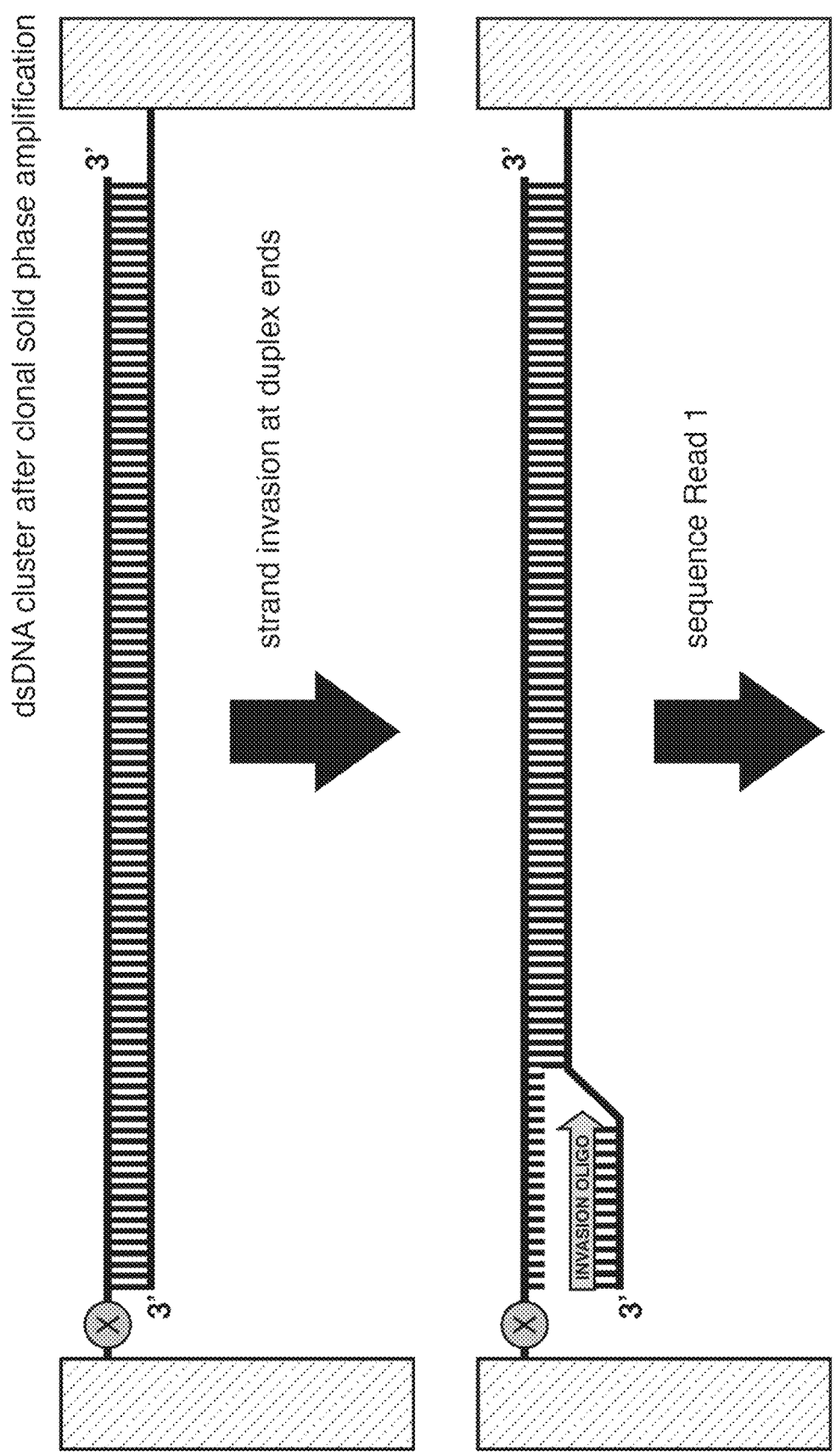
FIGS. 1A-1B illustrate an embodiment of paired-strand sequencing by strand invasion of an invasion primer at the 3' end of a first strand of a duplex, followed by runoff extension of the invasion primer by a strand-displacing polymerase. The hashed boxes on each end represent a polymer scaffold that is anchored to a solid support, such as glass or silicon support.
Figure 1B:
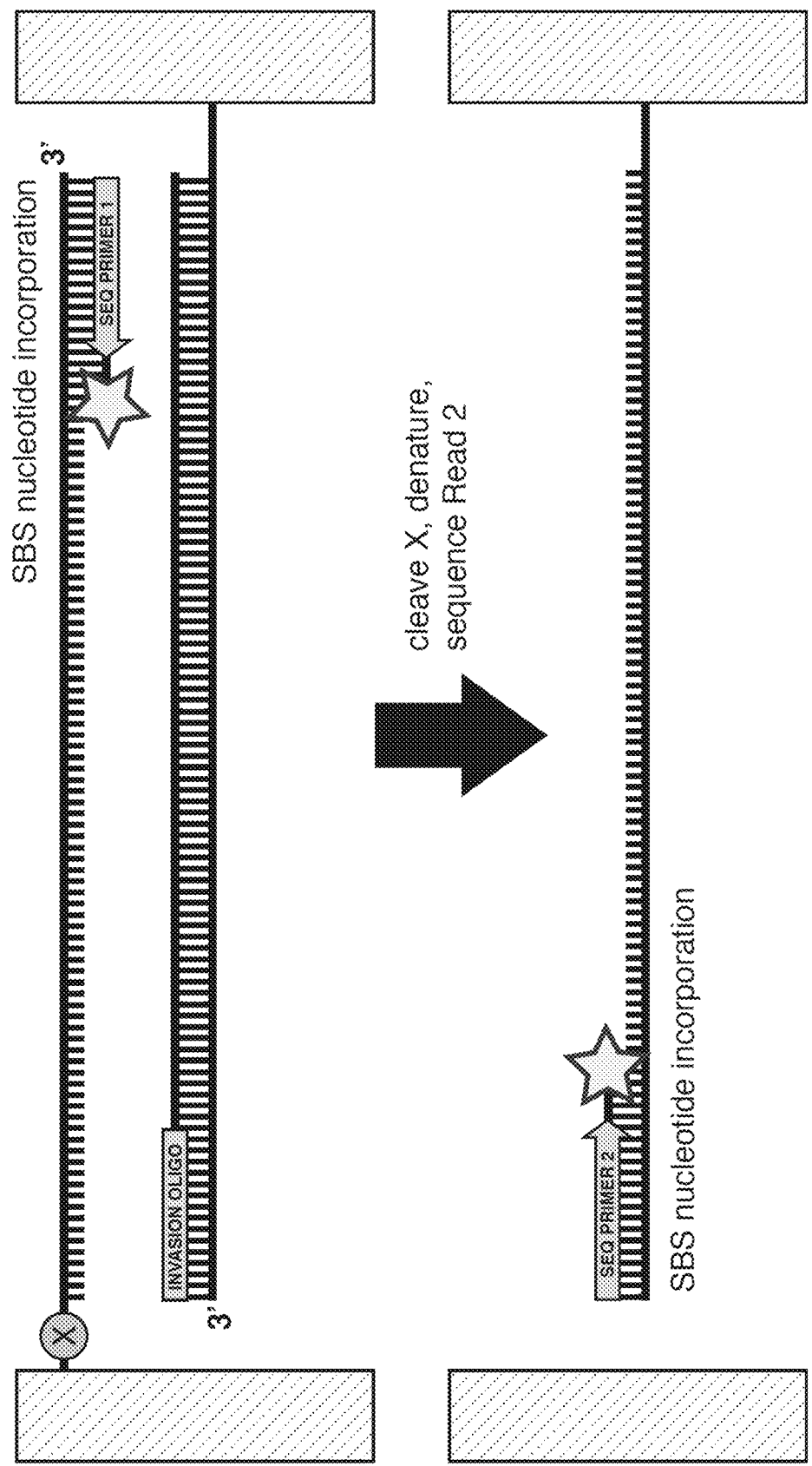

The aspects and embodiments described herein relate to sequencing a polynucleotide. In embodiments, as described herein, the methods relate to sequencing a first strand of a double-stranded polynucleotide, and optionally sequencing the complement of first strand (i.e., the second strand) of the same double-stranded polynucleotide. The terms "cluster" and "colony" are used interchangeably throughout this application and refer to a discrete site on a solid support comprised of a plurality of immobilized nucleic acid strands. The term "clustered array" refers to an array formed from such clusters or colonies.

I. Definitions

All patents, patent applications, articles and publications mentioned herein, both supra and infra, are hereby expressly incorporated herein by reference in their entireties. The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "associated" or "associated with" can mean that two or more species are identifiable as being co-located at a point in time. An association can mean that two or more species are or were within a similar container.

An association can be an informatics association, where for example digital information regarding two or more species is stored and can be used to determine that one or more of the species were co-located at a point in time. An association can also be a physical association.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. When referring to a double-stranded polynucleotide including a first strand hybridized to a second strand, it is to be understood that each of the terms "first strand" and "second strand" refer to single-stranded polynucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed. Complementary single stranded nucleic acids and/or substantially complementary single stranded nucleic acids can hybridize to each other under hybridization conditions, thereby forming a nucleic acid that is partially or fully double stranded. When referring to a double-stranded polynucleotide including a first strand hybridized to a second strand, it is understood that each of the first strand and the second strand are independently single-stranded polynucleotides. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. In some embodiments, an oligonucleotide may be immobilized to a solid support.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support (e.g., a polymer coated solid support). In embodiments, forward primers anneal to the antisense strand of the double-stranded DNA, which runs from the 3' to 5' direction. Forward primers, for example, initiate the synthesis of a gene in the 5' to 3' direction. In embodiments, reverse primers anneal to the sense strand of the double-stranded DNA, which runs from the 5' to 3' direction. Reverse primers, for example, initiate the synthesis of a gene in the 3' to 5' direction. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the terms "invasion primer", "invasion oligonucleotide" and "third polynucleotide" refer to a polynucleotide molecule that may hybridize to a single-stranded nucleic acid sequence of a double-stranded polynucleotide and be extended in a template-directed process (e.g., extended with a polymerase) for nucleic acid synthesis. In embodiments, an invasion primer hybridizes at or near the end of the single-stranded nucleic acid sequence (e.g., the 5' end or the 3' end), or the invasion primer hybridizes at an internal sequence. Extension of an invasion primer results in the formation of an "invasion strand" complementary to either the first strand or the second strand of the double-stranded polynucleotide. This renders one of the two strands of the original dsDNA amplicon available for hybridization of a sequencing primer to initiate the sequencing process. In embodiments, the invasion primer includes locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, or combinations thereof. In embodiments, the invasion primer includes phosphorothioate nucleic acids. In embodiments, the invasion primer includes one or more locked nucleic acids (LNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids. In embodiments, the invasion primer includes 10 to 15 locked nucleic acids (LNAs). In embodiments, the invasion primer includes a sequence described herein, for example within Table 1. In embodiments, the invasion primer includes one or more phosphorothioates at the 5' end. In embodiments, the invasion primer includes one or more LNAs at the 5' end. In embodiments, the invasion primer includes two or more consecutive LNAs at the 3' end. In embodiments, the invasion primer includes two or more consecutive LNAs at the 5' end. In embodiments, the invasion primer includes a plurality (e.g., 2 to 10) of synthetic nucleotides (e.g., LNAs) and a plurality (e.g., 2 to 10) canonical or native nucleotides (e.g., dNTPs). In embodiments, the invasion primer includes one or more (e.g., 2 to 5) deoxyuracil nucleobases (dU). In embodiments, the one or more dU nucleobases are at or near the 3' end of the invasion primer (e.g., within 5 nucleotides of the 3' end). In embodiments, the one or more dU nucleobases are distributed through the invasion primer. In embodiments, the invasion primer includes from 5' to 3' a plurality (e.g., 2 to 5) of phosphorothioate nucleic acids, followed by a plurality of synthetic nucleotides (e.g., LNAs), and a plurality (e.g., 2 to 10) of canonical bases. In some embodiments, the invasion primer includes a plurality of canonical bases, wherein the canonical bases terminate (i.e., at the 3' end) with a deoxyuracil nucleobase (dU). In embodiments, the invasion primer is about 10 to 100 nucleotides in length. In embodiments, the invasion primer is about 15 to about 40 nucleotides in length. In embodiments, the calculated or predicted melting temperature (Tm) of the invasion primer is about 70° C. to about 95° C. In embodiments, the calculated or predicted melting temperature (Tm) of the invasion primer is about 75° C. to about 85° C. In embodiments, the calculated or predicted melting temperature (Tm) of the invasion primer is 75° C. to 85° C.

As used herein, the terms "solid support" and "substrate" and "solid surface" are used interchangeably and refers to discrete solid or semi-solid surfaces to which a plurality of nucleic acid (e.g., primers) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports may be in the form of discrete particles, which alone does not imply or require any particular shape. The term "particle" means a small body made of a rigid or semi-rigid material. The body can have a shape characterized, for example, as a sphere, oval, microsphere, or other recognized particle shape whether having regular or irregular dimensions. As used herein, the term "discrete particles" refers to physically distinct particles having discernible boundaries. The term "particle" does not indicate any particular shape. The shapes and sizes of a collection of particles may be different or about the same (e.g., within a desired range of dimensions, or having a desired average or minimum dimension). A particle may be substantially spherical (e.g., microspheres) or have a non-spherical or irregular shape, such as cubic, cuboid, pyramidal, cylindrical, conical, oblong, or disc-shaped, and the like. In embodiments, the particle has the shape of a sphere, cylinder, spherocylinder, or ellipsoid. Discrete particles collected in a container and contacting one another will define a bulk volume containing the particles, and will typically leave some internal fraction of that bulk volume unoccupied by the particles, even when packed closely together. In embodiments, cores and/or core-shell particles are approximately spherical. As used herein the term "spherical" refers to structures which appear substantially or generally of spherical shape to the human eye, and does not require a sphere to a mathematical standard. In other words, "spherical" cores or particles are generally spheroidal in the sense of resembling or approximating to a sphere. In embodiments, the diameter of a spherical core or particle is substantially uniform, e.g., about the same at any point, but may contain imperfections, such as deviations of up to 1, 2, 3, 4, 5 or up to 10%. Because cores or particles may deviate from a perfect sphere, the term "diameter" refers to the longest dimension of a given core or particle. Likewise, polymer shells are not necessarily of perfect uniform thickness all around a given core. Thus, the term "thickness" in relation to a polymer structure (e.g., a shell polymer of a core-shell particle) refers to the average thickness of the polymer layer.

A solid support may further comprise a polymer or hydrogel on the surface to which the primers are attached (e.g., the primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip, surface of a particle), for example a metal surface (e.g., steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, silica, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material).

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer. Polymers can be hydrophilic, hydrophobic, or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

The term "surface" is intended to mean an external part or external layer of a substrate. The surface can be in contact with another material such as a gas, liquid, gel, polymer, organic polymer, second surface of a similar or different material, metal, or coating. The surface, or regions thereof, can be substantially flat. The substrate and/or the surface can have surface features such as wells, pits, channels, ridges, raised regions, pegs, posts or the like.

As used herein, the terms "cluster" and "colony" are used interchangeably to refer to a discrete site on a solid support that includes a plurality of immobilized polynucleotides and a plurality of immobilized complementary polynucleotides. The term "clustered array" refers to an array formed from such clusters or colonies. In this context the term "array" is not to be understood as requiring an ordered arrangement of clusters. The term "array" is used in accordance with its ordinary meaning in the art, and refers to a population of different molecules that are attached to one or more solid-phase substrates such that the different molecules can be differentiated from each other according to their relative location. An array can include different molecules that are each located at different addressable features on a solid-phase substrate. The molecules of the array can be nucleic acid primers, nucleic acid probes, nucleic acid templates or nucleic acid enzymes such as polymerases or ligases. Arrays useful in the invention can have densities that ranges from about 2 different features to many millions, billions or higher. The density of an array can be from 2 to as many as a billion or more different features per square cm. For example an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher. In embodiments, the arrays have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

As used herein, the term "template polynucleotide" or "template nucleic acid" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The terms "single strand" and "ssDNA" are used in accordance with its plain and ordinary meaning and refer to a single-stranded polynucleotide. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

In embodiments, a target polynucleotide is a cell-free polynucleotide. In general, the terms "cell-free," "circulating," and "extracellular" as applied to polynucleotides (e.g. "cell-free DNA" (cfDNA) and "cell-free RNA" (cfRNA)) are used interchangeably to refer to polynucleotides present in a sample from a subject or portion thereof that can be isolated or otherwise manipulated without applying a lysis step to the sample as originally collected (e.g., as in extraction from cells or viruses). Cell-free polynucleotides are thus unencapsulated or "free" from the cells or viruses from which they originate, even before a sample of the subject is collected. Cell-free polynucleotides may be produced as a byproduct of cell death (e.g. apoptosis or necrosis) or cell shedding, releasing polynucleotides into surrounding body fluids or into circulation. Accordingly, cell-free polynucleotides may be isolated from a non-cellular fraction of blood (e.g. serum or plasma), from other bodily fluids (e.g. urine), or from non-cellular fractions of other types of samples.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as may characterize a nucleotide analog (e.g., a reversible terminating moiety). Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate). A "canonical" nucleotide is an unmodified nucleotide.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

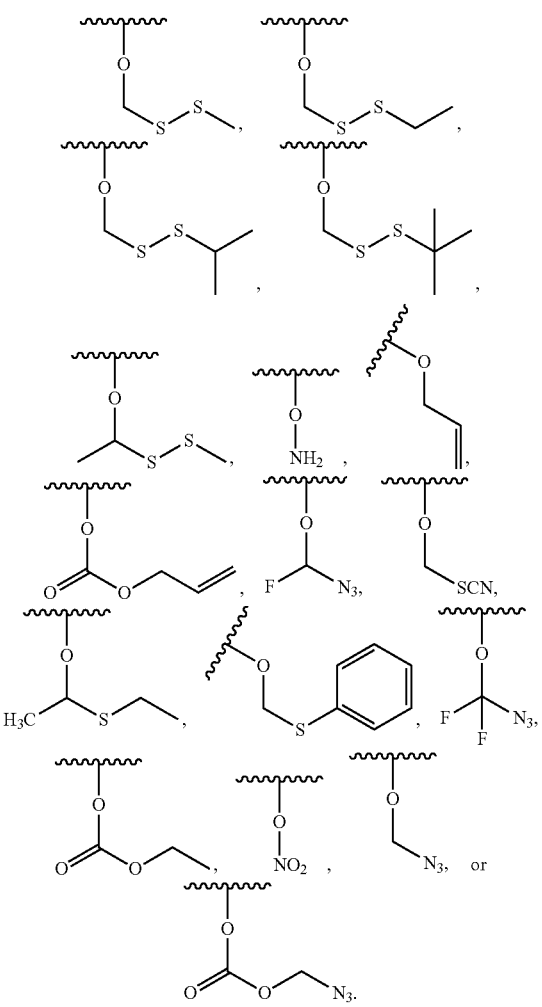

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include a modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site blast.ncbi.nlm.nih.gov/Blast.cgi or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue. In general, the conditions under which a removable group is removed are compatible with a process employing the removable group (e.g., an amplification process or sequencing process).

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3-O-blocked reversible terminators, the blocking group —OR [reversible terminating (capping)

group] is linked to the oxygen atom of the 3-OH of the pentose, while the label is linked to the base, which acts as a reporter and can be cleaved. The 3-O-blocked reversible terminators are known in the art, and may be, for instance, a 3'-ONH$_2$ reversible terminator, a 3'-O-allyl reversible terminator, or a 3-O-azidomethyl reversible terminator. In embodiments, the reversible terminator moiety is

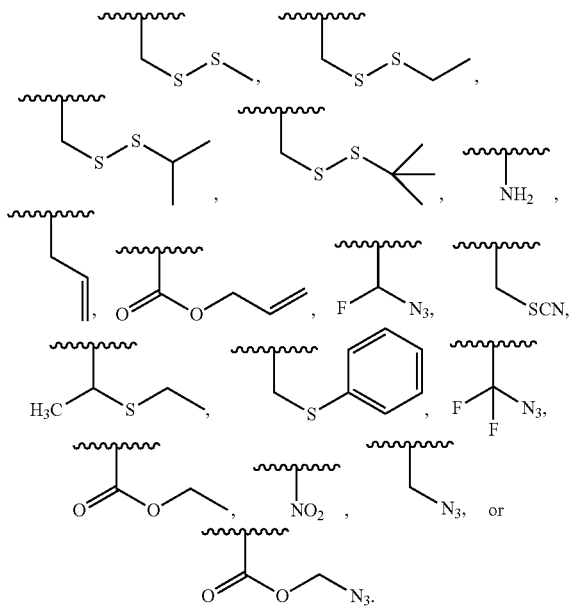

The term "allyl" as described herein refers to an unsubstituted methylene attached to a vinyl group (i.e., —CH═CH$_2$), having the formula

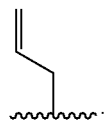

In embodiments, the reversible terminator moiety is

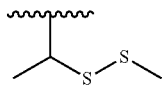

as described in U.S. Pat. No. 10,738,072, which is incorporated herein by reference for all purposes. For example, a nucleotide including a reversible terminator moiety may be represented by the formula:

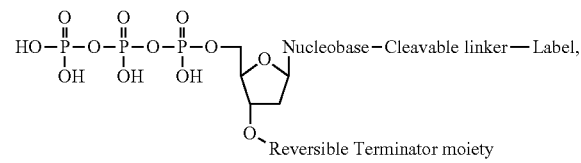

where the nucleobase is adenine or adenine analogue, thymine or thymine analogue, guanine or guanine analogue, or cytosine or cytosine analogue.

In some embodiments, a nucleic acid comprises a molecular identifier or a molecular barcode. As used herein, the term "molecular barcode" (which may be referred to as a "tag", a "barcode", a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads comprising the barcode can be identified as originating from a single sample polynucleotide molecule on the basis of the barcode alone. In other embodiments, individual barcode sequences may be used more than once, but adapters comprising the duplicate barcodes are associated with different sequences and/or in different combinations of barcoded adapters, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random.

In some embodiments, the reaction conditions for a plurality of invasion-primer extension cycles includes incubation in a denaturant. As used herein, the terms "denaturant" or plural "denaturants" are used in accordance with their plain and ordinary meanings and refer to an additive or condition that disrupts the base pairing between nucleotides within opposing strands of a double-stranded polynucleotide molecule. The term "denature" and its variants, when used in reference to any double-stranded polynucleotide molecule, or double-stranded polynucleotide sequence, includes any process whereby the base pairing between nucleotides within opposing strands of the double-stranded molecule, or double-stranded sequence, is disrupted. Typically, denaturation includes rendering at least some portion or region of two strands of the double-stranded polynucleotide molecule or sequence single-stranded or partially single-stranded. In some embodiments, denaturation includes separation of at least some portion or region of two strands of the double-stranded polynucleotide molecule or sequence from each other. Typically, the denatured region or portion is then capable of hybridizing to another polynucleotide molecule or sequence. Optionally, there can be "complete" or "total" denaturation of a double-stranded polynucleotide molecule or sequence. Complete denaturation conditions are, for example, conditions that would result in complete separation of a significant fraction (e.g., more than 10%, 20%, 30%, 40% or 50%) of a large plurality of strands from their extended and/or full-length complements. Typically, complete or total denaturation disrupts all of the base pairing between the nucleotides of the two strands with each other. Similarly, a nucleic acid sample is optionally considered fully denatured when more than 80% or 90% of individual molecules of the sample lack any double-strandedness (or lack any hybridization to a complementary strand).

Alternatively, the double-stranded polynucleotide molecule or sequence can be partially or incompletely denatured. A given nucleic acid molecule can be considered partially denatured when a portion of at least one strand of the nucleic acid remains hybridized to a complementary strand, while another portion is in an unhybridized state (even if it is in the presence of a complementary sequence). The unhybridized portion is optionally at least 5, 10, 15, 20, 50, or more nucleotides in length. The hybridized portion is optionally at least 5, 10, 15, 20, 50, or more nucleotides in length. Partial denaturation includes situations where some, but not all, of the nucleotides of one strand or sequence, are based paired with some nucleotides of the other strand or sequence within a double-stranded polynucleotide. In some embodiments, at least 20% but less than 100% of the nucleotide residues of one strand of the partially denatured polynucleotide (or sequence) are not base paired to nucleotide residues within the opposing strand. In embodiments, at least 50% of nucleotide residues within the double-stranded polynucleotide molecule (or double-stranded polynucleotide sequence) are in single-stranded (or unhybridized) from, but less than 20% or 10% of the residues are double-stranded.

Optionally, a nucleic acid sample can be considered to be partially denatured when a substantial fraction of individual nucleic acid molecules of the sample (e.g., above 20%, 30%, 50%, or 70%) are in a partially denatured state. Optionally less than a substantial amount of individual nucleic acid molecules in the sample are fully denatured, e.g., not more than 5%, 10%, 20%, 30% or 50% of the nucleic acid molecules in the sample. Under exemplary conditions at least 50% of the nucleic acid molecules of the sample are partly denatured, but less than 20% or 10% are fully denatured. In other situations, at least 30% of the nucleic acid molecules of the sample are partly denatured, but less than 10% or 5% are fully denatured. Similarly, a nucleic acid sample can be non-denatured when a minority of individual nucleic acid molecules in the sample are partially or completely denatured.

In an embodiment, partially denaturing conditions are achieved by maintaining the duplexes as a suitable temperature range. For example, the nucleic acid is maintained at temperature sufficiently elevated to achieve some heat-denaturation (e.g., above 45° C., 50° C., 55° C., 60° C., 65° C., or 70° C.) but not high enough to achieve complete heat-denaturation (e.g., below 95° C. or 90° C. or 85° C. or 80° C. or 75° C.). In an embodiment the nucleic acid is partially denatured using substantially isothermal conditions. Alternatively, chemical denaturation can be accomplished by contacting the double-stranded polynucleotide to be denatured with appropriate chemical denaturants, such as strong alkalis, strong acids, chaotropic agents, and the like and can include, for example, NaOH, urea, or guanidine-containing compounds. In some embodiments, partial or complete denaturation is achieved by exposure to chemical denaturants such as urea or formamide, with concentrations suitably adjusted, or using high or low pH (e.g., pH between 4-6 or 8-9). In embodiments, the denaturant is a buffered solution including betaine, dimethyl sulfoxide (DMSO), ethylene glycol, formamide, glycerol, guanidine thiocyanate, 4-methylmorpholine 4-oxide (NMO), or a mixture thereof. In embodiments, the first denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In an embodiment herein, partial denaturation and/or amplification, including any one or more steps or methods described herein, can be achieved using a recombinase and/or single-stranded binding protein.

In some embodiments, complete or partial denaturation of a double-stranded polynucleotide sequence is accomplished by contacting the double-stranded polynucleotide sequence using appropriate denaturing agents. For example, the double-stranded polynucleotide can be subjected to heat-denaturation (also referred to interchangeably as thermal denaturation) by raising the temperature to a point where the desired level of denaturation is accomplished. In some embodiments, thermal denaturation of a double-stranded polynucleotide, includes adjusting the temperature to achieve complete separation of the two strands of the polynucleotide, such that 90% or greater of the strands are in single-stranded form across their entire length. A completely denatured double-stranded polynucleotide results in a separated first strand and a second strand, each of which is a single-stranded polynucleotide. In some embodiments, complete thermal denaturation of a polynucleotide molecule (or polynucleotide sequence) is accomplished by exposing the polynucleotide molecule (or sequence) to a temperature that is at least 5° C., 10° C., 15° C., 20° C., 25° C., 30° C., 50° C., or 100° C., above the calculated or predict melting temperature (Tm) of the polynucleotide molecule or sequence.

In some embodiments, complete or partial denaturation is accomplished by treating the double-stranded polynucleotide sequence to be denatured using a denaturant mixture including an SSB protein (e.g., T4 gp32 protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB)), a strand-displacing polymerase (e.g., Bst large fragment (Bst LF) polymerase, Bst 3.0 polymerase, Bst 2.0 polymerase, Bsu polymerase, SD polymerase, Vent exo-polymerase, Phi29 polymerase, or a mutant thereof), and one or more crowding agents (poly(ethylene glycol) (PEG), polyvinylpyrrolidone (PVP), bovine serum albumin (BSA), dextran, Ficoll (e.g., Ficoll 70 or Ficoll 400), glycerol, or a combination thereof). In embodiments, the crowding agent is poly(ethylene glycol) (e.g., PEG 200, PEG 600, PEG 800, PEG 2,050, PEG 4,600, PEG 6,000, PEG 8,000, PEG 10,000, PEG 20,000, or PEG 35,000), dextran sulfate, bovine pancreatic trypsin inhibitor (BPTI), ribonuclease A, lysozyme, β-lactoglobulin, hemoglobin, bovine serum albumin (BSA), or poly(sodium 4-styrene sulfonate) (PSS). In embodiments, the denaturant mixture including an SSB, a strand-displacing polymerase, and one or more crowding agents does not include a chemical denaturant (e.g., betaine, DMSO, ethylene glycol, formamide, guanidine thiocyanate, NMO, TMAC, or a mixture thereof).

In some embodiments, a nucleic acid comprises a label. As used herein, the term "label" or "labels" are used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

In embodiments, the detectable label is a fluorescent dye. In embodiments, the detectable label is a fluorescent dye capable of exchanging energy with another fluorescent dye (e.g., fluorescence resonance energy transfer (FRET) chromophores). Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a detectable moiety containing two nitrogen groups separated by a polymethine chain. In embodiments, the cyanine moiety has 3 methine structures (i.e., cyanine 3 or Cy3). In embodiments, the cyanine moiety has 5 methine structures (i.e., cyanine 5 or Cy5). In embodiments, the cyanine moiety has 7 methine structures (i.e., cyanine 7 or Cy7).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Terminator γ, 9° N polymerase (exo-), Terminator II, Terminator III, or Terminator IX). In embodiments, the DNA polymerase is a modified archaeal DNA polymerase. In embodiments, the polymerase is a reverse transcriptase. In embodiments, the polymerase is a mutant $P.$ $abyssi$ polymerase (e.g., such as a mutant $P.$ $abyssi$ polymerase described in WO 2018/148723 or WO 2020/056044). In embodiments, the polymerase is an enzyme described in US 2021/0139884. For example, a polymerase catalyzes the addition of a next correct nucleotide to the 3'-OH group of the primer via a phosphodiester bond, thereby chemically incorporating the nucleotide into the primer. Optionally, the polymerase used in the provided methods is a processive polymerase. Optionally, the polymerase used in the provided methods is a distributive polymerase.

As used herein, the term "thermophilic nucleic acid polymerase" refers to a family of DNA polymerases (e.g., 9° Nm) and mutants thereof derived from the DNA polymerase originally isolated from the hyperthermophilic archaea, $Thermococcus$ sp. 9 degrees N-7, found in hydrothermal vents at that latitude (East Pacific Rise) (Southworth M W, et al. PNAS. 1996; 93(11):5281-5285). A thermophilic nucleic acid polymerase is a member of the family B DNA polymerases. Site-directed mutagenesis of the 3'-5' exo motif I (Asp-Ile-Glu or DIE) to ALA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Terminator II enzyme from New England Biolabs with D141A/E143A/Y409V/A485L mutations); 3'-amino-dNTPs, 3'-azido-dNTPs and other 3'-modified nucleotides (e.g., NEB Terminator III DNA Polymerase with D141A/E143A/L408S/Y409A/P410V mutations, NEB Terminator IX DNA polymerase), or γ-phosphate labeled nucleotides (e.g., Terminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. PNAS. 1996; 93(11):5281-5285; Bergen K, et al. ChemBioChem. 2013; 14(9):1058-1062; Kumar S, et al. Scientific Reports. 2012; 2:684; Fuller C W, et al. 2016; 113(19):5233-5238; Guo J, et al. Proceedings of the National Academy of Sciences of the United States of America. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996). In embodiments, 5'-3' exonuclease activity refers to the successive removal of nucleotides in double-stranded DNA in a 5'→3' direction. In embodiments, the 5'-3' exonuclease is lambda exonuclease. For example, lambda exonuclease catalyzes the removal of 5' mononucleotides from duplex DNA, with a preference for 5' phosphorylated double-stranded DNA. In other embodiments, the 5'-3' exonuclease is E. coli DNA Polymerase I.

As used herein, the term "incorporating" or "chemically incorporating," when used in reference to a primer and a nucleotide, refers to the process of joining the nucleotide to the primer or extension product thereof by formation of a phosphodiester bond.

As used herein, the term "selective" or "selectivity" or the like of a compound refers to the compound's ability to discriminate between molecular targets. When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the agent's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

As used herein, the terms "sequencing", "sequence determination", "determining a nucleotide sequence", and the like include determination of a partial or complete sequence information, including the identification, ordering, or locations of the nucleotides that comprise the polynucleotide being sequenced, and inclusive of the physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting the one or more nucleotides incorporated. In embodiments, one nucleotide (e.g., a modified nucleotide) is incorporated per sequencing cycle. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. An "extension strand" is formed as the one or more nucleotides are incorporated into a complementary polynucleotide hybridized to a template nucleic acid. The extension strand is complementary to the template nucleic acid. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes, and other substances can be removed between steps by washing. Cycles may include repeating these steps, and the sequence of each cluster is read over the multiple repetitions.

As used herein, the term "sequencing reaction mixture" is used in accordance with its plain and ordinary meaning and refers to an aqueous mixture that contains the reagents necessary to allow a nucleotide or nucleotide analogue to be added (i.e., incorporated) to a DNA strand by a DNA polymerase. As used herein, the term "invasion-reaction mixture" is used in accordance with its plain and ordinary meaning and refers to an aqueous mixture that contains the reagents necessary to allow a nucleotide or nucleotide analogue to be added to a DNA strand by a DNA polymerase that extends the invasion primer.

As used herein, the term "extension" or "elongation" is used in accordance with their plain and ordinary meanings and refer to synthesis by a polymerase of a new polynucleotide strand (i.e., an "extension strand") complementary to a template strand by adding free nucleotides (e.g., dNTPs) from a reaction mixture that are complementary to the template in a 5'-to-3' direction, including condensing a 5'-phosphate group of a dNTPs with a 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label. The sequence reads are optionally stored in an appropriate data structure for further evaluation. In embodiments, a first sequencing reaction can generate a first sequencing read. The first sequencing read can provide the sequence of a first region of the polynucleotide fragment. In embodiments, a second sequencing primer can initiate sequencing at a second location on the nucleic acid template. The second location can be distinct from the first location. In some cases, a 3' terminal nucleotide of the second primer can hybridize to a location that is more than 5 nucleotides away from a binding site of a 3' terminal nucleotide of the first primer. The second sequencing reaction can generate a second sequencing read. The second sequencing read can provide the sequence of a second region of the nucleic acid template which is distinct from the first region of the nucleic acid template. In some embodiments, the nucleic acid template is optionally subjected to one or more additional rounds of sequencing using additional sequencing primers, thereby generating additional sequencing reads.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution. Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands (e.g., two single-stranded polynucleotides) that are hybridized to each other can form a duplex which comprises a double-stranded portion of nucleic acid.

A nucleic acid can be amplified by a suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5′ portion that does not hybridize to the template), or one or more mismatched bases within a hybridizing portion of the primer).

A nucleic acid can be amplified by a thermocycling method or by an isothermal amplification method. In some embodiments, a rolling circle amplification method is used. In some embodiments, amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution-based primers can be used. Non-limiting examples of solid phase nucleic acid amplification reactions include interfacial amplification, bridge amplification, emulsion PCR, WildFire amplification (e.g., US patent publication US20130012399), the like or combinations thereof.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide, -maleimide,

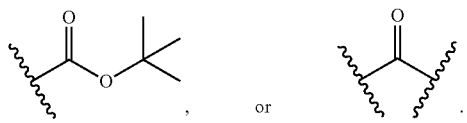

In embodiments, the bioconjugate reactive group may be protected (e.g., with a protecting group). In embodiments, the bioconjugate reactive moiety is

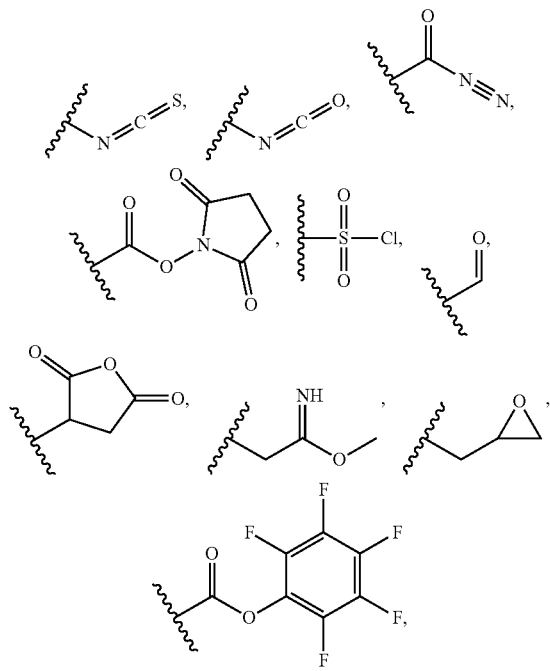

or —NH₂. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | thioethers |
| haloplatinate | heterocycle | platinum complex |
| haloplatinate | thiol | platinum complex |
| halotriazines | amines/anilines | platinum complex |
| halotriazines | alcohols/phenols | aminotriazines |
| halotriazines | thiols | triazinyl ethers |
| imido esters | amines/anilines | triazinyl thioethers |
| isocyanates | amines/anilines | amidines |
| isocyanates | alcohols/phenols | ureas |
| isothiocyanates | amines/anilines | urethanes |
| maleimides | thiols | thioureas |
| phosphoramidites | alcohols | thioethers |
| silyl halides | alcohols | phosphite esters |
| sulfonate esters | amines/anilines | silyl ethers |
| sulfonate esters | thiols | alkyl amines |
| sulfonate esters | carboxylic acids | thioethers |
| sulfonate esters | alcohols | esters |
| sulfonyl halides | amines/anilines | ethers |
| sulfonyl halides | phenols/alcohols | sulfonamides sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH₂, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 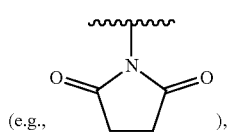 [SMILES: *N1C(=O)CCC1=O] ), thereby forming a bioconjugate (e.g., 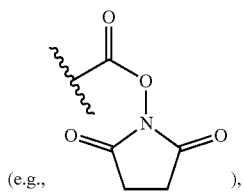 [SMILES: *C(=O)ON1C(=O)CCC1=O] ), In embodiments, the first bioconjugate reactive group (e.g., —NH$_2$) is covalently attached to the second bioconjugate reactive group (e.g., 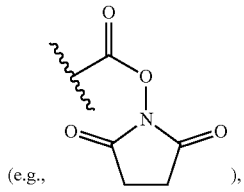 [SMILES: *C(=O)ON1C(=O)CCC1=O] ), thereby forming a bioconjugate (e.g., 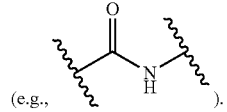 ).

In embodiments, the first bioconjugate reactive group (e.g., a coupling reagent) is covalently attached to the second bioconjugate reactive group (e.g., 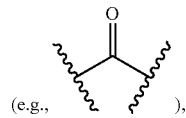 ), thereby forming a bioconjugate (e.g., 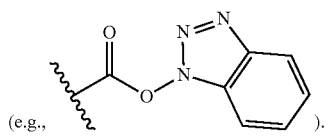 [SMILES: *C(=O)On1nnc2ccccc21] ).

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The term "covalent linker" is used in accordance with its ordinary meaning and refers to a divalent moiety which connects at least two moieties to form a molecule. The term "non-covalent linker" is used in accordance with its ordinary meaning and refers to a divalent moiety which includes at least two molecules that are not covalently linked to each other but are capable of interacting with each other via a non-covalent bond (e.g., electrostatic interactions (e.g., ionic bond, hydrogen bond, halogen bond) or van der Waals interactions (e.g., dipole-dipole, dipole-induced dipole, London dispersion). In embodiments, the non-covalent linker is the result of two molecules that are not covalently linked to each other that interact with each other via a non-covalent bond.

The term "adapter" as used herein refers to any oligonucleotide that can be ligated to a nucleic acid molecule, thereby generating nucleic acid products that can be sequenced on a sequencing platform (e.g., an Illumina or Singular Genomics G4™ sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing. In some embodiments, an adapter is hairpin adapter. In some embodiments, a hairpin adapter comprises a single nucleic acid strand comprising a stem-loop structure. In some embodiments, a hairpin adapter comprises a nucleic acid having a 5'-end, a 5'-portion, a loop, a 3'-portion and a 3'-end (e.g., arranged in a 5' to 3' orientation). In some embodiments, the 5' portion of a hairpin adapter is annealed and/or hybridized to the 3' portion of the hairpin adapter, thereby forming a stem portion of the hairpin adapter. In some embodiments, the 5' portion of a hairpin adapter is substantially complementary to the 3' portion of the hairpin adapter. In certain embodiments, a hairpin adapter comprises a stem portion (i.e., stem) and a loop, wherein the stem portion is substantially double stranded thereby forming a duplex. In some embodiments, the loop of a hairpin adapter comprises a nucleic acid strand that is not complementary (e.g., not substantially complementary) to itself or to any other portion of the hairpin adapter. In some embodiments, a method herein comprises ligating a first adapter to a first end of a double stranded nucleic acid, and ligating a second adapter to a second end of a double stranded nucleic acid. In some embodiments, the first adapter and the second adapter are different. For example, in certain embodiments, the first adapter and the second adapter may comprise different nucleic acid sequences or different structures. In some embodiments, the first adapter is a Y-adapter and the second adapter is a hairpin adapter. In some embodiments, the first adapter is a hairpin adapter and a second adapter is a hairpin adapter. In certain embodiments, the first adapter and the second adapter may comprise different primer binding sites, different structures, and/or different capture sequences (e.g., a sequence complementary to a capture nucleic acid). In some embodiments, some, all or substantially all of the nucleic acid sequence of a first adapter and a second adapter are the same. In some embodiments, some, all or substantially all of the nucleic acid sequence of a first adapter and a second adapter are substantially different.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

"Synthetic" agents refer to non-naturally occurring agents, such as enzymes or nucleotides derived or constructed using man-made techniques. Synthetic DNA polymerases refer to non-naturally occurring DNA polymerases such as those constructed by synthetic methods, mutated parent DNA polymerases such as truncated DNA polymerases and fusion DNA polymerases (e.g. U.S. Pat. No. 7,541,170). Variants of the parent DNA polymerase have been engineered by mutating residues using site-directed or random mutagenesis methods known in the art. In embodiments, the mutations are in any of Motifs I-VI. The variant is expressed in an expression system such as E. coli by methods known in the art.

The methods and kits of the present disclosure may be applied, mutatis mutandis, to the sequencing of RNA, or to determining the identity of a ribonucleotide.

"GC bias" describes the relationship between GC content and read coverage across a genome. For example, a genomic region of a higher GC content tends to have more (or less) sequencing reads covering that region. As described herein, GC bias can be introduced during amplification of library, cluster amplification, and/or the sequencing reactions.

A "substituent group," as used herein, means a group selected from the following moieties:

(A) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —O CHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_8$ alkyl, $C_1$-$C_6$ alkyl, or $C_1$-$C_4$ alkyl), heteroalkyl (e.g., 2 to 8 membered heteroalkyl, 2 to 6 membered heteroalkyl, or 2 to 4 membered heteroalkyl), cycloalkyl (e.g., $C_3$-$C_8$ cycloalkyl, $C_3$-$C_6$ cycloalkyl, or $C_5$-$C_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —S$O_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. An alkenyl includes one or more double bonds. An alkynyl includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH=CHO—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. A heteroalkenylene includes one or more double bonds. A heteroalkynylene includes one or more triple bonds.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions, Substrates, & Kits

In an aspect is a substrate (e.g., a solid support) including a first polynucleotide attached to the substrate; a second polynucleotide attached to the substrate, wherein the second polynucleotide includes a complementary sequence to the first polynucleotide; and a third polynucleotide (alternatively referred to herein as an invasion primer or extended invasion primer) hybridized to the second polynucleotide. In embodiments, the substrate further includes a plurality of immobilized oligonucleotides (e.g., immobilized primers, such as immobilized forward and immobilized reverse primers) attached to the substrate via a linker. In embodiments, the first and second polynucleotides are covalently attached to the substrate. In embodiments, the 5' end of the first and second polynucleotides contains a functional group that serves to tether the first and second polynucleotides to the substrate (e.g., a bioconjugate linker). Non-limiting examples of covalent attachment include amine-modified polynucleotides reacting with epoxy or isothiocyanate groups on the substrate, succinylated polynucleotides reacting with aminophenyl or aminopropyl functional groups on the substrate, dibenzocyclooctyne-modified polynucleotides reacting with azide functional groups on the substrate (or vice versa), trans-cyclooctyne-modified polynucleotides reacting with tetrazine or methyl tetrazine groups on the substrate (or vice versa), disulfide modified polynucleotides reacting with mercapto-functional groups on the substrate, amine-functionalized polynucleotides reacting with carboxylic acid groups on the core via 1-ethyl-3-(3-dimethylaminopropyl)-carbodiimide hydrochloride (EDC) chemistry, thiol-modified polynucleotides attaching to a substrate via a disulfide bond or maleimide linkage, alkyne-modified polynucleotides attaching to a substrate via copper-catalyzed click reactions to azide functional groups on the substrate, and acrydite-modified polynucleotides polymerizing with free acrylic acid monomers on the substrate to form polyacrylamide or reacting with thiol groups on the substrate. In embodiments, the primer is attached to the substrate polymer through electrostatic binding. For example, the negatively charged phosphate backbone of the primer may be bound electrostatically to positively charged monomers in the substrate. In embodiments, the third polynucleotide is not covalently attached to the substrate.

In embodiments, the substrate includes a plurality of first polynucleotides attached to a solid support; a plurality of second polynucleotides attached to a solid support; and a plurality of third polynucleotides hybridized to each of the second polynucleotides. It is understood that when referring to first, second, and third polynucleotides it is in reference to a class of polynucleotide types. For example, the polynucleotides of the first polynucleotides are substantially similar to each other insomuch as they contain substantially identical sequences.

In embodiments, the third polynucleotide, which may also be referred to as the invasion primer and is interchangeable with the third polynucleotide, includes locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), or combinations thereof. In embodiments, the third polynucleotide includes Bis-locked nucleic acids (bisLNAs). In embodiments, the third polynucleotide includes twisted intercalating nucleic acids (TINAs). In embodiments, the third polynucleotide includes bridged nucleic acids (BNAs). In embodiments, the third polynucleotide includes 2'-O-methyl RNA:DNA chimeric nucleic acids. In embodiments, the third polynucleotide includes minor groove binder (MGB) nucleic acids. In embodiments, the third polynucleotide includes morpholino nucleic acids. Morpholino nucleic acids are synthetic nucleotides that have standard nucleic acid bases (e.g., adenine, guanine, cytosine, and thymine) wherein those bases are bound to methylenemorpholine rings linked through phosphorodiamidate groups instead of phosphates. Morpholino nucleic acids may be referred to as phosphorodiamidate morpholino oligomers (PMOs). In embodiments, the third polynucleotide includes C5-modified pyrimidine nucleic acids. In embodiments, the third polynucleotide includes peptide nucleic acids (PNAs). In embodiments, the third polynucleotide includes from 5' to 3' a plurality of synthetic nucleotides (e.g., LNAs) followed by a plurality (e.g., 2 to 5) canonical or native nucleotides (e.g., dNTPs). In embodiments, the third polynucleotide comprises one or more (e.g., 2 to 5) deoxyuracil nucleobases (dU). In embodiments, the one or more dU nucleobases are at or near the 3' end of the third polynucleotide (e.g., within 5 nucleotides of the 3' end). In embodiments, the third polynucleotide includes from 5' to 3' a plurality (e.g., 2 to 5) of phosphorothioate nucleic acids, followed by a plurality of synthetic nucleotides (e.g., LNAs), and subsequently followed by a plurality (e.g., 2 to 5) of canonical nucleobases. In some embodiments, the third polynucleotide includes a plurality of canonical nucleobases, wherein the canonical nucleobases terminate (i.e., at the 3' end) with a deoxyuracil nucleobase (dU).

In embodiments, the third polynucleotide includes a plurality of LNAs interspersed throughout the polynucleotide. In embodiments, the third polynucleotide includes a plurality of consecutive LNAs (e.g., 2 to 5 LNAs, 5 to 7 LNAs, or 7 to 10 LNAs) throughout the polynucleotide. In embodiments, the entire composition of the third polynucleotide includes less than 70%, less than 60%, less than 50%, less than 40%, less than 30%, less than 20%, less than 10%, or less than 5% of LNAs. In embodiments, the entire composition of the third polynucleotide includes up to about 70%, up to about 60%, up to about 50%, up to about 40%, up to about 30%, up to about 20%, up to about 10%, or up to about 5% of LNAs. In embodiments, the entire composition of the third polynucleotide includes more than 60%, more than 50%, more than 40%, more than 30%, more than 20%, more than 10%, or more than 5% of LNAs. In embodiments, the entire composition of the third polynucleotide includes about 5% to about 10%, about 10% to about 20%, about 20% to about 30%, about 30% to about 40%, about 40% to about 50%, about 50% to about 60%, or about 60% to about 70% of LNAs. In embodiments, the entire composition of the third polynucleotide includes about 5%, about 10%, about 15%, about 20%, about 25%, about 30%, about 35%, about 40%, about 45%, about 50%, about 55%, about 60%, about 65%, or about 70% of LNAs. In embodiments, the entire composition of the third polynucleotide includes about 30%, about 35%, about 40%, about 45%, about 50%, about 55%, about 60%, about 65%, about 70%, about 75%, about 80%, about 85%, about 90%, or about 95% of canonical dNTPs. In embodiments, the entire composition of the third polynucleotide includes less than 95%, less than 90%, less than 80%, less than 70%, less than 60%, less than 50%, less than 40%, or less than 30% of canonical dNTPs. In embodiments, the entire composition of the third polynucleotide includes up to about 95%, up to about 90%, up to about 80%, up to about 70%, up to about 60%, up to about 50%, up to about 40%, or up to about 30% of canonical dNTPs. In embodiments, the entire composition of the third polynucleotide includes more than 90%, more than 80%, more than 70%, more than 60%, more than 50%, more than 40%, or more than 30% of canonical dNTPs.

In embodiments, the entire composition of the third polynucleotide includes about 70% of LNAs and about 30% of canonical dNTPs. In embodiments, the entire composition of the third polynucleotide includes about 65% of LNAs and about 35% of canonical dNTPs. In embodiments, the entire composition of the third polynucleotide includes about 60% of LNAs and about 40% of canonical dNTPs. In embodiments, the entire composition of the third polynucleotide includes about 55% of LNAs and about 45% of canonical dNTPs. In embodiments, the entire composition of the third polynucleotide includes about 50% of LNAs and about 50% of canonical dNTPs. In embodiments, the entire composition of the third polynucleotide includes about 45% of LNAs and about 55% of canonical dNTPs. In embodiments, the entire composition of the third polynucleotide includes about 40% of LNAs and about 60% of canonical dNTPs. In embodiments, the entire composition of the third polynucleotide includes about 35% of LNAs and about 65% of canonical dNTPs. In embodiments, the entire composition of the third polynucleotide includes about 30% of LNAs and about 70% of canonical dNTPs. In embodiments, the entire composition of the third polynucleotide includes about 25% of LNAs and about 75% of canonical dNTPs. In embodiments, the entire composition of the third polynucleotide includes about 20% of LNAs and about 80% of canonical dNTPs. In embodiments, the entire composition of the third polynucleotide includes about 15% of LNAs and about 85% of canonical dNTPs. In embodiments, the entire composition of the third polynucleotide includes about 10% of LNAs and about 90% of canonical dNTPs. In embodiments, the entire composition of the third polynucleotide includes about 5% of LNAs and about 95% of canonical dNTPs.

In embodiments, the third polynucleotide includes one or more dT nucleobases that are replaced with dU nucleobases.

In embodiments, the third polynucleotide includes a plurality of dT nucleobases that are replaced with dU nucleobases. In embodiments, the third polynucleotide includes all dT nucleobases replaced with dU nucleobases. In embodiments, the third polynucleotide includes dU nucleobases and LNA nucleotides. In embodiments, the third polynucleotide includes dU nucleobases and LNA nucleotides, wherein the LNA nucleotides are not adjacent to the dU nucleobases.

In embodiments, the third polynucleotide includes a homologous recombination complex including a recombinase bound thereto. In embodiments, the homologous recombination complex further includes a loading factor, a single-stranded binding (SSB) protein, or both.

In embodiments, the substrate includes a silica surface including a polymer coating. In embodiments, the substrate is silica or quartz, such as a microscope slide, having a surface that is uniformly silanized. This may be accomplished using conventional protocols, such as those described in Beattie et al (1995), Molecular Biotechnology, 4: 213. Such a surface is readily treated to permit end-attachment of oligonucleotides (e.g., forward and reverse primers) prior to amplification. In embodiments the substrate surface further includes a polymer coating, which contains functional groups capable of immobilizing primers. In some embodiments, the substrate includes a patterned surface suitable for immobilization of primers in an ordered pattern. A patterned surface refers to an arrangement of different regions in or on an exposed layer of a substrate. For example, one or more of the regions can be features where one or more primers are present. The features can be separated by interstitial regions where capture primers are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or interstitial regions. In some embodiments, the primers are randomly distributed upon the substrate. In some embodiments, the primers are distributed on a patterned surface.

In embodiments, the first polynucleotide is immobilized on the substrate via a first linker and the second polynucleotide is immobilized to the substrate via a second linker. The linkers may also include spacer nucleotides. Including spacer nucleotides in the linker puts the polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the solid support or is attached through a very short linker (e.g., a linker comprising about 1 to 3 carbon atoms). Spacer nucleotides form part of the polynucleotide but do not participate in any reaction carried out on or with the polynucleotide (e.g. a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use polyT spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of polynucleotides which are attached to a suitable support. Attachment can be achieved via a phosphorothioate present at the 5' end of the polynucleotide, an azide moiety, a dibenzocyclooctyne (DBCO) moiety, or any other bioconjugate reactive moiety. The linker may be a carbon-containing chain such as those of formula —(CH$_2$)n- wherein "n" is from 1 to about 1000. However, a variety of other linkers may be used so long as the linkers are stable under conditions used in DNA sequencing. In embodiments, the linker includes polyethylene glycol (PEG) having a general formula of —(CH$_2$—CH$_2$—O)m-, wherein m is from about 1 to 500, 1 to 100, or 1 to 12.

In embodiments, the linker, or the immobilized oligonucleotides (e.g., primers) include a cleavable site. In embodiments, a cleavable site is a location which allows controlled cleavage of the immobilized polynucleotide strand (e.g., the linker, the primer, or the polynucleotide) by chemical, enzymatic or photochemical means. In embodiments, the cleavable site includes one or more deoxyuracil nucleobases (dUs).

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavable site is an appropriate restriction site for the enzyme which directs cleavage of one or both strands of a duplex template; RNase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, the linker, the primer, or the first or second polynucleotide includes a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate (NaIO$_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, each of the plurality of immobilized oligonucleotides (e.g., immobilized primers) is about 5 to about 25 nucleotides in length. In embodiments, each of the plurality of immobilized oligonucleotides (e.g., immobilized primers) is about 10 to about 40 nucleotides in length. In embodiments, each of the plurality of immobilized oligonucleotides (e.g., immobilized primers) is about 5 to about 100 nucleotides in length. In embodiments, each of the plurality of immobilized oligonucleotides (e.g., immobilized primers) is about 20 to 200 nucleotides in length. In embodiments, each of the plurality of immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification, including a 3' phosphate moiety, which is removed by a PNK enzyme or a phosphatase enzyme. Alternatively, abasic site cleavage with certain endonucleases (e.g., Endo IV) results in a 3'-OH at the cleavable site from the 3'-diesterase activity.

In embodiments, the immobilized oligonucleotides includes one or more phosphorothioate nucleic acids. In embodiments, the immobilized oligonucleotides includes a plurality of phosphorothioate nucleic acids. In embodiments, about or at least about 20%, 30%, 40%, 50%, 60%, 70%, 80%, 90%, or about 100% of the nucleotides in the immobilized oligonucleotides are phosphorothioate nucleic acids. In embodiments, most of the nucleotides in the immobilized oligonucleotides are phosphorothioate nucleic acids. In embodiments, all of the nucleotides in the immobilized oligonucleotides are phosphorothioate nucleic acids. In embodiments, none of the nucleotides in the immobilized oligonucleotides are phosphorothioate nucleic acids. In embodiments, the 5' end of the immobilized oligonucleotide includes one or more phosphorothioate nucleic acids. In embodiments, the 5' end of the immobilized oligonucleotide includes between one and five phosphorothioate nucleic acids.

In embodiments, the first and second polynucleotides are each attached to the solid support (i.e., immobilized on the surface of a solid support). The polynucleotide molecules can be fixed to surface by a variety of techniques, including covalent attachment and non-covalent attachment. In embodiments, the polynucleotides are confined to an area of a discrete region (referred to as a cluster). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have polynucleotides that exceeds the amount or concentration present at the interstitial regions. In some embodiments the polynucleotides and/or primers may not be present at the interstitial regions. In embodiments, at least two different primers are attached to the solid support (e.g., a forward and a reverse primer), which facilitates generating multiple amplification products from the first extension product or a complement thereof.

In embodiments of the methods and compositions provided herein, the clusters have a mean or median separation from one another of about 0.5-5 μm. In embodiments, the mean or median separation is about 0.1-10 microns, 0.25-5 microns, 0.5-2 microns, 1 micron, or a number or a range between any two of these values. In embodiments, the mean or median separation is about or at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4., 4.5, 4.6, 4.7, 4.8, 4.9, 5.0 μm or a number or a range between any two of these values. In embodiments, the mean or median separation is about 0.1-10 microns. In embodiments, the mean or median separation is about 0.25-5 microns. In embodiments, the mean or median separation is about 0.5-2 microns. In embodiments, the mean or median separation is about or at least about 0.1 μm. In embodiments, the mean or median separation is about or at least about 0.25 μm. In embodiments, the mean or median separation is about or at least about 0.5 μm. In embodiments, the mean or median separation is about or at least about 1.0 μm. In embodiments, the mean or median separation is about or at least about 2.0 μm. In embodiments, the mean or median separation is about or at least about 5.0 μm. In embodiments, the mean or median separation is about or at least about 10 μm. The mean or median separation may be measured center-to-center (i.e., the center of one cluster to the center of a second cluster). In embodiments of the methods provided herein, the amplicon clusters have a mean or median separation (measured center-to-center) from one another of about 0.5-5 μm. The mean or median separation may be measured edge-to-edge (i.e., the edge of one amplicon cluster to the edge of a second amplicon cluster). In embodiments of the methods provided herein, the amplicon clusters have a mean or median separation (measured edge-to-edge) from one another of about 0.2-5 μm.

In embodiments of the methods provided herein, the amplicon clusters have a mean or median diameter of about 100-2000 nm, or about 200-1000 nm. In embodiments, the mean or median diameter is about 100-3000 nanometers, about 500-2500 nanometers, about 1000-2000 nanometers, or a number or a range between any two of these values. In embodiments, the mean or median diameter is about or at most about 100, 200, 300, 400, 500, 600, 700, 800, 900, 1,000, 1,100, 1,200, 1,300, 1,400, 1,500, 1,600, 1,700, 1,800, 1,900, 2000 nanometers or a number or a range between any two of these values. In embodiments, the mean or median diameter is about 100-3,000 nanometers. In embodiments, the mean or median diameter is about 100-2,000 nanometers. In embodiments, the mean or median diameter is about 500-2500 nanometers. In embodiments, the mean or median diameter is about 200-1000 nanometers. In embodiments, the mean or median diameter is about 1,000-2,000 nanometers. In embodiments, the mean or median diameter is about or at most about 100 nanometers. In embodiments, the mean or median diameter is about or at most about 200 nanometers. In embodiments, the mean or median diameter is about or at most about 500 nanometers. In embodiments, the mean or median diameter is about or at most about 400 nanometers. In embodiments, the mean or median diameter is about or at most about 500 nanometers. In embodiments, the mean or median diameter is about or at most about 600 nanometers. In embodiments, the mean or median diameter is about or at most about 700 nanometers. In embodiments, the mean or median diameter is about or at most about 1,000 nanometers. In embodiments, the mean or median diameter is about or at most about 2,000 nanometers. In embodiments, the mean or median diameter is about or at most about 2,500 nanometers. In embodiments, the mean or median diameter is about or at most about 3,000 nanometers.

In embodiments of the methods provided herein, each amplicon cluster (e.g., an amplicon cluster having a mean or median diameter of about 100-2000 nm, or about 200-1000 nm) includes about or at least about 100, 500, 1,000, 2,500, 5,000, 10,000, 15,000, 20,000, 25,000, 30,000, 35,000, 40,000, 45,000, or 50,000 dsDNA molecules. In embodiments, each amplicon cluster includes about 100 dsDNA molecules. In embodiments, each amplicon cluster includes about 500 dsDNA molecules. In embodiments, each amplicon cluster includes about 1000 dsDNA molecules. In embodiments, each amplicon cluster includes about 500 dsDNA molecules. In embodiments, each amplicon cluster includes about 1,000 dsDNA molecules. In embodiments, each amplicon cluster includes about 2,500 dsDNA molecules. In embodiments, each amplicon cluster includes about 5,000 dsDNA molecules. In embodiments, each amplicon cluster includes about 10,000 dsDNA molecules. In embodiments, each amplicon cluster includes about 20,000 dsDNA molecules. In embodiments, each amplicon cluster includes about 30,000 dsDNA molecules. In embodiments, each amplicon cluster includes about 40,000 dsDNA molecules. In embodiments, each amplicon cluster includes about 50,000 dsDNA molecules. In embodiments, each amplicon cluster includes more than about 50,000 dsDNA molecules.

In embodiments, the substrate is a particle. In embodiments, the substrate is a multiwell container. In embodiments, the substrate is a polymer coated particle or polymer coated planar support. In embodiments, the substrate includes a polymer. In embodiments, the particle includes polymerized units of polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, polyethylene glycol (PEG)-thiol/PEG-acrylate, acrylamide/N,N'-bis(acryloyl)cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), isocyanatoethyl methacrylate (IEM), or a copolymer thereof. In embodiments, the particle shell includes polymerized units of polyacrylamide (AAm), glicydyl methacrylate (GMA), polyethylene glycol methacrylate (PEGMA), polyethylene glycol methacrylate (PEGMA), isocyanatoethyl methacrylate (IEM), or a copolymer thereof. In embodiments, the particle includes polymerized units of polyethylene glycol methacrylate (PEGMA) and glicydyl methacrylate (GMA). In embodiments, the particle includes polymerized units of polyethylene glycol methacrylate (PEGMA) and isocyanatoethyl methacrylate (IEM). In embodiments, the particle includes polymerized units of 3-azido-2-hydroxypropyl methacrylate, 2-azido-3-hydroxypropyl methacrylate, 2-(((2-azidoethoxy)carbonyl)amino)ethyl methacrylate, 3-azido-2-hydroxypropyl acrylate, 2-azido-3-hydroxypropyl acrylate, or 2-(((2-azidoethoxy)carbonyl)amino)ethyl acrylate. In embodiments, the particle includes polymerized units of 3-azido-2-hydroxypropyl methacrylate, 2-azido-3-hydroxypropyl methacrylate, or 2-(((2-azidoethoxy)carbonyl)amino)ethyl methacrylate. In embodiments, the particle includes polymerized units of 3-azido-2-hydroxypropyl methacrylate. In embodiments, the particle includes polymerized units of 3-azido-2-hydroxypropyl methacrylate 2-azido-3-hydroxypropyl methacrylate. In embodiments, the particle includes polymerized units of 3-azido-2-hydroxypropyl methacrylate 2-(((2-azidoethoxy)carbonyl)amino)ethyl methacrylate.

In an aspect is a kit, wherein the kit includes the substrate as described herein. Generally, the kit includes one or more containers providing a composition and one or more additional reagents (e.g., a buffer suitable for polynucleotide extension). The kit may also include a template nucleic acid (DNA and/or RNA), one or more primer polynucleotides, nucleoside triphosphates (including, e.g., deoxyribonucleotides, ribonucleotides, labeled nucleotides, and/or modified nucleotides), buffers, salts, and/or labels (e.g., fluorophores).

In embodiments, the kit includes a sequencing polymerase, and one or more amplification polymerases. In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

In an aspect is provided a polynucleotide (e.g., an invasion primer). In embodiments, the polynucleotide includes a plurality of LNA nucleotides; one or more cleavable sites, wherein the one or more cleavable sites partition the invasion primer into two or more regions; and a plurality of native nucleotides.

In an aspect is provided a polynucleotide (e.g., an invasion primer). In embodiments, the polynucleotide includes a plurality of LNA nucleotides; one or more dU nucleobases, wherein the one or more dU nucleobases partition the invasion primer into two or more regions; and a plurality of native nucleotides.

In embodiments, the polynucleotide is 20 to 40 nucleotides in length. In embodiments, the polynucleotide is about 10 to 100 nucleotides in length. In embodiments, the polynucleotide is about 15 to about 75 nucleotides in length. In embodiments, the polynucleotide is about 25 to about 75 nucleotides in length. In embodiments, the polynucleotide is about 15 to about 50 nucleotides in length. In embodiments, the polynucleotide is about 10 to about 20 nucleotides in length. In embodiments, the polynucleotide is about 10, 11, 12, 13, 14, 15, 16, 17, 18, 19, or about 20 nucleotides in length. In embodiments, the polynucleotide is about 20, 21, 22, 23, 24, 25, 26, 27, 28, 29, or about 30 nucleotides in length. In embodiments, the polynucleotide is about 30, 31, 32, 33, 34, 35, 36, 37, 38, 39, or about 40 nucleotides in length. In embodiments, the polynucleotide is about 40, 41, 42, 43, 44, 45, 46, 47, 48, 49, or about 50 nucleotides in length. In embodiments, the polynucleotide is greater than 30 nucleotides in length. In embodiments, the polynucleotide is greater than 40 nucleotides in length. In embodiments, the polynucleotide is greater than 50 nucleotides in length. In embodiments, the polynucleotide is no less than 20 nucleotides. In embodiments, the polynucleotide is about 15 to about 35 nucleotides in length. In embodiments, the polynucleotide is about 25 to about 35 nucleotides, wherein 12 to 18 nucleotides are LNA nucleotides. In embodiments, the polynucleotide is about 25 to about 35 nucleotides, wherein 14 to 16 nucleotides are LNA nucleotides. In embodiments, the polynucleotide is about 30 to about 35 nucleotides, wherein 14 to 16 nucleotides are LNA nucleotides. In embodiments, the polynucleotide is 30, 31, 32, or 33 nucleotides, wherein 14 to 16 nucleotides are LNA nucleotides.

In embodiments, the calculated or predicted melting temperature (Tm) of the polynucleotide is about 70° C. to about 95° C. In embodiments, the calculated or predicted melting temperature (Tm) of the polynucleotide is about 80° C. to about 95° C. In embodiments, the calculated or predicted melting temperature (Tm) of the polynucleotide is about 85° C. to about 95° C. In embodiments, the calculated or predicted melting temperature (Tm) of the polynucleotide is about 85° C. to about 90° C. In embodiments, the plurality of LNA nucleotides are interspersed throughout the polynucleotide.

In embodiments, the one or more dU nucleobases partition the polynucleotide into two or more regions of nucleotides (e.g., a first plurality of consecutive nucleotides and a second plurality of consecutive nucleotides are separated by the one or more dU nucleobases). In embodiments each of the two or more regions of consecutive nucleotides are each about 3 to about 10 nucleotides in length, or about 3 to about 15 nucleotides in length. In embodiments each of the two or more regions of consecutive nucleotides are each about 3 to about 10 nucleotides in length. In embodiments each of the two or more regions of consecutive nucleotides are each about 3 to about 15 nucleotides in length. In embodiments each of the two or more regions of consecutive nucleotides are each at least about 3, 5, 7, 10, 13, or 15 nucleotides in length. In embodiments, each of the two or more regions of consecutive nucleotides is greater than about 15 nucleotides in length. In embodiments, the calculated or predicted melting temperature (Tm) of each of the two or more regions of consecutive nucleotides is about 50° C. to about 75° C. In embodiments, the calculated or predicted melting temperature (Tm) of each of the two or more regions of consecutive nucleotides is about 60° C. to about 75° C. In embodiments, the calculated or predicted melting temperature (Tm) of each of the two or more regions of consecutive nucleotides is about 50° C. to about 65° C. In embodiments, the calculated or predicted melting temperature (Tm) of each of the two or more regions of consecutive nucleotides is less than about 75° C. In embodiments, the calculated or predicted melting temperature (Tm) of each of the two or more regions of consecutive nucleotides is less than about 65° C. In embodiments, the calculated or predicted melting temperature (Tm) of each of the two or more regions of consecutive nucleotides is less than about 60° C.

III. Methods

In an aspect is provided a method of sequencing two or more regions of a double-stranded polynucleotide including a first strand hybridized to a second strand, wherein the first strand and second strand are both attached to a solid support. In embodiments, the method includes: i) hybridizing an invasion primer to the second strand and extending the invasion primer with a polymerase, thereby generating an invasion strand; ii) hybridizing a sequencing primer to the first strand; iii) incorporating one or more nucleotides into the sequencing primer with a polymerase to create an extension strand; and iv) detecting the one or more incorporated nucleotides so as to identify each incorporated nucleotide in the extension strand, thereby sequencing the first strand of the double-stranded polynucleotide. In embodiments, the method further includes removing the first strand, removing the invasion strand, or both removing the first strand and removing the invasion strand. In embodiments, the method further includes removing the invasion strand and hybridizing a second invasion primer to the first strand and extending the second invasion primer with a polymerase, thereby generating a second invasion strand.

In embodiments, the method includes nicking and/or cleaving the invasion strand to generate a 3' end and incorporating one or more nucleotides into the 3' end of the invasion primer with a polymerase to create an extension strand; and detecting the one or more incorporated nucleotides so as to identify each incorporated nucleotide in said extension strand.

In an aspect is provided a method of forming a plurality of single-stranded polynucleotides attached to a solid support. In embodiments, the method includes: contacting a plurality of double-stranded polynucleotides including a first strand hybridized to a second strand with a plurality of invasion primers, wherein the first strand and the second strand are attached to the solid support; hybridizing one or more invasion primers to the second strand; and extending one or more invasion primers hybridized to the second strand with a polymerase to generate one or more invasion strands, displacing the first strand, thereby forming a plurality of single-stranded polynucleotides attached to the solid support. In embodiments, the method further includes sequencing the single-stranded polynucleotides. In embodiments, the method further includes removing the invasion strand and sequencing the second strand.

In embodiments, the solid support includes about 100, 500, 1000, 5000, 10000, or more dsDNA molecules in a 2 µm² area. In embodiments, the solid support includes about 1,000 to about 10,000 dsDNA molecules in a 2 µm² area. In embodiments, the solid support includes about 1,000 to about 10,000 dsDNA molecules in a 0.5 µm diameter feature. In embodiments, the solid support includes about 1,000 to about 50,000 dsDNA molecules in a 500, 600, 700, 800, 900, or 1,000 nm diameter feature. In embodiments, the solid support includes about 10,000 to about 50,000 dsDNA molecules in a 500, 600, 700, 800, 900, or 1,000 nm diameter feature. In embodiments, the solid support includes about 20,000 to about 40,000 dsDNA molecules in a 500, 600, 700, 800, 900, or 1,000 nm diameter feature. In embodiments, the solid support includes about 30,000 to about 40,000 dsDNA molecules in a 500, 600, 700, 800, 900, or 1,000 nm diameter feature. As used herein, a feature may be a wells, pits, channels, ridges, raised regions, pegs, or posts on a solid support. Each feature includes a colony and refers to a discrete site on a solid support that includes a plurality of immobilized polynucleotides.

In embodiments, removing the invasion strand includes digesting (i.e., cleaving internal phosphodiester bonds of a polynucleotide) all or portions thereof of the invasion strand using an exonuclease enzyme. Exonucleases can be active on ssDNA and/or dsDNA, initiate from the 5' end and/or the 3' end of polynucleotides, and can also act on RNA polynucleotides. In embodiments, the exonuclease enzyme is a DNA specific exonuclease. In embodiments, the exonuclease catalyzes the removal of nucleotides from linear, and/or nicked double-stranded DNA in the 5' to 3' direction.

In an aspect is provided a method of sequencing a template polynucleotide. In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing one or more invasion primers (e.g., one or more first invasion primers) to the second strand, and extending the one or more invasion primers (e.g., extending the one or more first invasion primers with a polymerase under strand-displacing conditions); and generating a first sequencing read by hybridizing one or more sequencing primers (e.g., one or more first sequencing primers) to the first strand, and extending the one or more first sequencing primers. In embodiments, when hybridized to the second strand, the first invasion strand blocks and/or prevents rehybridization of the complementary first strand. In embodiments, the invasion primer is not covalently attached to the solid support. In embodiments, the invasion strand, alternatively referred to herein as the third polynucleotide, is not covalently attached to the solid support.

In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing an invasion primer to the second strand, and extending the invasion primer, wherein the invasion primer is not covalently attached to the solid support; and generating a first sequencing read by hybridizing one or more sequencing primers to the first strand, and extending the one or more first sequencing primers. In embodiments, the invasion primer does not hybridize at the end of the strand, rather the invasion primer hybridizes about 5 to about 50 nucleotides from the end of the strand. In embodiments, the invasion primer hybridizes about 10 to about 30 nucleotides, about 12 to about 24, or about 15 to about 30 from the end of the strand. In embodiments, the invasion primer hybridizes towards the 5' end of the strand. In embodiments, the invasion primer hybridizes towards the 3' end of the strand. In embodiments, the invasion primer does hybridize at the end of the strand (e.g., the invasion primer hybridizes to the last nucleotide on the strand).

In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing an invasion primer (e.g., a first invasion primer) to the second strand, and extending the first invasion primer (e.g., extending the first invasion primers with a polymerase under strand-displacing conditions); and generating a first sequencing read by hybridizing one or more first sequencing primers to the first strand, and extending the one or more first sequencing primers. In embodiments, when hybridized to the second strand, the first invasion strand blocks and/or prevents rehybridization of the complementary first strand. In embodiments, the first invasion primer is not covalently attached to the solid support. In embodiments, the invasion strand is not covalently attached to the solid support.

In embodiments, each invasion primer of the one or more invasions primers is complementary to the same sequence (e.g., the same sequence in the first strand or the same sequence in the second strand). In embodiments, each invasion primer of the one or more invasion primers is not complementary to a different sequence (e.g., a different sequence in the first strand or a different sequence in the second strand). In embodiments, each invasion primer of the one or more invasion primers is complementary to a different sequence (e.g., a different sequence in the first strand or a different sequence in the second strand). In embodiments, one or more invasions primers is complementary to the same sequence (e.g., the same sequence in the first strand or the same sequence in the second strand). In embodiments, one or more invasion primers is not complementary to a different sequence (e.g., a different sequence in the first strand or a different sequence in the second strand). In embodiments, one or more invasion primers is complementary to a different sequence (e.g., a different sequence in the first strand or a different sequence in the second strand).

In embodiments, the first strand is covalently attached to the solid support via a first linker and the second strand is covalently attached to the solid support via a second linker. The linker tethering the polynucleotide strands may be any linker capable of localizing nucleic acids to arrays. The linkers may be the same, or the linkers may be different. Solid-supported molecular arrays have been generated previously in a variety of ways, for example, the attachment of biomolecules (e.g., proteins and nucleic acids) to a variety of substrates (e.g., glass, plastics, or metals) underpins modern microarray and biosensor technologies employed for genotyping, gene expression analysis and biological detection. Silica-based substrates are often employed as supports on which molecular arrays are constructed, and functionalized silanes are commonly used to modify glass to permit a click-chemistry enabled linker to tether the biomolecule.

In embodiments, the method further includes generating a second invasion strand hybridized to the first strand by hybridizing one or more second invasion primers to the first strand, and extending the one or more second invasion primers; and generating a second sequencing read by hybridizing one or more second sequencing primers to the second strand, and extending the one or more second sequencing primers. In embodiments, the second invasion strand is not covalently attached to the solid support. In embodiments, the method further includes removing the first invasion strand; generating a second invasion strand hybridized to the first strand by hybridizing one or more invasion primers to the first strand, and extending the one or more second invasion primers; and generating a second sequencing read by hybridizing one or more second sequencing primers to the second strand, and extending the one or more second sequencing primers. In embodiments, the method further includes generating a second invasion strand hybridized to the first strand by hybridizing a second invasion primer to the first strand, and extending the second invasion primer; and generating a second sequencing read by hybridizing one or more second sequencing primers to the second strand, and extending the one or more second sequencing primers. In embodiments, the second invasion strand is not covalently attached to the solid support. In embodiments, the method further includes removing the first invasion strand; generating a second invasion strand hybridized to the first strand by hybridizing a second invasion primer to the first strand, and extending the second invasion primers; and generating a second sequencing read by hybridizing one or more second sequencing primers to the second strand, and extending the one or more second sequencing primers. In embodiments, the method includes sequencing both strands (i.e., the first and the second strand) of the sample double-stranded amplification product. In embodiments, the method includes sequencing both strands (i.e., the first and the second strand) of the template polynucleotide.

In embodiments, the double-stranded amplification product includes common sequences at their 5' and 3' ends. In this context the term "common" is interpreted as meaning common to all templates in the library. For example, the double-stranded amplification product may include a first adapter sequence at the 5' end and a second adapter sequence at the 3' end. Typically, the first adapter sequence and the second adapter sequence will consist of no more than 100, or no more than 50, or no more than 40 consecutive nucleotides at the 5' and 3' ends, respectively, of each strand of each template polynucleotide. The precise length of the two sequences may or may not be identical. The precise sequences of the common regions are generally not material to the invention and may be selected by the user. The common sequences must at least include primer-binding sequences (i.e., regions of complementarity for a primer) which enable specific annealing of primers when the template polynucleotides are in used in a solid-phase amplification reaction. The primer-binding sequences are thus determined by the sequence of the primers to be ultimately used for solid-phase amplification.

In embodiments, generating the invasion strand (i.e., generating the first invasion strand or the second invasion strand) includes hybridizing one or more primers to a common sequence in the double-stranded amplification product. In embodiments, generating the invasion strand (i.e., generating the first invasion strand or the second invasion strand) includes hybridizing one primer to a common sequence in the double-stranded amplification product. In embodiments, generating the invasion strand (i.e., generating the first invasion strand or the second invasion strand) includes hybridizing a primer to at or near the 3' end of the double-stranded amplification product. In embodiments, generating the invasion strand (i.e., generating the first invasion strand or the second invasion strand) includes hybridizing a primer to at or near the 3' end of the double-stranded amplification product, wherein the primer is not covalently attached to the solid support (e.g., the primer is in solution prior to hybridization). In embodiments, the invasion primer does not hybridize at the terminus of the strand, rather the invasion primer hybridizes about 10, about 20, about 30, or about 50 nucleotides from the terminus of the strand. In embodiments, the invasion primer hybridizes about 10 to about 30 nucleotides from the terminus of the strand. In embodiments, the invasion primer hybridizes to a common sequence (e.g., a sequence described in U.S. Patent Publication 2016/0256846, which is incorporated herein by reference, for example SEQ ID NO: 3, SEQ ID NO: 4, SEQ ID NO: 5, or SEQ ID NO: 11 of U.S. Patent Publication 2016/0256846).

In embodiments, the method further includes removing the first strand by cleaving the first strand at a cleavable site, washing away the cleaved strand, and generating a second sequencing read by hybridizing one or more second sequencing primers to the second strand; and extending the one or more second sequencing primers. In embodiments, removing the first strand is optional. The one or more cleavable sites may include a modified nucleotide, ribonucleotide, or a sequence containing a modified or unmodified nucleotide that is specifically recognized by a cleavage agent. The cleavable site(s) may be deoxyuracil triphosphate (dUTP), deoxy-8-Oxo-guanine triphosphate (d-8-oxoG), or other modified nucleotide(s), such as those described, for example, in US 2012/0238738, which is incorporated herein by reference for all purposes. In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent. In embodiments, the cleavable site includes one or more ribonucleotides. In embodiments, the cleavable site includes 2 to 5 ribonucleotides. In embodiments, the cleavable site includes one ribonucleotide. In embodiments, the cleavable sites can be cleaved at or near a modified nucleotide or bond by enzymes or chemical reagents, collectively referred to here and in the claims as "cleaving agents." Examples of cleaving agents include DNA repair enzymes, glycosylases, DNA cleaving endonucleases, or ribonucleases. For example, cleavage at dUTP may be achieved using uracil DNA glycosylase and endonuclease VIII (USER™, NEB, Ipswich, Mass.), as described in U.S. Pat. No. 7,435,572. In embodiments, when the modified nucleotide is a ribonucleotide, the cleavable site can be cleaved with an endoribonuclease. In embodiments, cleaving an extension product includes contacting the cleavable site with a cleaving agent, wherein the cleaving agent includes a reducing agent, sodium periodate, RNase, formamidopyrimidine DNA glycosylase (Fpg), endonuclease, restriction enzyme, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C. (e.g., 65° C.).

In embodiments, prior to generating a first invasion strand, the method includes removing immobilized primers that do not contain a first or second strand (i.e., unused primers). Methods of removing immobilized primers can include digestion using an enzyme with exonuclease activity. Removing unused primers may serve to increase the free volume and allow for greater accessibility of the invasion primer. Removal of unused primers may also prevent opportunities for the newly released first strand to rehybridize to an available surface primer, producing a priming site off the available surface primer, thereby facilitating the "reblocking" of the released first strand. In embodiments, prior to generating a first invasion strand, the method includes contacting the immobilized primers with an exonuclease enzyme.

In embodiments, prior to generating a first invasion strand, the method includes blocking the immobilized primers that do not include a first or second strand. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, prior to generating a first invasion strand the method includes incubating the amplification products with dideoxynucleotide triphosphates (ddNTPs) to block the 3'-OH of the immobilized oligonucleotides from future extension. In embodiments, prior to generating a first invasion strand, the method includes incorporating a dideoxynucleotide triphosphate (ddNTP) into an immobilized primer. In embodiments, prior to generating a first invasion strand, the method includes contacting the immobilized primer with a polymerase. In embodiments, during generation of a first invasion strand, the method includes contacting the immobilized primer with a polymerase buffer (e.g., incubating the solid support with a buffered solution including a polymerase).

In embodiments, the first strand is cleaved after generating the first sequencing read but before generating the second sequencing read. In embodiments, the first strand is not cleaved after generating the first sequencing read. Cleaving one strand of the double-stranded amplification product may be referred to as linearization. Suitable methods for linearization are known, and described in more detail in application number U.S. Patent Publication 2009/0118128, which is incorporated herein by reference in its entirety. For example, the first strand may be cleaved by exposing the first strand to a mixture containing a glycosylase and one or more suitable endonucleases. In embodiments, the first strand is attached to the surface in a way that allows for selective removal. If the first template strand is removed from the surface, and the partially double-stranded amplification product is denatured, for example by treatment with hydroxide or formamide, then the second strand remains immobilized as a linearized single strand. If one of the surface immobilized primers includes a cleavable site such that it can be cleaved from the surface, (e.g., diol linkage) the resulting partially double-stranded amplification product can be made single-stranded using heat, or chemical denaturing agents, or a combination thereof providing conditions to give a single strand containing a primer hybridization site.

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavable site is an appropriate restriction site for the enzyme which directs cleavage of one or both strands of a duplex template; RNase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, one strand of the double-stranded amplification product (or the surface immobilized primer) may include a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance which promotes cleavage of the diol (e.g., a diol-cleaving agent). In embodiments, the diol-cleaving agent is periodate, e.g., aqueous sodium periodate (NaIO$_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine.

In embodiments, the cleavable site is not in the immobilized primer sequence (e.g., within the polynucleotide sequence of the primer). In embodiments, the cleavable site is included in the linking moiety responsible for tethering the primer to the substrate. In embodiments, the cleavable site is a cleavable linker (e.g., a disulfide containing linker that cleaves when exposed to a reducing agent). In embodiments, the cleavable site is a diol linker.

In embodiments, the first strand includes at least one cleavable site. In embodiments, the first linker includes at least one cleavable site. In embodiments, the cleavable site includes deoxyuracil triphosphate (dUTP). The enzyme uracil DNA glycosylase (UDG) may then be used to remove dUTP, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali. In embodiments, the USER™ reagent available from New England Biolabs (NEB catalog #M5508) is used for the creation of a single nucleotide gap at a uracil base in a duplex strand.

In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, the cleavable site includes one or more ribonucleotides. In embodiments, the cleavable site includes 2 to 5 ribonucleotides. In embodiments, the cleavable site includes one ribonucleotide. In embodiments, the cleavable site includes more than one ribonucleotide. In embodiments, the cleavable site includes deoxyuracil triphosphate (dUTP) or deoxy-8-oxo-guanine triphosphate (d-8-oxoG). In embodiments, the cleavable site includes two or more deoxyuracil triphosphate (dUTP). In embodiments, the cleavable site includes 2 to 15 dUTPs.

In embodiments, cleaving includes enzymatically cleaving the first strand at the at least one cleavable site (e.g., enzymatically cleaving with an endonuclease). In embodiments, the first strand includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, cleaving the first strand includes contacting the cleavable site with a cleaving agent, wherein the cleaving agent includes a reducing agent, sodium periodate, RNase, Formamidopyrimidine DNA Glycosylase (Fpg), endonuclease, restriction enzyme, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C. (e.g., 65° C.).

In embodiments, cleaving includes chemically cleaving the first strand at the at least one cleavable site. In embodiments, the first linker includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

In embodiments, the invasion primer is not covalently attached to the solid support. In embodiments, the invasion primer includes synthetic nucleotides. In embodiments, the invasion primer includes locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), or combinations thereof. In embodiments, the invasion primer includes locked nucleic acids (LNAs), Bis-locked nucleic acids (bisLNAs), twisted intercalating nucleic acids (TINAs), bridged nucleic acids (BNAs), peptide nucleic acids (PNAs), or combinations thereof. In embodiments, the invasion primer includes locked nucleic acids (LNAs). In embodiments, the invasion primer includes Bis-locked nucleic acids (bisLNAs). In embodiments, the invasion primer includes twisted intercalating nucleic acids (TINAs). In embodiments, the invasion primer includes bridged nucleic acids (BNAs). In embodiments, the invasion primer includes 2'-O-methyl RNA:DNA chimeric nucleic acids. In embodiments, the invasion primer includes minor groove binder (MGB) nucleic acids. In embodiments, the invasion primer includes morpholino nucleic acids. In embodiments, the invasion primer includes C5-modified pyrimidine nucleic acids. In embodiments, the invasion primer includes peptide nucleic acids (PNAs). In embodiments, the invasion primer includes locked nucleic acids (LNAs), Bis-locked nucleic acids (bisLNAs), twisted intercalating nucleic acids (TINAs), bridged nucleic acids (BNAs), peptide nucleic acids (PNAs), or combinations thereof.

In embodiments, the invasion primer includes locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, or combinations thereof. In embodiments, the invasion primer includes phosphorothioate nucleic acids. In embodiments, the invasion primer includes one or more locked nucleic acids (LNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids. In embodiments, the invasion primer includes one or more locked nucleic acids (LNAs). In embodiments, the invasion primer includes one or more 2-amino-deoxyadenosine (2-amino-dA). In embodiments, the invasion primer includes one or more trimethoxystilbene-functionalized oligonucleotides (TFOs). In embodiments, the invasion primer includes one or more Pyrene-functionalized oligonucleotides (PFOs). In embodiments, the invasion primer includes one or more peptide nucleic acids (PNAs). In embodiments, the invasion primer includes one or more aminoethyl-phenoxazine-dC (AP-dC) nucleic acids. In embodiments, the invasion primer includes 10 to 15 locked nucleic acids (LNAs). In embodiments, the invasion primer includes a sequence described herein, for example within Table 1. In embodiments, the invasion primer includes one or more phosphorothioates at the 5' end. In embodiments, the invasion primer includes one or more LNAs at the 5' end. In embodiments, the invasion primer includes two or more consecutive LNAs at the 3' end. In embodiments, the invasion primer includes two to four consecutive LNAs at the 3' end. In embodiments, the invasion primer includes two or more consecutive LNAs at the 5' end. In embodiments, the invasion primer includes two to four consecutive LNAs at the 5' end.

In embodiments, the invasion primer includes one or more locked nucleic acids (LNAs) at the 3' end of the invasion primer sequence. In embodiments, the invasion primer includes 2, 3, 4, 5, or more locked nucleic acids (LNAs) at the 3' end of the invasion primer sequence. In embodiments, the invasion primer includes a plurality of locked nucleic acids (LNAs) at the 3' end of the invasion primer sequence. In embodiments, the invasion primer includes one locked nucleic acid (LNA) at the 3' end of the invasion primer sequence. In embodiments, the invasion primer includes 2 locked nucleic acids (LNAs) at the 3' end of the invasion primer sequence. In embodiments, the invasion primer includes 3 locked nucleic acids (LNAs) at the 3' end of the invasion primer sequence. In embodiments, the invasion primer includes 4 locked nucleic acids (LNAs) at the 3' end of the invasion primer sequence. In embodiments, the invasion primer includes 5 locked nucleic acids (LNAs) at the 3' end of the invasion primer sequence.

In embodiments, the invasion primer includes from 5' to 3' a plurality of synthetic nucleotides (e.g., LNAs) followed by a plurality (e.g., 2 to 5) canonical or native nucleotides (e.g., dNTPs). In embodiments, the invasion primer comprises one or more (e.g., 2 to 5) deoxyuracil nucleobases (dU). In embodiments, the one or more dU nucleobases are at or near the 3' end of the invasion primer (e.g., within 5 nucleotides of the 3' end). In embodiments, the invasion primer includes from 5' to 3' a plurality (e.g., 2 to 5) of phosphorothioate nucleic acids, followed by a plurality of synthetic nucleotides (e.g., LNAs), and subsequently followed by a plurality (e.g., 2 to 5) of canonical bases. In some embodiments, the invasion primer includes a plurality of canonical bases, wherein the canonical bases terminate (i.e., at the 3' end) with a deoxyuracil nucleobase (dU).

In embodiments, the invasion primer includes the sequence provided in Table 1. In embodiments, the 5' end of the sequences provided in Table 1 include one or more phosphorothioate nucleic acids.

TABLE 1

Invasion primer sequences, from 5'-3', wherein the nucleotide contained in brackets indicates an LNA nucleotide.

| Nucleotide Sequence 5' to 3' | SEQ ID number |
|---|---|
| T[T]T[T]T[C]T[C]CA[G]CG[A]GATG[A]CCCT[C]A[C]CAAC[C][A][C] | SEQ ID NO: 1 |
| TTT[T]T[C]T[C]CA[G]CG[A]GATG[A]CCCT[C]A[C]CA[A]C[C][A][C] | SEQ ID NO: 2 |
| TTTTT[C]T[C]CA[G]CG[A]GATG[A]C[C]CT[C]A[C]CA[A]C[C][A][C] | SEQ ID NO: 3 |
| TTTTTCT[C]CA[G]CG[A]G[A]TG[A]C[C]CT[C]A[C]CA[A]C[C][A][C] | SEQ ID NO: 4 |
| T[T]T[T]T[C]T[C]CA[G]CG[A]GATG[A]CCCT[C]A[C]C[A]AC[C][A][C] | SEQ ID NO: 5 |
| T[T]T[T]T[C]T[C]CA[G]CG[A]GATG[A]C[C]CT[C]A[C]C[A]AC[C][A][C] | SEQ ID NO: 6 |
| T[T]T[T]T[C]T[C]CA[G]CG[A]G[A]TG[A]C[C]CT[C]A[C]C[A]AC[C][A][C] | SEQ ID NO: 7 |
| T[T]T[T]TCUCC[A]G[C][G][A]GAUGA[C]CCUCA[C][C][A]A[C][C]ACU | SEQ ID NO: 8 |
| A[C]AC[T]CT[T]TC[C]CT[A]C[A]CGA[C]GC[T]CTT[C]CGATCT | SEQ ID NO: 9 |
| G[T]G[A]C[T]G[G]AG[T]TC[A]GACG[T]GTGC[T]C[T]TCCG[A]TCT | SEQ ID NO: 10 |
| G[T]G[A]C[T]G[G]AG[T]TC[A]GACG[T]GTGC[T]C[T]TCCG[A][T][C] | SEQ ID NO: 11 |
| CA[G]CG[A]GATG[A]CCCT[C]A[C]CAAC[C][A][C] | SEQ ID NO: 12 |
| CA[G]CG[A]GATG[A]CCCT[C]A[C]CA[A]C[C][A][C] | SEQ ID NO: 13 |
| CA[G]CG[A]GATG[A]C[C]CT[C]A[C]CA[A]C[C][A][C] | SEQ ID NO: 14 |
| CA[G]CG[A]G[A]TG[A]C[C]CT[C]A[C]CA[A]C[C][A][C] | SEQ ID NO: 15 |
| CA[G]CG[A]GATG[A]CCCT[C]A[C]C[A]AC[C][A][C] | SEQ ID NO: 16 |
| CA[G]CG[A]GATG[A]C[C]CT[C]A[C]C[A]AC[C][A][C] | SEQ ID NO: 17 |
| CA[G]CG[A]G[A]TG[A]C[C]CT[C]A[C]C[A]AC[C][A][C] | SEQ ID NO: 18 |

TABLE 1-continued

Invasion primer sequences, from 5'-3', wherein the nucleotide contained in brackets indicates an LNA nucleotide.

| Nucleotide Sequence 5' to 3' | SEQ ID number |
|---|---|
| C[A]G[C][G][A]GAUGA[C]CCUCA[C][C][A]A[C][C]ACU | SEQ ID NO: 19 |
| [T]TC[C]CT[A]C[A]CGA[C]GC[T]CTT[C]CGATCT | SEQ ID NO: 20 |
| AG[T]TC[A]GACG[T]GTGC[T]C[T]TCCG[A]TCT | SEQ ID NO: 21 |
| AG[T]TC[A]GACG[T]GTGC[T]C[T]TCCG[A][T][C] | SEQ ID NO: 22 |
| T[T]T[T]T[C]T[C]CA[G]CG[A]GATG | SEQ ID NO: 23 |
| TTT[T]T[C]T[C]CA[G]CG[A]GATG | SEQ ID NO: 24 |
| TTTTT[C]T[C]CA[G]CG[A]GATG | SEQ ID NO: 25 |
| TTTTTCT[C]CA[G]CG[A]G[A]TG | SEQ ID NO: 26 |
| T[T]T[T]T[C]T[C]CA[G]CG[A]GATG | SEQ ID NO: 27 |
| T[T]T[T]T[C]T[C]CA[G]CG[A]GATG | SEQ ID NO: 28 |
| T[T]T[T]T[C]T[C]CA[G]CG[A]G[A]TG | SEQ ID NO: 29 |
| T[T]T[T]TCUCC[A][C][G][A]GAUG | SEQ ID NO: 30 |
| A[C]AC [T]CT[T]TC[C]CT[A]C [A] | SEQ ID NO: 31 |
| G[T]G[A]C[T]G[G]AG[T]TC[A] | SEQ ID NO: 32 |
| G[T]G[A]C[T]G[G]AG[T]TC[A] | SEQ ID NO: 33 |
| AATGATACGGCGACCACCG | SEQ ID NO: 34 |
| CAAGCAGAAGACGGCATACGAGAT | SEQ ID NO: 35 |
| CGGTGGTCGCCGTATCATT | SEQ ID NO: 36 |
| ATCTCGTATGCCGTCTTCTGCTTG | SEQ ID NO: 37 |
| [T]T[T]T[C]T[C]CA[G]CG[A]GATG[A]CCCT[C]A[C]CAAC[C][A][C] | SEQ ID NO: 38 |
| [T]T[C]T[C]CA[G]CG[A]GATG[A]CCCT[C]A[C]CA[A][C][C][A][C] | SEQ ID NO: 39 |
| [C]T[C]CA[G]CG[A]GATG[A]C[C]CT[C]A[C]CA[A][C][C][A][C] | SEQ ID NO: 40 |
| [C]CA[G]CG[A]G[A]TG[A]C[C]CT[C]A[C]CA[A][C][C][A][C] | SEQ ID NO: 41 |
| [T]T[T]T[C]T[C]CA[G]CG[A]GATG[A]CCCT[C]A[C]C[A]AC[C][A][C] | SEQ ID NO: 42 |
| [T]T[T]T[C]T[C]CA[G]CG[A]GATG[A]C[C]CT[C]A[C]C[A]AC[C][A][C] | SEQ ID NO: 43 |
| [T]T[T]T[C]T[C]CA[G]CG[A]G[A]TG[A]C[C]CT[C]A[C]C[A]AC[C][A][C] | SEQ ID NO: 44 |
| AATGATAC[G]GCG[A]CCACC[G] | SEQ ID NO: 45 |
| AA[T]GA[T]ACGGC[G]ACCAC[C][G] | SEQ ID NO: 46 |
| [A]AU[G]AUA[C]GG[C]GACC[A]C[C]G | SEQ ID NO: 47 |
| CAAGCAGAAGACGGCATACGAGA[T] | SEQ ID NO: 48 |
| CAAG[C]AGA[A]G[A]CGGCATACG[A]GAT | SEQ ID NO: 49 |
| TCA[A]GCAGA[A]GACGGCA[T][A][C]GA[G]A[T] | SEQ ID NO: 50 |
| T[T]CA[A][G]CAGAAGA[C]GGCAUACGA[G][A]U | SEQ ID NO: 51 |
| CGGTGGTCGCCGTATCA[T][T] | SEQ ID NO: 52 |
| C[G]GT[G]GUCGCC[G]TAUCAUU | SEQ ID NO: 53 |
| TT[T]CGGT[G]GT[C]GCCGTATCA[T][T] | SEQ ID NO: 54 |
| [C]G[G]TGGUCGCCG[T]ATCA[T]T | SEQ ID NO: 55 |

TABLE 1-continued

Invasion primer sequences, from 5'-3', wherein the nucleotide contained in brackets indicates an LNA nucleotide.

| Nucleotide Sequence 5' to 3' | SEQ ID number |
| --- | --- |
| A[T]CT[C]GT[A]TGCC[G]TCT[T]CTGCTT[G] | SEQ ID NO: 56 |
| ATC[T]CGTATGCCGTCTTCTGCT[T][G] | SEQ ID NO: 57 |
| ATCTC[G]TA[T]GC[C]GT[C]TTC[T]GC[T]T[G] | SEQ ID NO: 58 |
| ATC[T]CGUAUGC[C]GTCTUTCUGCUU[G] | SEQ ID NO: 59 |

In embodiments, the invasion primer includes one or more morpholino nucleic acids. Morpholino nucleic acids are synthetic nucleotides that have standard nucleic acid bases (e.g., adenine, guanine, cytosine, and thymine) wherein those bases are bound to methylenemorpholine rings linked through phosphorodiamidate groups instead of phosphates. Morpholino nucleic acids may be referred to as phosphorodiamidate morpholino oligomers (PMOs).

In embodiments, the invasion primer includes locked nucleic acids (LNAs). In embodiments, the invasion primer includes LNAs dispersed throughout the primer, wherein about 2 to 5 nucleotides on the 3' end are canonical dNTPs. In embodiments, the entire composition of the invasion primer includes less than 50%, less than 40%, or less than 30% of LNAs.

In embodiments, the invasion primer includes peptide nucleic acids (PNAs). A PNA is a synthetic nucleic acid analogue wherein the nucleobases are arrayed along a neutral N-(2-aminoethyl)-glycine backbone in place of the negatively charged phosphate backbone of canonical DNA. The unique pseudopeptide backbone is considered to be responsible for dramatically altering the interactions of nucleic acids and proteins with PNA. For example resulting in increased thermostability of PNA hybridization with DNA. It is known that PNA hybridization demonstrates a negative salt dependence wherein lower ionic strength results in increased duplex stability (see, for example, De Costa N. T. S. Heemstra J. M. *PLoS One*. 2013; 8:e58670. In embodiments, the invasion primer includes one or more PNAs and anneals to the dsDNA (e.g., the second strand) in a buffer containing less than 200 nM NaCl, less than about 100 nM NaCl, or less than about 50 nM NaCl.

In embodiments, the invasion primer includes a plurality of LNAs interspersed throughout the polynucleotide. In embodiments, the invasion primer includes a plurality of consecutive LNAs (e.g., 2 to 5 LNAs, 5 to 7 LNAs, or 7 to 10 LNAs) throughout the polynucleotide. In embodiments, the entire composition of the invasion primer includes less than 70%, less than 60%, less than 50%, less than 40%, less than 30%, less than 20%, less than 10%, or less than 5% of LNAs. In embodiments, the entire composition of the invasion primer includes up to about 70%, up to about 60%, up to about 50%, up to about 40%, up to about 30%, up to about 20%, up to about 10%, or up to about 5% of LNAs. In embodiments, the entire composition of the invasion primer includes more than 60%, more than 50%, more than 40%, more than 30%, more than 20%, more than 10%, or more than 5% of LNAs. In embodiments, the entire composition of the invasion primer includes about 5% to about 10%, about 10% to about 20%, about 20% to about 30%, about 30% to about 40%, about 40% to about 50%, about 50% to about 60%, or about 60% to about 70% of LNAs. In embodiments, the entire composition of the invasion primer includes about 5%, about 10%, about 15%, about 20%, about 25%, about 30%, about 35%, about 40%, about 45%, about 50%, about 55%, about 60%, about 65%, or about 70% of LNAs. In embodiments, the entire composition of the invasion primer includes about 30%, about 35%, about 40%, about 45%, about 50%, about 55%, about 60%, about 65%, about 70%, about 75%, about 80%, about 85%, about 90%, or about 95% of canonical dNTPs. In embodiments, the entire composition of the invasion primer includes less than 95%, less than 90%, less than 80%, less than 70%, less than 60%, less than 50%, less than 40%, or less than 30% of canonical dNTPs. In embodiments, the entire composition of the invasion primer includes up to about 95%, up to about 90%, up to about 80%, up to about 70%, up to about 60%, up to about 50%, up to about 40%, or up to about 30% of canonical dNTPs. In embodiments, the entire composition of the invasion primer includes more than 90%, more than 80%, more than 70%, more than 60%, more than 50%, more than 40%, or more than 30% of canonical dNTPs.

In embodiments, the invasion primer includes about 70% of LNAs and about 30% of canonical dNTPs. In embodiments, the invasion primer includes about 65% of LNAs and about 35% of canonical dNTPs. In embodiments, the invasion primer includes about 60% of LNAs and about 40% of canonical dNTPs. In embodiments, the invasion primer includes about 55% of LNAs and about 45% of canonical dNTPs. In embodiments, the invasion primer includes about 50% of LNAs and about 50% of canonical dNTPs. In embodiments, the invasion primer includes about 45% of LNAs and about 55% of canonical dNTPs. In embodiments, the invasion primer includes about 40% of LNAs and about 60% of canonical dNTPs. In embodiments, the invasion primer includes about 35% of LNAs and about 65% of canonical dNTPs. In embodiments, the invasion primer includes about 30% of LNAs and about 70% of canonical dNTPs. In embodiments, the invasion primer includes about 25% of LNAs and about 75% of canonical dNTPs. In embodiments, the invasion primer includes about 20% of LNAs and about 80% of canonical dNTPs. In embodiments, the invasion primer includes about 15% of LNAs and about 85% of canonical dNTPs. In embodiments, the invasion primer includes about 10% of LNAs and about 90% of canonical dNTPs. In embodiments, the invasion primer includes about 5% of LNAs and about 95% of canonical dNTPs.

In embodiments, the invasion primer includes one or more dT nucleobases that are replaced with dU nucleobases. In embodiments, the invasion primer includes a plurality of dT nucleobases that are replaced with dU nucleobases. In embodiments, the invasion primer includes all dT nucleobases replaced with dU nucleobases. In embodiments, the one or more dU nucleobases partition the invasion primer into two or more regions of consecutive nucleotides (e.g., a first plurality of consecutive nucleotides and a second plurality of consecutive nucleotides are separated by the one or more dU nucleobases). In embodiments each of the two or more regions of consecutive nucleotides are each about 3 to about 10 nucleotides in length, or about 3 to about 15 nucleotides in length. In embodiments each of the two or more regions of consecutive nucleotides are each about 3 to about 10 nucleotides in length. In embodiments each of the two or more regions of consecutive nucleotides are each about 3 to about 15 nucleotides in length. In embodiments each of the two or more regions of consecutive nucleotides are each at least about 3, 5, 7, 10, 13, or 15 nucleotides in length. In embodiments, each of the two or more regions of consecutive nucleotides is greater than about 15 nucleotides in length. In embodiments, the calculated or predicted melting temperature (Tm) of each of the two or more regions of consecutive nucleotides is about 50° C. to about 75° C. In embodiments, the calculated or predicted melting temperature (Tm) of each of the two or more regions of consecutive nucleotides is about 60° C. to about 75° C. In embodiments, the calculated or predicted melting temperature (Tm) of each of the two or more regions of consecutive nucleotides is about 50° C. to about 65° C. In embodiments, the calculated or predicted melting temperature (Tm) of each of the two or more regions of consecutive nucleotides is less than about 75° C. In embodiments, the calculated or predicted melting temperature (Tm) of each of the two or more regions of consecutive nucleotides is less than about 65° C. In embodiments, the calculated or predicted melting temperature (Tm) of each of the two or more regions of consecutive nucleotides is less than about 60° C. In embodiments, the dU and the LNA nucleotides are not adjacent to each other. In embodiments, the dU and the LNA nucleotides are separated by one or more native nucleotides.

In embodiments, the invasion primer is about 10 to 100 nucleotides in length. In embodiments, the invasion primer is about 15 to about 75 nucleotides in length. In embodiments, the invasion primer is about 25 to about 75 nucleotides in length. In embodiments, the invasion primer is about 15 to about 50 nucleotides in length. In embodiments, the invasion primer is about 10 to about 20 nucleotides in length. In embodiments, the invasion primer is about 10, 11, 12, 13, 14, 15, 16, 17, 18, 19, or about 20 nucleotides in length. In embodiments, the invasion primer is about 20, 21, 22, 23, 24, 25, 26, 27, 28, 29, or about 30 nucleotides in length. In embodiments, the invasion primer is about 30, 31, 32, 33, 34, 35, 36, 37, 38, 39, or about 40 nucleotides in length. In embodiments, the invasion primer is about 40, 41, 42, 43, 44, 45, 46, 47, 48, 49, or about 50 nucleotides in length. In embodiments, the invasion primer is greater than 30 nucleotides in length. In embodiments, the invasion primer is greater than 40 nucleotides in length. In embodiments, the invasion primer is greater than 50 nucleotides in length. In embodiments, the invasion primer is no less than 20 nucleotides. In embodiments, the invasion primer is about 15 to about 35 nucleotides in length. In embodiments, the invasion primer is about 25 to about 35 nucleotides, wherein 12 to 18 nucleotides are LNA nucleotides. In embodiments, the invasion primer is about 25 to about 35 nucleotides, wherein 14 to 16 nucleotides are LNA nucleotides. In embodiments, the invasion primer is about 30 to about 35 nucleotides, wherein 14 to 16 nucleotides are LNA nucleotides. In embodiments, the invasion primer is 30, 31, 32, or 33 nucleotides, wherein 14 to 16 nucleotides are LNA nucleotides.

In embodiments, the calculated or predicted melting temperature (Tm) of the invasion primer is about 70° C. to about 95° C. In embodiments, the calculated or predicted melting temperature (Tm) of the invasion primer is about 80° C. to about 95° C. In embodiments, the calculated or predicted melting temperature (Tm) of the invasion primer is about 85° C. to about 95° C. In embodiments, the calculated or predicted melting temperature (Tm) of the invasion primer is about 85° C. to about 90° C.

Figure 4A:
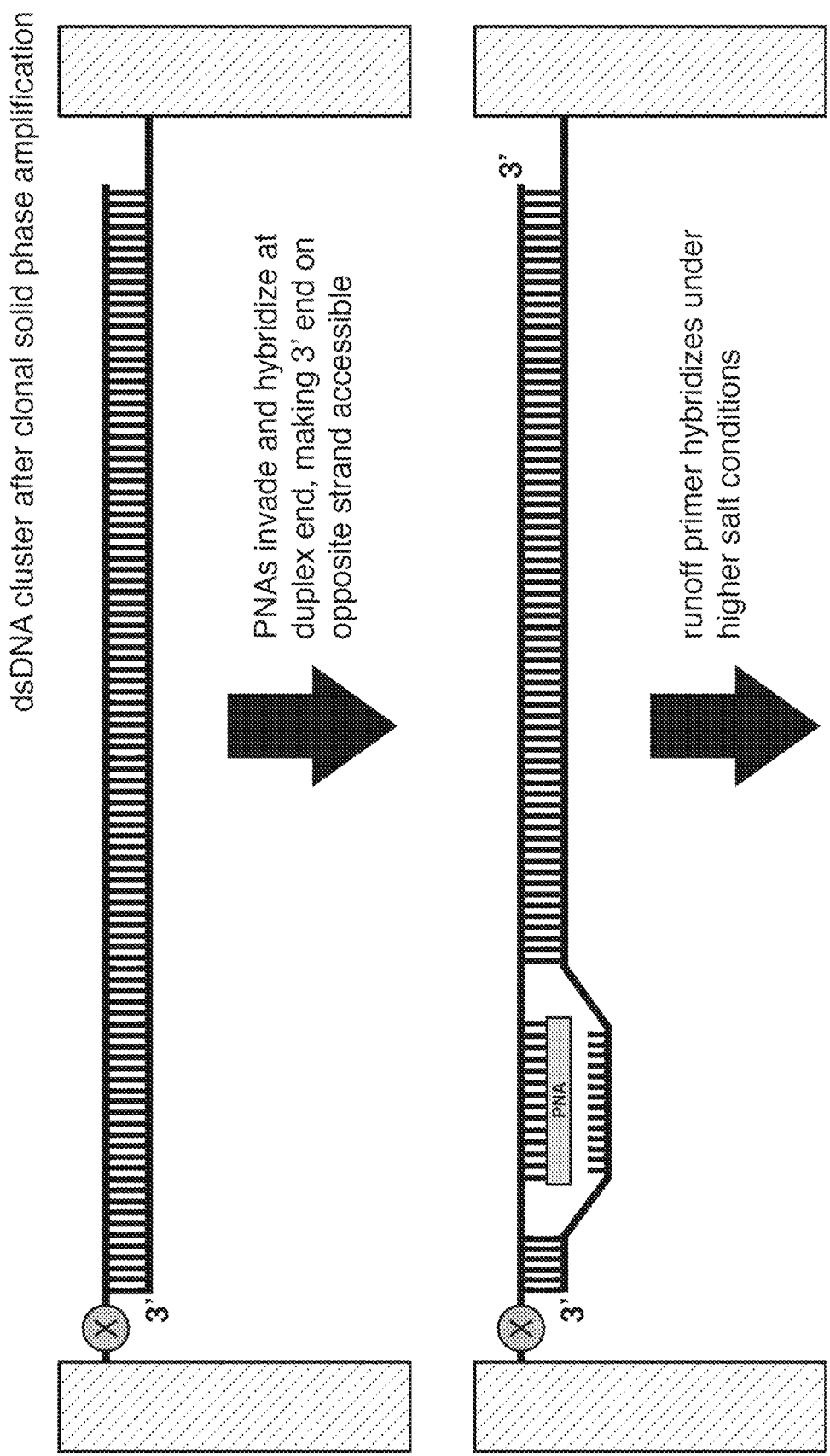
FIGS. 4A-4B illustrate an embodiment of strand invasion using an invasion primer that contains peptide nucleic acids (PNAs) into dsDNA clusters. PNA oligos can invade into dsDNA at low ionic strength (<25 mM NaCl) conditions. As described herein, the PNA-containing invasion primer is designed to invade at the common adapter sequence of the 5' end of one of the solid phase-bound amplicons. This, in turn, makes the displaced complementary 3' DNA end on the complementary strand accessible for binding with another invasion oligonucleotide, referred to as a runoff primer in FIG. 4B, that can be extended by a strand-displacing DNA polymerase. At the end of that process, one of the two strands of the initially dsDNA cluster is now single-stranded and accessible for hybridization with a sequencing primer for a first sequencing read. The sequenced strand may further be cleaved at a cleavable site (represented as 'X') and removed, thus leaving the complementary strand available for sequencing.
Figure 4B:
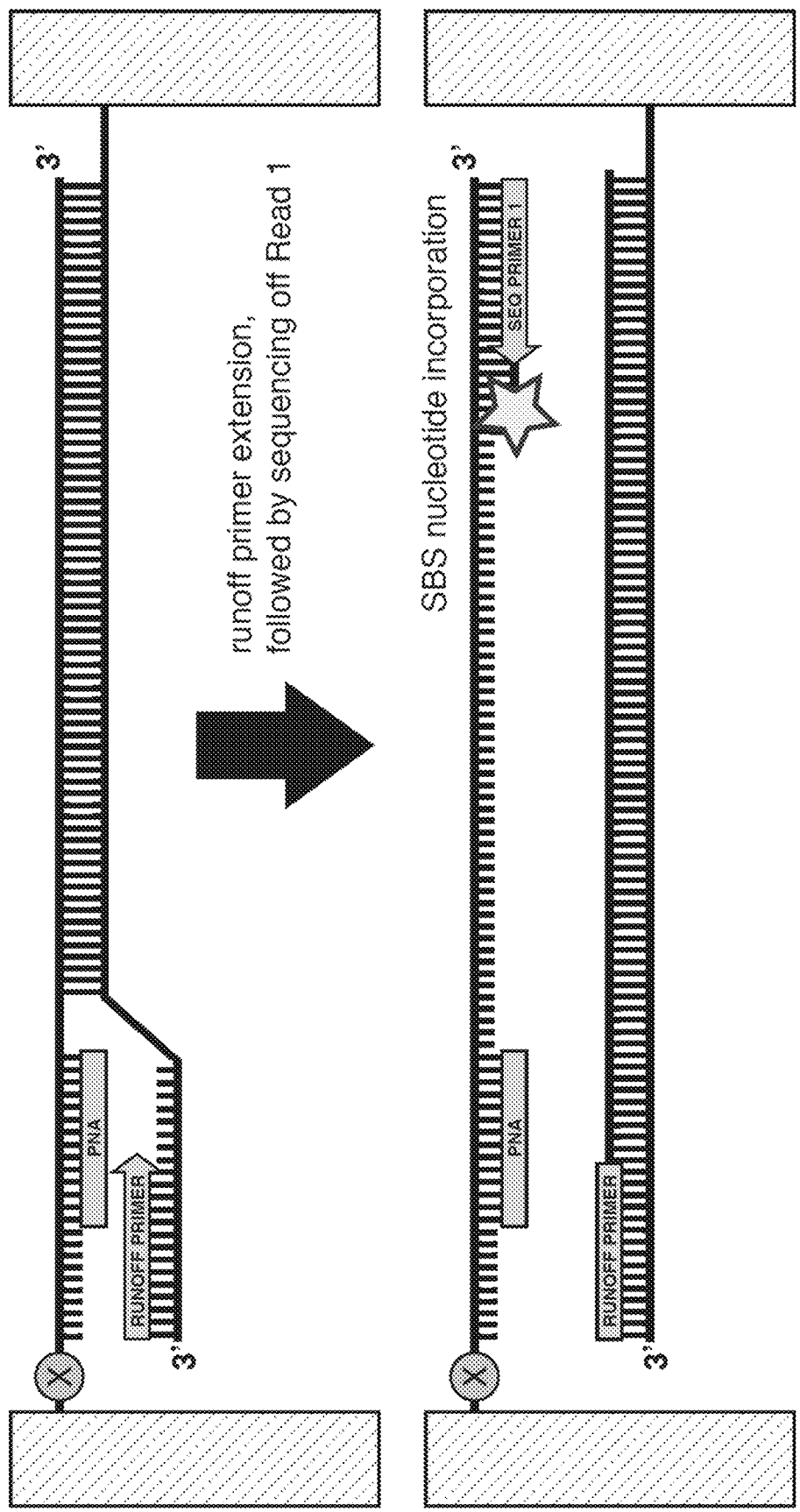

In embodiments, the method includes generating a first invasion strand by hybridizing a first invasion primer (e.g., an invasion primer that includes one or more PNAs or LNAs) to the first strand. In embodiments, the invasion primer does not hybridize at the end of the strand, rather the invasion primer hybridizes about 5 to about 50 nucleotides from the end of the strand. In embodiments, the invasion primer hybridizes about 10 to about 30 nucleotides, about 12 to about 24, or about 15 to about 30 from the end of the strand. The first invasion primer creates a "bubble" in the duplex (e.g., as depicted in FIGS. 4A-4B). A second invasion primer anneals to the second strand (e.g., within the bubble formed by annealing the first invasion primer) and is extended thereby generating a first invasion strand hybridized to the second strand. The first invasion primer may remain during the first sequencing read, or may be removed prior to starting the first sequencing read. In embodiments, the first invasion primer and the second invasion primer are not covalently attached to the solid support.

In embodiments, generating the invasion strand includes a plurality of invasion primer extension cycles, wherein each invasion primer extension cycle includes incorporating one or more nucleotides into the invasion primer. In embodiments, generating the invasion strand includes extending the invasion primer by incorporating one or more nucleotides (e.g., dNTPs) using Bst large fragment (Bst LF) polymerase, Bst2.0 polymerase, Bsu polymerase, SD polymerase, Vent exo-polymerase, Phi29 polymerase, or a mutant thereof. In embodiments, the polymerase extends by incorporating a nucleotide to the 3' end of the invasion primer. In embodiments, the polymerase extends by incorporating a nucleotide to the 3' end of an LNA nucleotide of the invasion primer.

In embodiments, generating the invasion strand includes a plurality of invasion-primer extension cycles by incorporating universal nucleobases (e.g., 5-nitroindole and/or inosine nucleobases) into the invasion primer. The blocking strand does not need to be a faithful representation (i.e., an exact copy) of the strand to which the invasion primer is hybridized. In the interest of speed, in embodiments, one or more inosine nucleotides or "universal" nucleotides may be incorporated into the primer to generate a blocking strand. The term "universal nucleotide," as used herein, refers to a nucleotide analog that is capable of forming a base pair to two or more (e.g., any of the four) natural nucleotide bases (e.g., cytosine (C), guanine (G), adenine (A), or thymine (T)). Thus, any other base may be paired with a universal base analog in a double-stranded polynucleotide. Universal nucleotides may be divided into hydrogen bonding bases and pi-stacking bases. Hydrogen bonding bases form hydrogen bonds with any of the natural nucleobases. The hydrogen bonds formed by hydrogen bonding bases are weaker than the hydrogen bonds between natural nucleobases. Pi-stacking nucleobases are non-hydrogen bonding, hydrophobic, aromatic bases that stabilize duplex polynucleotides by stacking interactions. Examples of hydrogen bonding bases include, but are not limited to, hypoxanthine (inosine), 7-deazahypoxanthine, 2-azahypoxanthine, 2-hydroxypurine, purine, and 4-Amino-1H-pyrazolo [3,4-d]pyrimidine.

Examples of pi-stacking bases include, but are not limited to, nitroimidazole, indole, benzimidazole, 5-fluoroindole, 5-nitroindole, N-indol-5-yl-formamide, isoquinoline, and methylisoquinoline. Examples of universal bases are discussed in Berger et al., Universal Bases for Hybridization, Replication and Chain Termination, Nucleic Acids Research 2000, August 1, 28(15) pp. 2911-2914; David Loakes, The Applications of Universal DNA Base Analogs, 29(12) Nucleic Acids Research 2437 (2001); and Feng Liang et al., Universal base analogs and their applications in DNA sequencing technology, 3 RSC Advances 14910-14928 (2013). In embodiments, the invasion strand includes at least a subset of nucleotides that are not universal nucleotides. In embodiments, at least 1% to 10% of the nucleotides in the invasion strand are universal nucleotides. In embodiments, at least 50% of the nucleotides in the invasion strand are not universal nucleotides.

In embodiments, the blocking strand includes universal nucleobases. In embodiments, the invasion strand is generated using an error-prone polymerase, for example Taq, a Y-family member Dpo4, or others known in the art (e.g., Rattray A J and Strathern J N. Annu Rev Genet. 2003; 37:31-66). In embodiments, the blocking strand is not a copy of the strand the invasion primer is hybridized to. In embodiments, the blocking strand does not replicate the exact sequence of the strand to which the invasion primer is hybridized.

In embodiments, generating the invasion strand includes a first plurality of invasion-primer extension cycles followed by a second plurality of invasion-primer extension cycles, wherein the reaction conditions for the first plurality of invasion-primer extension cycles are different than the second plurality of invasion-primer extension cycles. In embodiments, generating the invasion strand includes alternating between a first plurality of invasion-primer extension cycles and a second plurality of invasion-primer extension cycles, wherein the reaction conditions for the first plurality of invasion-primer extension cycles are different than the second plurality of invasion-primer extension cycles. In embodiments, the reaction conditions for the first plurality of invasion-primer extension cycles include higher stringency hybridization conditions relative to the second plurality of invasion-primer extension cycles.

In embodiments, the reaction conditions for the first plurality of invasion-primer extension cycles include incubation in a first denaturant. In embodiments, the first denaturant includes additives such as ethylene glycol, polyethylene glycol, 1,2-propanediol, dimethyl sulfoxide (DMSO), glycerol, formamide, 7-deaza-dGTP, acetamide, betaine, or tetramethylammonium chloride (TMAC). In embodiments, the first denaturant is a buffered solution including about 0% to about 50% dimethyl sulfoxide (DMSO); about 0% to about 50% ethylene glycol; about 0% to about 20% formamide; or about 0 to about 3M betaine, or a mixture thereof. In embodiments, the reaction conditions for the first plurality of invasion-primer extension cycles include incubation in a first denaturant, wherein the first denaturant is a buffered solution including about 15% to about 50% dimethyl sulfoxide (DMSO); about 15% to about 50% ethylene glycol; about 10% to about 20% formamide; or about 0 to about 3M betaine, or a mixture thereof. In embodiments, the temperature is between 50° C. and about 75° C., inclusive of the endpoints (i.e., the temperature may be 50° C., 52° C., or 75° C., etc.). In embodiments, the temperature is about 50° C. to about 75° C. In embodiments, the temperature is about 55° C. to about 70° C. In embodiments, the temperature is about 60° C. to about 70° C. In embodiments, the temperature is about 55° C. to about 68° C. In embodiments, the buffered solution includes 5×SSC.

In embodiments, the reaction conditions for the second plurality of invasion-primer extension cycles include incubation in a second denaturant. In embodiments, the second denaturant includes additives such as ethylene glycol, polyethylene glycol, 1,2-propanediol, dimethyl sulfoxide (DMSO), glycerol, formamide, 7-deaza-dGTP, acetamide, betaine, or tetramethylammonium chloride (TMAC), wherein the concentrations of the additives in the second denaturant differ than the concentrations of the additives in the first denaturant. In embodiments, the second denaturant is a buffered solution including about 0 to about 50% dimethyl sulfoxide (DMSO); about 0 to about 50% ethylene glycol; about 0 to about 20% formamide; or about 0 to about 3M betaine, or a mixture thereof. In embodiments, the reaction conditions for the second plurality of invasion-primer extension cycles include incubation in a second denaturant, wherein the second denaturant is a buffered solution including about 0% to about 15% dimethyl sulfoxide (DMSO); about 0 to about 15% ethylene glycol; about 0 to about 10% formamide; or about 0 to about 3M betaine, or a mixture thereof. In embodiments, the temperature is between 50° C. and about 75° C., inclusive of the endpoints (i.e., the temperature may be 50° C., 52° C., or 75° C., etc.). In embodiments, the temperature is about 50° C. to about 75° C. In embodiments, the temperature is about 55° C. to about 70° C. In embodiments, the temperature is about 60° C. to about 70° C. In embodiments, the temperature is about 55° C. to about 68° C. In embodiments, the buffered solution includes 5×SSC.

In embodiments, the first denaturant is a buffered solution including dimethyl sulfoxide (DMSO); and the second denaturant is a buffered solution including dimethyl sulfoxide (DMSO) and betaine. In embodiments, the first denaturant is a buffered solution including about 25 to about 35% DMSO; and the second denaturant is a buffered solution including about 0 to about 10% DMSO and about 1M to about 4M betaine. In embodiments, the first denaturant is a buffered solution including about 30% DMSO; and the second denaturant is a buffered solution including about 5% DMSO, about 2.5M betaine.

In embodiments, the reaction conditions for the second plurality of invasion-primer extension cycles further includes incubation with a SSB protein.

In embodiments, generating the invasion strand (e.g., the first invasion strand and/or the second invasion strand) comprises contacting the polynucleotide with one or more invasion-reaction mixtures. In embodiments, generating the invasion strand includes contacting the double-stranded amplification product with one or more invasion-reaction mixtures; each of the invasion-reaction mixture including a plurality of invasion primers, a plurality of deoxyribonucleotide triphosphate (dNTPs), and a polymerase. In embodiments, generating the invasion strand includes contacting the double-stranded amplification product with a first invasion-reaction mixture followed by contacting the double-stranded amplification product with a second invasion-reaction mixture; the first invasion-reaction mixture including a plurality of invasion primers and no polymerase; and the second invasion-reaction mixture includes a plurality of deoxyribonucleotide triphosphate (dNTPs) and a polymerase. In embodiments, the polymerase is a strand-displacing polymerase. In embodiments, the strand-displacing polymerase is Bst large fragment (Bst LF) polymerase, Bst 3.0 polymerase, Bst2.0 polymerase, Bsu polymerase, SD polymerase, Vent exo-polymerase, Phi29 polymerase, or a mutant thereof.

In embodiments, each of the plurality of invasion-reaction mixtures include a plurality of invasion primers, a plurality of deoxyribonucleotide triphosphate (dNTPs), a polymerase, or a combination thereof. In embodiments, each of the plurality of invasion-reaction mixtures include a denaturant, single-stranded DNA binding protein (SSB), or both a denaturant and single-stranded DNA binding protein (SSB). In embodiments, each invasion-reaction mixture further includes a denaturant, single-stranded DNA binding protein (SSB), or a combination thereof. In embodiments, each invasion-reaction mixture includes a different amount of a denaturant, single-stranded DNA binding protein (SSB), or a combination thereof.

In embodiments, the denaturant is a buffered solution including betaine, dimethyl sulfoxide (DMSO), ethylene glycol, formamide, glycerol, guanidine thiocyanate, 4-methylmorpholine 4-oxide (NMO), TMAC, or a mixture thereof. In embodiments, the denaturant is a buffered solution including betaine, dimethyl sulfoxide (DMSO), ethylene glycol, formamide, or a mixture thereof.

In embodiments, each invasion-reaction mixture includes a denaturant including an SSB, a strand-displacing polymerase, and one or more crowding agents. In embodiments, the denaturant does not include a chemical denaturant (e.g., betaine, DMSO, ethylene glycol, formamide, guanidine thiocyanate, NMO, TMAC, or a mixture thereof). In embodiments, the SSB in the denaturant is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB). In embodiments, the strand-displacing polymerase in the denaturant is Bst large fragment (Bst LF) polymerase, Bst 3.0 polymerase, Bst2.0 polymerase, Bsu polymerase, SD polymerase, Vent exo-polymerase, Bsm DNA Polymerase, Phi29 polymerase, or a mutant thereof. In embodiments, the crowding agent in the denaturant is poly (ethylene glycol) (e.g., PEG 200, PEG 600, PEG 800, PEG 2,050, PEG 4,600, PEG 6,000, PEG 8,000, PEG 10,000, PEG 20,000, or PEG 35,000). In embodiments, PEG is present in the denaturant at a concentration of 1% to 25%. In embodiments, PEG is present in the denaturant at a concentration of about 1%, about 5%, about 10%, about 15%, about 20%, or about 25%. In embodiments, the denaturant is a buffered solution including T4 gp32 protein, Bsu polymerase, and 5 to 10% PEG 20,000. In embodiments, the denaturant is a buffered solution including T4 gp32 protein, Bsu polymerase, and 5% PEG 20,000. In embodiments, the denaturant is a buffered solution including T4 gp32 protein, Bsu polymerase, and 10% PEG 20,000.

In embodiments, the SSB is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB). In embodiments, the SSB is active (i.e., has measurable activity) at temperatures less than about 72° C. In embodiments, the SSB is active (i.e., has measurable activity) at temperatures about 72° C. In embodiments, the SSB is active (i.e., has measurable activity) at temperatures greater than about 72° C.

In embodiments, the method further includes contacting the invasion primer with a recombinase, a crowding agent, a loading factor, a single-stranded binding (SSB) protein, or a combination thereof.

In embodiments, generating the invasion strand includes (i) forming a complex including a portion of the double-stranded amplification product, an invasion primer, and a homologous recombination complex including a recombinase, (ii) releasing the recombinase, and (iii) in a primer extension reaction, extending the invasion primer with a strand-displacing polymerase. In embodiments, the strand-displacing polymerase is Bst large fragment (Bst LF) polymerase, Bst 3.0 polymerase, Bst2.0 polymerase, Bsu polymerase, SD polymerase, Vent exo-polymerase, Bsm DNA Polymerase, Phi29 polymerase, or a mutant thereof. In embodiments, the recombinase is a T4 UvsX, RecA, RecT, RecO, or Rad51 protein.

In embodiments, the homologous recombination complex further includes a crowding agent. In embodiments, the crowding agent includes poly(ethylene glycol) (PEG), polyvinylpyrrolidone (PVP), bovine serum albumin (BSA), dextran, Ficoll (e.g., Ficoll 70 or Ficoll 400), glycerol, or a combination thereof. In embodiments, the crowding agent is poly(ethylene glycol) (e.g., PEG 200, PEG 600, PEG 800, PEG 2,050, PEG 4,600, PEG 6,000, PEG 8,000, PEG 10,000, PEG 20,000, or PEG 35,000), dextran sulfate, bovine pancreatic trypsin inhibitor (BPTI), ribonuclease A, lysozyme, O-lactoglobulin, hemoglobin, bovine serum albumin (BSA), or poly(sodium 4-styrene sulfonate) (PSS). In embodiments, the crowding agent is PEG 200, PEG 600, PEG 800, PEG 2,050, PEG 4,600, PEG 6,000, PEG 8,000, PEG 10,000, PEG 20,000, or PEG 35,000. In embodiments, the crowding agent is PEG 10,000, PEG 20,000, or PEG 35,000.

In embodiments, the homologous recombination complex further includes a loading factor, a single-stranded binding (SSB) protein, or both. In embodiments, the homologous recombination complex includes a single-stranded binding (SSB) protein. In embodiments, the SSB protein is T4 gp32 protein, SSB protein, Extreme Thermostable Single-Stranded DNA Binding Protein (ET-SSB), T7 gene 2.5 SSB protein, *Thermococcus kodakarensis* (KOD) SSB, *Thermus thermophilus* (TTH) SSB, *Sulfolobus solfataricus* (SSO) SSB, or phi29 SSB protein.

In embodiments, the homologous recombination complex further includes a loading factor. In embodiments, the loading factor includes a T4 UvsY protein.

In embodiments, generating the invasion strand includes thermally cycling between (i) about 72-80° C. for about 5 seconds to about 30 seconds (referred to as cycle 1); and (ii) about 60-70° C. for about 30 to 90 seconds (referred to as cycle 2). In embodiments, the method includes a plurality of thermal cycles in a periodic order (e.g., cycle type 1, cycle 2, cycle 1, etc.). In embodiments, generating the invasion strand includes thermally cycling between (i) about 67-80° C. for about 5 seconds to about 30 seconds (referred to as cycle 1); and (ii) about 60-70° C. for about 30 to 90 seconds (referred to as cycle 2). In embodiments, the method includes a plurality of thermal cycles in a periodic order (e.g., cycle type 1, cycle 2, cycle 1, etc.).

In embodiments, one or more invasion primers transiently hybridize to the first or second strand. For example, the denaturing conditions in the invasion-reaction mix may be too stringent for the invasion primer to fully and stably hybridize for a significant time, however if a polymerase is present in the invasion-reaction mixture, the polymerase could still extend the invasion primer. In embodiments, generating the first invasion strand includes transient hybridization of one or more invasion primers to the second strand, and extending the one or more invasion strand during their transient hybridization by a polymerase. In embodiments, the invasion primer partially hybridizes (e.g., less than 100% of the invasion primer hybridizes) to the second strand. In embodiments, the invasion primer hybridizes to the second strand and is extended with a polymerase. In embodiments, the invasion primer does not remain fully annealed to the second strand while the polymerase extends the invasion primer. In embodiments, at least three nucleotides of the invasion primer (e.g., the three nucleotides at the 3' end of the invasion primer) hybridize to the second strand, and in the presence of a strand displacing polymerase the 3' end of the invasion primer is extended. In embodiments, about 25% to about 90% of the invasion primer hybridizes to the second strand. In embodiments, about 25%, 30%, 35%, 40%, 45%, 50%, 55%, 60%, 65%, 70%, 75%, 80%, 85%, or about 90% of the invasion primer hybridizes to the second strand.

In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase phototolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase including at least one mutation selected from the group consisting of M8R, V51A, M97T, L123S, G197D, K209E, E221K, E239G, Q497P, K512E, E515A, and F526 (relative to wild type phi29 polymerase).

In embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

In embodiments, the template polynucleotide is about 100 to 1000 nucleotides in length. In embodiments, the template polynucleotide is about 500 to 2000 nucleotides in length. In embodiments, the template polynucleotide is about 1000 to 1000 nucleotides in length. In embodiments, the template polynucleotide is about 50 to 500 nucleotides in length. In embodiments, the template polynucleotide is about 500 to 1000 nucleotides in length. In embodiments, the template polynucleotide is about 350 nucleotides in length. In embodiments, the template polynucleotide is about 10, 20, 50, 100, 150, 200, 300, or 500 nucleotides in length. The template polynucleotide molecules can vary length, such as about 100-300 nucleotides long, about 300-500 nucleotides long, or about 500-1000 nucleotides long. In embodiments, the template polynucleotide molecular is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the template polynucleotide molecule is about 150 nucleotides. In embodiments, the template polynucleotide is about 100-1000 nucleotides long. In embodiments, the template polynucleotide is about 100-300 nucleotides long. In embodiments, the template polynucleotide is about 300-500 nucleotides long. In embodiments, the template polynucleotide is about 500-1000 nucleotides long. In embodiments, the template polynucleotide molecule is about 100 nucleotides. In embodiments, the template polynucleotide molecule is about 300 nucleotides. In embodiments, the template polynucleotide molecule is about 500 nucleotides. In embodiments, the template polynucleotide molecule is about 1000 nucleotides.

In embodiments the template polynucleotide (e.g., genomic template DNA) is first treated to form single-stranded linear fragments (e.g., ranging in length from about 50 to about 600 nucleotides). Treatment typically entails fragmentation, such as by chemical fragmentation, enzymatic fragmentation, or mechanical fragmentation, followed by denaturation to produce single-stranded DNA fragments. In embodiments, the template polynucleotide includes an adapter. The adapter may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length.

In embodiments, the template polynucleotide and the double-stranded amplification products include known adapter sequences on the 5' and 3' ends. In embodiments, the template polynucleotide includes known adapter sequences on the 5' and 3' ends. In embodiments, the double-stranded amplification products include known adapter sequences on the 5' and 3' ends.

In embodiments, prior to hybridizing the invasion primer the method includes amplifying the double-stranded polynucleotides with bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR, or combinations of said methods. In embodiments, generating a double-stranded amplification product includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, generating a double-stranded amplification product includes a bridge polymerase chain reaction amplification. In embodiments, generating a double-stranded amplification product includes a thermal bridge polymerase chain reaction (t-bPCR) amplification. In embodiments, generating a double-stranded amplification product includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions.

In embodiments, the solid support includes a plurality of polynucleotides, wherein each polynucleotide is attached to the solid support at a 5' end of the polynucleotide.

In embodiments, generating a double-stranded amplification product includes amplifying the template polynucleotide or complement thereof on a solid support including a plurality of primers attached to the solid support, wherein the plurality of primers include a plurality of forward primers with complementarity to the template polynucleotide and a plurality of reverse primers with complementarity to a complement of the template polynucleotide, and the amplifying includes a plurality of cycles of strand denaturation, primer hybridization, and primer extension.

In embodiments, the plurality of strand denaturation cycles are different for one or more cycles, wherein the initial denaturation cycle is maintained at different conditions from the remaining denaturation cycles. For example, in embodiments, the initial denaturation cycle is at about 85° C.-95° C. for about 1 minute to about 10 minutes, whereas denaturation in the remaining cycles is different (e.g., about 85° C. for about 15-30 sec). In embodiments, the initial denaturation is maintained at about 85° C.-95° C. for about 5 minutes to about 10 minutes. In embodiments, the initial denaturation is maintained at 90° C.-95° C. for about 1 to 10 minutes. In embodiments, the initial denaturation is maintained at 80° C.-85° C. for about 1 to 10 minutes. In embodiments, the initial denaturation is maintained at 85° C.-90° C. for about 1 to 10 minutes. In embodiments, the initial denaturation is maintained at about 85° C.-95° C. for about 1 minutes to about 10 minutes. In embodiments, the initial denaturation is maintained at about 95° C. for about 5 minutes to about 10 minutes. In embodiments, the initial denaturation is maintained at about 85° C.-95° C. for about 5 minutes to about 10 minutes.

In embodiments, generating a double-stranded amplification product includes a thermal bridge polymerase chain reaction (t-bPCR) amplification. In embodiments, the plurality of cycles includes thermally cycling between (i) about 85° C. for about 15-30 sec for denaturation, and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer.

In embodiments, the plurality of cycles includes thermally cycling between (i) about 80° C. to 90° C. for denaturation, and (ii) about 55° C. to about 65° C. for annealing/extension of the primer. In embodiments, the plurality of cycles includes thermally cycling between (i) about 85° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer. In embodiments, the plurality of cycles includes thermally cycling between (i) less than 80° C. (e.g., 70 to 80° C.) for denaturation, and (ii) about 55° C. to about 65° C. for annealing/extension of the primer. In embodiments, the plurality of cycles includes thermally cycling between (i) about 70° C. for denaturation, and (ii) about 65° C. for annealing/extension of the primer. In embodiments, the plurality of cycles includes thermally cycling between (i) about 75° C. for denaturation, and (ii) about 55° C. for annealing/extension of the primer. In embodiments, the plurality of cycles includes thermally cycling between (i) about 85° C. for denaturation, and (ii) about 65° C. for annealing/extension of the primer.

In embodiments, the plurality of cycles includes thermally cycling between (i) about 85° C. for less than 1 minute for denaturation, and (ii) about 65° C. for about 1 to 2 minutes for annealing/extension of the primer. In embodiments, the plurality of cycles includes thermally cycling between (i) about 85° C. for less than 1 minute for denaturation, and (ii) about 60° C. to about 65° C. for about 1 minute for annealing/extension of the primer. In embodiments, the plurality of cycles includes thermally cycling between (i) about 85° C. for about 15-30 sec for denaturation and (ii) about 65° C. for about 1 minute for annealing/extension of the primer. In embodiments, the plurality of cycles includes thermally cycling between (i) about 85° C. for about 30 sec for denaturation and (ii) about 65° C. for about 1 minute for annealing/extension of the primer. In embodiments, the plurality of cycles includes thermally cycling between (i) about 85° C. for about 15-30 sec for denaturation, and (ii) about 65° C. for about 30 seconds for annealing/extension of the primer. In embodiments, the plurality of cycles includes thermally cycling between (i) about 85° C. for about 15-30 sec for denaturation, and (ii) about 65° C. for about 1 minute for annealing/extension of the primer. In embodiments, the temperature and duration for the annealing of the primer and the extension of the primer are different. In embodiments, the plurality of cycles includes thermally cycling between (i) about 90° C. to 95° C. for about 15 to 30 sec for denaturation and (ii) about 55° C. to about 65° C. for about 30 to 60 seconds for annealing and about 65° C. to 70° C. for about 30 to 60 seconds for extension of the primer. In embodiments, the plurality of denaturation steps is at a temperature of about 80° C.-95° C. In embodiments, the plurality of denaturation steps is at a temperature of about 80° C.-90° C. In embodiments, the plurality of denaturation steps is at a temperature of about 85° C.-90° C. In embodiments, the plurality of denaturation steps is at a temperature of about 81° C., 82° C., 83° C., 84° C., 85° C., 86° C., 87° C., 88° C., 89° C., or about 90° C. In embodiments, the plurality of denaturation steps is at a temperature of about 91° C., 92° C., 93° C., 94° C., 95° C., 96° C., 97° C., 98° C., or about 99° C. In embodiments, the plurality of denaturation steps is at a temperature of about 87° C., 88° C., 89° C., 90° C., 91° C., 92° C., 93° C., 94° C., or about 95° C. In embodiments, the plurality of denaturation steps is at a temperature of about 90° C., 91° C., 92° C., 93° C., 94° C., or about 95° C. In embodiments, the plurality of denaturation steps is at a temperature of about 70° C.-85° C. In embodiments, the plurality of denaturation steps is at a temperature of about 70° C.-80° C. In embodiments, the plurality of denaturation steps is at a temperature of about 75° C.-80° C. In embodiments, the plurality of denaturation steps is at a temperature of about 70° C., 71° C., 72° C., 73° C., 74° C., 75° C., 76° C., 77° C., 78° C., 79° C., or about 80° C. In embodiments, the annealing/extension of the primer cycle is at a temperature of about 55° C., 56° C., 57° C., 58° C., 59° C., 60° C., 61° C., 62° C., 63° C., 64° C., or about 65° C.

In embodiments, amplifying includes incubation in a denaturant. In embodiments, the denaturant is acetic acid, ethylene glycol, hydrochloric acid, nitric acid, formamide, guanidine, sodium salicylate, sodium hydroxide, dimethyl sulfoxide (DMSO), propylene glycol, urea, or a mixture thereof. In embodiments, the denaturant is an additive that lowers a DNA denaturation temperature. In embodiments, the denaturant is betaine, dimethyl sulfoxide (DMSO), ethylene glycol, formamide, glycerol, guanidine thiocyanate, 4-methylmorpholine 4-oxide (NMO), or a mixture thereof. In embodiments, the denaturant is betaine, dimethyl sulfoxide (DMSO), ethylene glycol, formamide, glycerol, guanidine thiocyanate, or 4-methylmorpholine 4-oxide (NMO).

In embodiments, amplifying includes a plurality of cycles of strand denaturation, primer hybridization, and primer extension. Although each cycle will include each of these three events (denaturation, hybridization, and extension), events within a cycle may or may not be discrete. For example, each step may have different reagents and/or reaction conditions (e.g., temperatures). Alternatively, some steps may proceed without a change in reaction conditions. For example, extension may proceed under the same conditions (e.g., same temperature) as hybridization. After extension, the conditions are changed to start a new cycle with a new denaturation step, thereby amplifying the amplicons. Primer extension products from an earlier cycle may serve as templates for a later amplification cycle. In embodiments, the plurality of cycles is about 5 to about 50 cycles. In embodiments, the plurality of cycles is about 10 to about 45 cycles. In embodiments, the plurality of cycles is about 10 to about 20 cycles. In embodiments, the plurality of cycles is about 20 to about 30 cycles. In embodiments, the plurality of cycles is 10 to 45 cycles. In embodiments, the plurality of cycles is 10 to 20 cycles. In embodiments, the plurality of cycles is 20 to 30 cycles. In embodiments, the plurality of cycles is about 10 to about 45 cycles. In embodiments, the plurality of cycles is about 20 to about 30 cycles.

In embodiments, the double-stranded amplification product is provided in a clustered array. In embodiments, the clustered array includes a plurality of double-stranded amplification products localized to discrete sites on a solid support. In embodiments, the solid support is a bead. In embodiments, the solid support is substantially planar. In embodiments, the solid support is contained within a flow cell.

In embodiments, the sequencing includes sequencing-by-synthesis, sequencing-by-binding, sequencing by ligation, or pyrosequencing. In embodiments, generating a first sequencing read or a second sequencing read includes a sequencing by synthesis process. In embodiments, generating a first sequencing read or a second sequencing read includes a sequencing-by-binding. As used herein, "sequencing-by-binding" refers to a sequencing technique wherein specific binding of a polymerase and cognate nucleotide to a primed template nucleic acid molecule (e.g., blocked primed template nucleic acid molecule) is used for identifying the next correct nucleotide to be incorporated into the primer strand of the primed template nucleic acid molecule. The specific binding interaction need not result in chemical incorporation of the nucleotide into the primer. In some embodiments, the specific binding interaction can precede chemical incorporation of the nucleotide into the primer strand or can precede chemical incorporation of an analogous, next correct nucleotide into the primer. Thus, detection of the next correct nucleotide can take place without incorporation of the next correct nucleotide. As used herein, the "next correct nucleotide" (sometimes referred to as the "cognate" nucleotide) is the nucleotide having a base complementary to the base of the next template nucleotide. The next correct nucleotide will hybridize at the 3'-end of a primer to complement the next template nucleotide. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated. In embodiments, the method further includes incorporating one or more unmodified dNTPs or one or more ddNTPs into the 3' end of the extended sequencing primer.

In embodiments, the method includes sequencing the first and/or the second strand of a double-stranded amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and. 6,274,320, each of which is incorporated herein by reference in its entirety). In pyrosequencing, released Ppi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, that are present at features of an array are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738, 072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Non-limiting examples of suitable labels are described in U.S. Pat. Nos. 8,178,360, 5,188,934 (4,7-dichlorofluorscein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthene dyes): U.S. Pat. No. 5,688,648 (energy transfer dyes); and the like.

Sequencing includes, for example, detecting a sequence of signals. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

Flow cells provide a convenient format for housing an array of clusters produced by the methods described herein, in particular when subjected to an SBS or other detection technique that involves repeated delivery of reagents in cycles. For example, to initiate a first SBS cycle, one or more labeled nucleotides and a DNA polymerase in a buffer, can be flowed into/through a flow cell that houses an array of clusters. The clusters of an array where primer extension causes a labeled nucleotide to be incorporated can then be detected. Optionally, the nucleotides can further include a reversible termination moiety that temporarily halts further primer extension once a nucleotide has been added to a primer. For example, a nucleotide analog having a reversible terminator moiety can be added to a primer such that subsequent extension cannot occur until a deblocking agent (e.g., a reducing agent) is delivered to remove the moiety. Thus, for embodiments that use reversible termination, a deblocking reagent (e.g., a reducing agent) can be delivered to the flow cell (before, during, or after detection occurs). Washes can be carried out between the various delivery steps as needed. The cycle can then be repeated N times to extend the primer by N nucleotides, thereby detecting a sequence of length N. Example SBS procedures, fluidic systems and detection platforms that can be readily adapted for use with an array produced by the methods of the present disclosure are described, for example, in Bentley et al., Nature 456: 53-59 (2008), US Patent Publication 2018/0274024, WO 2017/205336, US Patent Publication 2018/0258472, each of which are incorporated herein in their entirety for all purposes.

Use of the sequencing method outlined above is a non-limiting example, as essentially any sequencing methodology which relies on successive incorporation of nucleotides into a polynucleotide chain can be used. Suitable alternative techniques include, for example, pyrosequencing methods, FISSEQ (fluorescent in situ sequencing), MPSS (massively parallel signature sequencing), or sequencing by ligation-based methods.

In embodiments, generating a sequencing read includes determining the identity of the nucleotides in the template polynucleotide (or complement thereof). In embodiments, a sequencing read, e.g., a first sequencing read or a second sequencing read, includes determining the identity of a portion (e.g., 1, 2, 5, 10, 20, 50 nucleotides) of the total template polynucleotide. In embodiments the first sequencing read determines the identity of 5-10 nucleotides and the second sequencing read determines the identity of more than 5-10 nucleotides (e.g., 11 to 200 nucleotides). In embodiments the first sequencing read determines the identity of more than 5-10 nucleotides (e.g., 11 to 200 nucleotides) and the second sequencing read determines the identity of 5-10 nucleotides. In embodiments, following the generation of a sequencing read, subsequent extension is performed using a plurality of standard (e.g., non-modified) dNTPs until the complementary strand is copied. In other embodiments, following the generation of a sequencing read, subsequent extension is performed using a plurality of dideoxy nucleotide triphosphates (ddNTPs) to prevent further extension of the first sequencing read product during a second sequencing read. In embodiments, following the identification of at least 5-10 (e.g., 11 to 200 nucleotides, or up to 1000 nucleotides), subsequent extension is performed using a plurality of standard (e.g., non-modified) dNTPs until the complementary strand is copied. In embodiments, following the identification of at least 5-10 (e.g., 11 to 200 nucleotides, or up to 1000 nucleotides), subsequent extension is performed using a plurality of dideoxy nucleotide triphosphates (ddNTPs) to prevent further extension of the sequencing read product.

In embodiments, following the generation of a first sequencing read, the cleavable site located within the invasion primer is cleaved, thereby exposing a free 5' phosphate in the invasion strand. In embodiments, following the generation of a first sequencing read, the cleavable site located within the invasion primer is cleaved with a cleaving agent, thereby exposing a free 5' phosphate in the invasion strand, and the invasion strand is removed (e.g., enzymatically digested using an exonuclease enzyme). In embodiments, following generation of a first sequencing read, the invasion strand is cleaved at one or more cleavable sites. In embodiments, following cleavage at one or more cleavable sites, the extension product of the invasion primer (i.e., the invasion strand) is removed under suitable non-aggressive conditions (e.g., degraded or denatured under conditions that leave the complementary strand intact, and optionally still hybridized to at least a portion of the invasion primer). In embodiments, the cleavable site is a dU. In embodiments, the cleaving agent includes a glycosylase and one or more suitable endonucleases. In embodiments, cleavage is performed under alkaline (e.g., pH greater than 8) buffer conditions at between 40° C. to 80° C. In embodiments, degradation of the invasion strand is enzymatic degradation. In embodiments, degradation of the invasion strand is accomplished with a 5' to 3' exonuclease. In embodiments, the 5' to 3' exonuclease is lambda exonuclease, or a mutant thereof. In embodiments, following the degradation of the invasion strand, the cleaved invasion primer subsequently initiates a second sequencing read. In embodiments, the second sequencing read is generated without removal of the first sequencing read. In embodiments, the invasion primer (or a portion thereof) is the sequencing primer.

In embodiments, the sequencing method relies on the use of modified nucleotides that can act as reversible reaction terminators. Once the modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. These such reactions can be done in a single experiment if each of the modified nucleotides has attached a different label, known to correspond to the particular base, to facilitate discrimination between the bases added at each incorporation step. Alternatively, a separate reaction may be carried out containing each of the modified nucleotides separately.

In embodiments, the method further includes terminating extension by incorporating one or more unmodified dNTPs and/or one or more ddNTPs into the 3' end of the extension strand and hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand. In embodiments, the method further includes terminating extension by incorporating one or more unmodified dNTPs or one or more ddNTPs into the 3' end of the second extension strand; removing the invasion strand; hybridizing a third sequencing primer to the first strand and incorporating one or more nucleotides into the third sequencing primer with a polymerase to create a third extension strand; and detecting the one or more incorporated nucleotides so as to identify each incorporated nucleotide in said third extension strand. In embodiments, the method includes terminating extension by incorporating one or more unmodified dNTPs or one or more ddNTPs into the 3' end of the third extension strand; and hybridizing a fourth sequencing primer to the first strand and incorporating one or more nucleotides into the fourth sequencing primer with a polymerase to create a fourth extension strand; and detecting the one or more incorporated nucleotides so as to identify each incorporated nucleotide in said fourth extension strand. In embodiments, the method further includes terminating extension by incorporating one or more unmodified dNTPs and/or one or more ddNTPs into the 3' end of the extension strand; hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand; terminating extension by incorporating one or more unmodified dNTPs or one or more ddNTPs into the 3' end of the second extension strand; removing the invasion strand; hybridizing a third sequencing primer to the first strand and incorporating one or more nucleotides into the third sequencing primer with a polymerase to create a third extension strand; and detecting the one or more incorporated nucleotides so as to identify each incorporated nucleotide in said third extension strand; terminating extension by incorporating one or more unmodified dNTPs or one or more ddNTPs into the 3' end of the third extension strand; and hybridizing a fourth sequencing primer to the first strand and incorporating one or more nucleotides into the fourth sequencing primer with a polymerase to create a fourth extension strand; and detecting the one or more incorporated nucleotides so as to identify each incorporated nucleotide in said fourth extension strand.

In embodiments, the method further includes terminating extension by incorporating one or more unmodified dNTPs and/or one or more ddNTPs into the 3' end of the extension strand. In embodiments, the method further includes terminating extension by incorporating one or more unmodified dNTPs. In embodiments, the method further includes terminating extension by incorporating one or more ddNTPs into the 3' end of the extension strand.

In embodiments, the method further includes hybridizing a second sequencing primer to the second strand and incorporating one or more nucleotides (e.g., labeled nucleotides) with a polymerase into the second sequencing primer to create a second extension strand; and detecting the one or more incorporated nucleotides so as to identify each incorporated nucleotide in said second extension strand. In embodiments, the nucleotides are modified nucleotides including a label and a reversible terminator, as described herein.

The modified nucleotides may carry a label (e.g., a fluorescent label) to facilitate their detection. Each nucleotide type may carry a different fluorescent label. However, the detectable label need not be a fluorescent label. Any label can be used which allows the detection of an incorporated nucleotide. One method for detecting fluorescently labeled nucleotides includes using laser light of a wavelength specific for the labeled nucleotides, or the use of other suitable sources of illumination. The fluorescence from the label on the nucleotide may be detected (e.g., by a CCD camera, CMOS camera, or other suitable detection means).

In embodiments, the methods of sequencing a nucleic acid include extending a complementary polynucleotide (e.g., a primer) that is hybridized to the nucleic acid by incorporating a first nucleotide. In embodiments, the method includes a buffer exchange or wash step (e.g., between each sequencing cycle). In embodiments, the methods of sequencing a nucleic acid include a sequencing solution. The sequencing solution includes (a) an adenine nucleotide, or analog thereof, (b) (i) a thymine nucleotide, or analog thereof, or (ii) a uracil nucleotide, or analog thereof, (c) a cytosine nucleotide, or analog thereof, and (d) a guanine nucleotide, or analog thereof.

In certain embodiments, the sequencing methods provided herein comprises sequencing both strands of a double-stranded nucleic acid with an error rate of $5 \times 10^{-5}$ or less, $1\times10^{-5}$ or less, $5\times10^{-6}$ or less, $1\times10^{-6}$ or less, $5\times10^{-7}$ or less, $1\times10^{-7}$ or less, $5\times10^{-8}$ or less, or $1\times10^{-8}$ or less. In certain embodiments, the sequencing methods provided herein comprises sequencing both strands of a double-stranded nucleic acid with an error rate of $5\times10^{-5}$ to $1\times10^{-8}$, $1\times10^{-5}$ to $1\times10^{-8}$, $5\times10^{-5}$ to $1\times10^{-7}$, $1\times10^{-5}$ to $1\times10^{-7}$, $5\times10^{-6}$ to $1\times10^{-8}$, or $1\times10^{-6}$ to $1\times10^{-8}$. In certain embodiments, the sequencing methods provided herein comprises sequencing both strands of a double-stranded nucleic acid with an error rate of $1\times10^{-7}$ to $1\times10^{-8}$.

In an aspect is provided a method of reducing GC bias in a plurality of sequencing reads, the method including sequencing a template polynucleotide to generate a plurality of sequencing reads as described herein. In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing one or more invasion primers to the second strand, as described herein, for example wherein generating the first invasion strand includes a first plurality of invasion-primer extension cycles followed by a second plurality of invasion-primer extension cycles, wherein the reaction conditions for the first plurality of invasion-primer extension cycles are different than the second plurality of invasion-primer extension cycles and extending the one or more invasion primers; generating a first sequencing read by hybridizing one or more sequencing primers to the first strand, and extending the one or more first sequencing primers. In embodiments, the invasion primer is not covalently attached to the solid support.

In embodiments, the method includes: generating a double-stranded amplification product including a first strand hybridized to a second strand, wherein (i) the double-stranded amplification product includes the template polynucleotide or complement thereof, and (ii) the first strand and second strand are both attached to a solid support; generating a first invasion strand hybridized to the second strand by hybridizing one or more invasion primers to the second strand, wherein generating the invasion strand comprises alternating between a first plurality of invasion-primer extension cycles and a second plurality of invasion-primer extension cycles, wherein the reaction conditions for the first plurality of invasion-primer extension cycles are different than the second plurality of invasion-primer extension cycles and extending the one or more invasion primers; generating a first sequencing read by hybridizing one or more sequencing primers to the first strand, and extending the one or more first sequencing primers.

In embodiments, generating the invasion strand includes a first plurality of invasion-primer extension cycles followed by a second plurality of invasion-primer extension cycles, wherein the reaction conditions for the first plurality of invasion-primer extension cycles are different than the second plurality of invasion-primer extension cycles. In embodiments, the method further includes a third plurality of invasion-primer extension cycles, wherein the reaction conditions for the third plurality of invasion-primer extension cycles are optionally different than the first or second plurality of invasion-primer extension cycles. In embodiments, the method further includes a third plurality of invasion-primer extension cycles, wherein the reaction conditions for the third plurality of invasion-primer extension cycles are the same as the first plurality of invasion-primer extension cycles.

In an aspect is provided a method of generating a template for nucleic acid sequencing reaction. In embodiments, the method includes providing a solid support including a plurality of immobilized oligonucleotide primers attached to the solid support via a linker, wherein the plurality of oligonucleotide primers include a plurality of forward primers and a plurality of reverse primers, amplifying a template nucleic acid by using the oligonucleotide primers attached to the solid support to generate a plurality of double-stranded amplification products, each double-stranded amplification product including a first strand hybridized to a second strand, wherein (i) each double-stranded amplification product includes the template polynucleotide or complement thereof, and (ii) the first strand and second strand are both attached to the solid support; and generating a first invasion strand hybridized to the second strand by hybridizing one or more invasion primers to the second strand, and extending the one or more invasion primers; thereby generating a template nucleic acid for a nucleic acid sequencing reaction. In embodiments, the method further includes hybridizing one or more sequencing primers to the first strand. In embodiments, the method includes generating a cluster of ssDNA templates. In embodiments, the invasion primer is not covalently attached to the solid support. In embodiments, the invasion strand is not covalently attached to the solid support.

In another aspect is provided a method including: amplifying a template nucleic acid by contacting the template nucleic acid with a plurality of oligonucleotide primers attached to a solid support to generate a plurality of double-stranded amplification products, each double-stranded amplification product including a first strand hybridized to a second strand, wherein the first strand and second strand are both attached to the solid support; and generating a first invasion strand hybridized to the second strand by hybridizing one or more invasion primers to the second strand, and extending the one or more invasion primers to produce a single-stranded first strand. In embodiments, the invasion primer is not covalently attached to the solid support.

In an aspect is provided a method of removing a polynucleotide hybridized to a first strand, wherein the polynucleotide includes one or more of cleavable sites. In embodiments, the method includes fragmenting a polynucleotide in the presence of a plurality of dsDNA polynucleotides. In embodiments, the method includes contacting the polynucleotide with a cleaving agent thereby fragmenting the polynucleotide and generating two or more fragments. In embodiments, the method includes denaturing the fragments (e.g., contacting the fragments with a chemical denaturant, increasing the temperature, or a combination thereof). In embodiments, the method includes digesting the fragments (e.g., contacting the fragments with one or more exonuclease enzymes). In embodiments, the method includes modulating the temperature to be at or below the calculated or predicted melting temperature (Tm) of the fragments (e.g., about 0° C. to about 65° C.). In embodiments, the method includes modulating the temperature to be at about 50° C. to about 65° C.

In embodiments, the first strand is covalently attached to a solid support. In embodiments, the polynucleotide, alternatively referred to herein as the third polynucleotide and/or the invasion primer, is not attached to a solid support. In embodiments, the first strand is attached to a solid support, wherein the solid support includes a plurality of double-stranded polynucleotides. In embodiments, the first strand is in a colony of double-stranded polynucleotides. In embodiments, the solid support includes a second strand hybridized to a sequenced strand, wherein the sequenced strand includes one or more sequenced nucleotides. In embodiments, the sequenced nucleotides include a scar remnant (e.g., an alkynyl moiety attached to the nucleobase). In embodiments, the nucleotides have the formula:

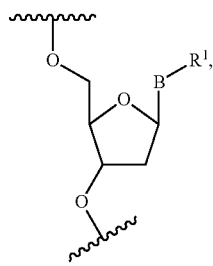

wherein B is a nucleobase, R¹ is the scar remnant, and "|" is the attachment point to the remainder of the sequenced strand polynucleotide.

In embodiments, B is a divalent nucleobase. In embodiments, B is

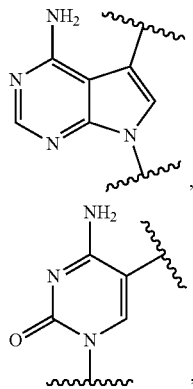, 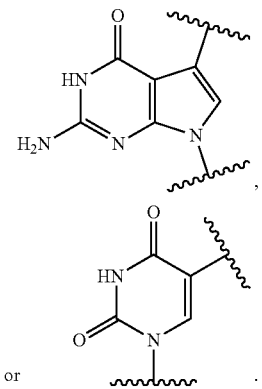.

In embodiments, B is

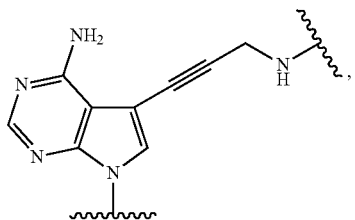

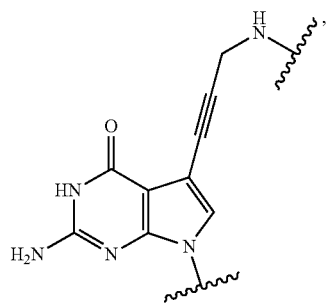

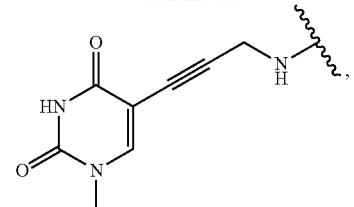

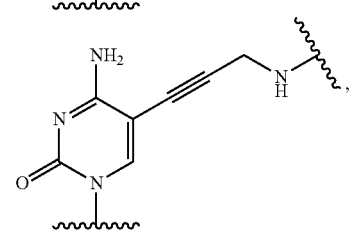

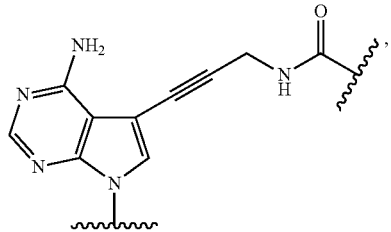

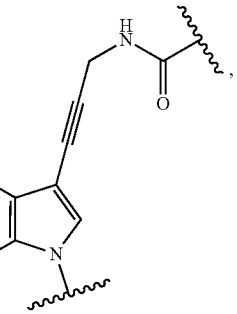

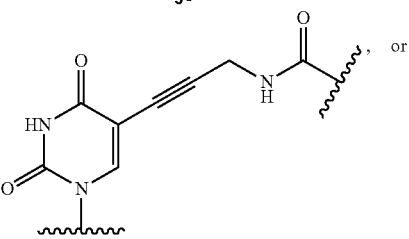

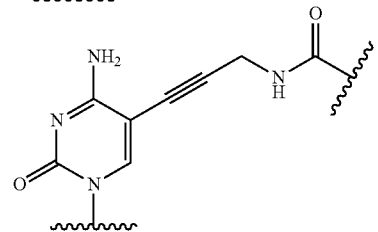

In embodiments, R¹ is hydrogen, —OH, —NH, a substituted or unsubstituted alkyl or substituted or unsubstituted heteroalkyl. In embodiments, R¹ is hydrogen. In embodiments, R¹ is —OH. In embodiments, R¹ is —NH. In embodiments, R¹ is a substituted or unsubstituted alkyl or substituted or unsubstituted heteroalkyl. In embodiments, R¹ is a substituted or unsubstituted alkenyl. In embodiments, R¹ is a substituted or unsubstituted alkynyl. In embodiments, R¹ is a substituted or unsubstituted heteroalkenyl. In embodiments, R¹ is a substituted or unsubstituted heteroalkynyl. In embodiments, $R^1$ is a substituted (e.g., substituted with a substituent group, size-limited substituent group, or lower substituent group) or unsubstituted alkyl or substituted (e.g., substituted with a substituent group, size-limited substituent group, or lower substituent group) or unsubstituted heteroalkyl. In embodiments, $R^1$ is substituted with an oxo or —OH. In embodiments, $R^1$ is substituted with an oxo and —OH.

In embodiments, $R^1$ is an oxo-substituted heteroalkyl (e.g., 2 to 10 membered heteroalkyl, 2 to 8 membered heteroalkyl, or 4 to 8 membered heteroalkyl). In embodiments, $R^1$ is an oxo-substituted heteroalkenyl (e.g., 2 to 10 membered heteroalkenyl, 2 to 8 membered heteroalkenyl, or 4 to 8 membered heteroalkenyl). In embodiments, $R^1$ is an oxo-substituted heteroalkynyl (e.g., 2 to 10 membered heteroalkynyl, 2 to 8 membered heteroalkynyl, or 4 to 8 membered heteroalkynyl). In embodiments, $R^1$ is an oxo-substituted 10 membered heteroalkynyl. In embodiments, $R^1$ is an oxo-substituted 9 membered heteroalkynyl. In embodiments, $R^1$ is an oxo-substituted 8 membered heteroalkynyl. In embodiments, $R^1$ is an oxo-substituted 7 membered heteroalkynyl. In embodiments, $R^1$ is an oxo-substituted 6 membered heteroalkynyl.

In embodiments, the one or more nucleotides including a scar remnant include a nucleobase having the formula

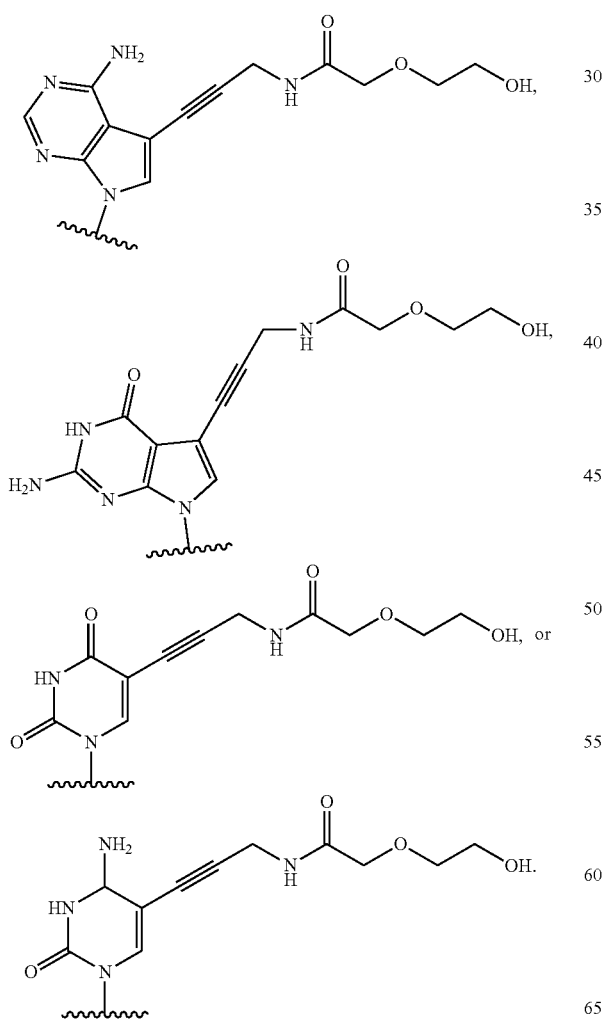

In embodiments, the one or more nucleotides including a scar remnant include a nucleobase having the formula

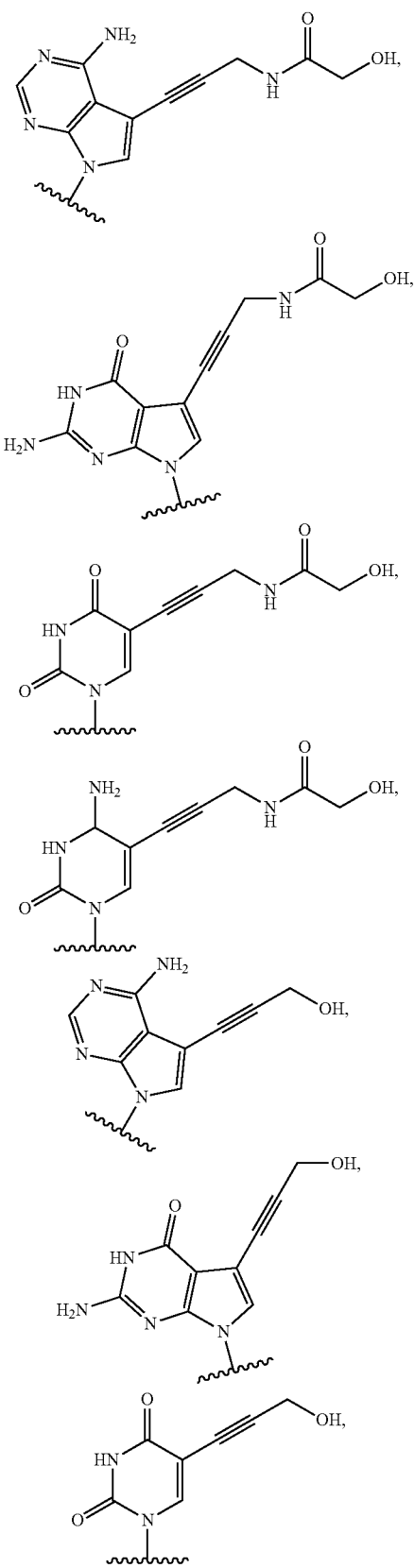

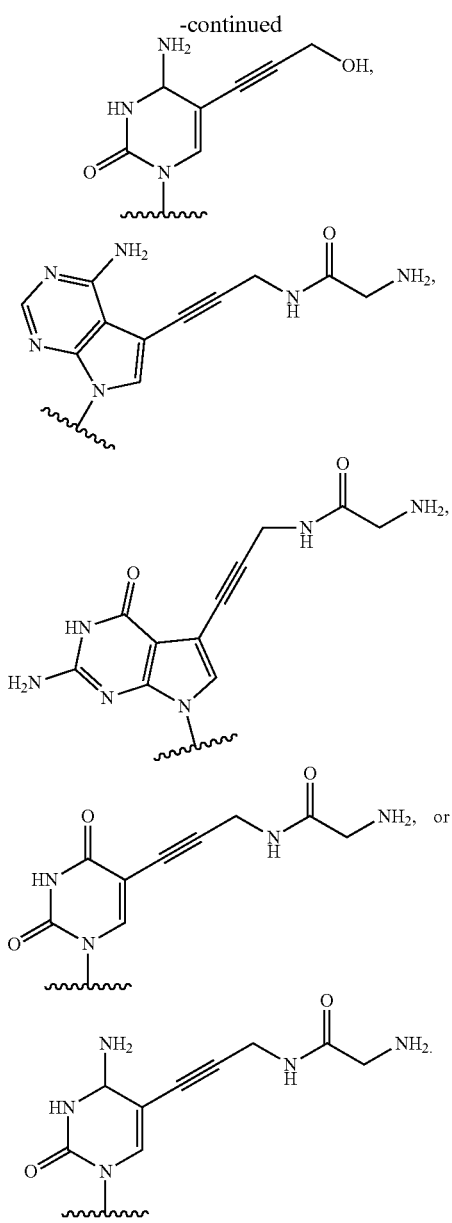

In embodiments, the calculated or predicted melting temperature (Tm) of the fragments is about 50° C. to about 75° C. In embodiments, the calculated or predicted melting temperature (Tm) of the fragments is about 60° C. to about 75° C. In embodiments, the calculated or predicted melting temperature (Tm) of the fragments is about 50° C. to about 65° C. In embodiments, the calculated or predicted melting temperature (Tm) of the fragments is less than about 75° C. In embodiments, the calculated or predicted melting temperature (Tm) of the fragments is less than about 65° C. In embodiments, the calculated or predicted melting temperature (Tm) of the fragments is less than about 60° C. In embodiments, two or more fragments are generated. In embodiments, three or more fragments are generated. In embodiments, four or more fragments are generated. In embodiments, at least three fragments are generated. In embodiments, four fragments are generated.

In embodiments, the fragments are 3-10 nucleotides in length. In embodiments, the fragments are 3-15 nucleotides in length. In embodiments, the fragments are 5 to 20 nucleotides in length. In embodiments, the fragments are 4 to 6 nucleotides in length.

P-EMBODIMENTS

The present disclosure provides the following illustrative embodiments.

Embodiment P1. A method of sequencing a template polynucleotide, the method comprising: (A) generating a double-stranded amplification product comprising a first strand hybridized to a second strand, wherein (i) the double-stranded amplification product comprises the template polynucleotide or complement thereof, and (ii) the first strand and second strand are both attached to a solid support; (B) generating a first invasion strand hybridized to the second strand by hybridizing an invasion primer to the second strand, and extending the invasion primer, wherein the invasion primer is not covalently attached to the solid support; and (C) generating a first sequencing read by hybridizing one or more sequencing primers to the first strand, and extending the one or more first sequencing primers.

Embodiment P2. The method of Embodiment P1, wherein the first strand is covalently attached to the solid support via a first linker and the second strand is covalently attached to the solid support via a second linker.

Embodiment P3. The method of Embodiment P1 or Embodiment P2, further comprising removing the first invasion strand; generating a second invasion strand hybridized to the first strand by hybridizing a second invasion primer to the first strand, and extending the second invasion primer, wherein the second invasion primer is not covalently attached to the solid support; and generating a second sequencing read by hybridizing one or more second sequencing primers to the second strand, and extending the one or more second sequencing primers.

Embodiment P4. The method of Embodiment P1 or Embodiment P2, wherein the invasion primer comprises a cleavable site.

Embodiment P5. The method of Embodiment P4, wherein the cleavable site is located at the 3' end of the invasion primer.

Embodiment P6. The method of Embodiment P4 or Embodiment P5, further comprising cleaving the cleavable site in the invasion primer to generate a free 3' end within the invasion primer, removing the invasion strand, and generating a second sequencing read by extending the invasion primer.

Embodiment P7. The method of Embodiment P1 or Embodiment P2, further comprising removing the first strand by cleaving the first strand at a cleavable site and generating a second sequencing read by hybridizing one or more second sequencing primers to the second strand; and extending the one or more second sequencing primers.

Embodiment P8. The method of Embodiment P7, wherein the first strand comprises at least one cleavable site or the first linker comprises at least one cleavable site.

Embodiment P9. The method of Embodiment P7 or Embodiment P8, wherein cleaving comprises enzymatically cleaving the first strand at the at least one cleavable site.

Embodiment P10. The method of Embodiment P7 or Embodiment P8, wherein cleaving comprises chemically cleaving the first strand at the at least one cleavable site.

Embodiment P11. The method of any one of Embodiment P4 to Embodiment P10, wherein the cleavable site comprises a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

Embodiment P12. The method of any one of Embodiment P4 to Embodiment P10, wherein the cleavable site comprises one or more ribonucleotides.

Embodiment P13. The method of any one of Embodiment P4 to Embodiment P10, wherein the cleavable site comprises deoxyuracil triphosphate (dUTP) or deoxy-8-oxo-guanine triphosphate (d-8-oxoG).

Embodiment P14. The method of any one of Embodiment P4 to Embodiment P10, wherein the first linker comprises a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

Embodiment P15. The method of any one of Embodiment P4 to Embodiment P10, wherein the first strand comprises a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

Embodiment P16. The method of any one of Embodiment P7 to Embodiment P15, wherein cleaving the first strand comprises contacting the cleavable site with a cleaving agent, wherein the cleaving agent comprises a reducing agent, sodium periodate, Rnase, Formamidopyrimidine DNA Glycosylase (Fpg), endonuclease, or uracil DNA glycosylase (UDG).

Embodiment P17. The method of any one of Embodiment P1 to Embodiment P16, wherein the invasion primer comprises locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleotides, or combinations thereof.

Embodiment P18. The method of any one of Embodiment P1 to Embodiment P16, wherein the invasion primer comprises locked nucleic acids (LNAs), Bis-locked nucleic acids (bisLNAs), twisted intercalating nucleic acids (TINAs), bridged nucleic acids (BNAs), peptide nucleic acids (PNAs), or combinations thereof.

Embodiment P19. The method of any one of Embodiment P1 to Embodiment P16, wherein the invasion primer comprises locked nucleic acids (LNAs), or peptide nucleic acids (PNAs).

Embodiment P20. The method of any one of Embodiment P1 to Embodiment P16, wherein generating the first or second invasion strand comprises (i) forming a complex comprising a portion of the double-stranded amplification product, an invasion primer, and a homologous recombination complex comprising a recombinase, (ii) releasing the recombinase, and (iii) in a primer extension reaction, extending the invasion primer with a strand-displacing polymerase.

Embodiment P21. The method of Embodiment P20, wherein the strand-displacing polymerase is Bst large fragment (Bst LF) polymerase, Bst 3.0 polymerase, Bst2.0 polymerase, Bsu polymerase, SD polymerase, Vent exo-polymerase, Phi29 polymerase, or a mutant thereof.

Embodiment P22. The method of Embodiment P20 or Embodiment P21, wherein the recombinase is a T4 UvsX, RecA, RecT, RecO, or Rad51 protein.

Embodiment P23. The method of any one of Embodiment P20 to Embodiment P22, wherein the homologous recombination complex further comprises a crowding agent.

Embodiment P24. The method of Embodiment P23, wherein the crowding agent comprises PEG, PVP, BSA, dextran, Ficoll, glycerol, or a combination thereof.

Embodiment P25. The method of any one of Embodiment P20 to Embodiment P22, wherein the homologous recombination complex further comprises a loading factor, a single-stranded binding (SSB) protein, or both.

Embodiment P26. The method of Embodiment P25, wherein the SSB protein is T4 gp32 protein, SSB protein, Extreme Thermostable Single-Stranded DNA Binding Protein (ET-SSB), T7 gene 2.5 SSB protein, *Thermococcus kodakarensis* (KOD) SSB, *Thermus thermophilus* (TTH) SSB, *Sulfolobus solfataricus* (SSO) SSB, or phi29 SSB protein.

Embodiment P27. The method of Embodiment P25, wherein the loading factor comprises a T4 UvsY protein.

Embodiment P28. The method of any one of Embodiment P1 to Embodiment P27, wherein the invasion primer is about 10 to 100 nucleotides in length.

Embodiment P29. The method of any one of Embodiment P1 to Embodiment P27, wherein the invasion primer is about 15 to about 75 nucleotides in length.

Embodiment P30. The method of any one of Embodiment P1 to Embodiment P27, wherein the invasion primer is about 10 to about 20 nucleotides in length.

Embodiment P31. The method of any one of Embodiment P1 to Embodiment P30, wherein generating the invasion strand comprises a plurality of invasion primer extension cycles.

Embodiment P32. The method of any one of Embodiment P1 to Embodiment P30, wherein generating the invasion strand comprises extending the invasion primer by incorporating one or more nucleotides using Bst large fragment (Bst LF) polymerase, Bst2.0 polymerase, Bsu polymerase, SD polymerase, Vent exo-polymerase, Phi29 polymerase, or a mutant thereof.

Embodiment P33. The method of any one of Embodiment P1 to Embodiment P30, wherein generating the invasion strand comprises contacting the double-stranded amplification product with one or more invasion-reaction mixtures; each of said invasion-reaction mixture comprising a plurality of invasion primers, a plurality of deoxyribonucleotide triphosphate (dNTPs), and a polymerase.

Embodiment P34. The method of Embodiment P33, wherein the polymerase is a strand-displacing polymerase.

Embodiment P35. The method of Embodiment P33, wherein each invasion-reaction mixture further comprises a denaturant, single-stranded DNA binding protein (SSB), or a combination thereof.

Embodiment P36. The method of Embodiment P33, wherein each invasion-reaction mixture comprises a different amount of a denaturant, single-stranded DNA binding protein (SSB), or a combination thereof.

Embodiment P37. The method of Embodiment P35 or Embodiment P36, wherein the denaturant is a buffered solution comprising betaine, dimethyl sulfoxide (DMSO), ethylene glycol, formamide, glycerol, guanidine thiocyanate, 4-methylmorpholine 4-oxide (NMO), or a mixture thereof.

Embodiment P38. The method of Embodiment P35 or Embodiment P36, wherein the denaturant is a buffered solution comprising betaine, dimethyl sulfoxide (DMSO), ethylene glycol, formamide, or a mixture thereof.

Embodiment P39. The method of any one of Embodiment P35 to Embodiment P38, wherein the SSB is T4 gp32 protein, SSB protein, T7 gene 2.5 SSB protein, or phi29 SSB protein, *Thermococcus kodakarensis* (KOD) SSB, *Thermus thermophilus* (TTH) SSB, *Sulfolobus solfataricus* (SSO) SSB, or Extreme Thermostable Single-Stranded DNA Binding Protein (ET-SSB).

Embodiment P40. The method of any one of Embodiment P1 to Embodiment P30, wherein generating the first or second invasion strand comprises a first plurality of invasion-primer extension cycles followed by a second plurality of invasion-primer extension cycles, wherein the reaction conditions for the first plurality of invasion-primer extension cycles are different than the second plurality of invasion-primer extension cycles.

Embodiment P41. The method of any one of Embodiment P1 to Embodiment P30, wherein generating the first or second invasion strand comprises alternating between a first plurality of invasion-primer extension cycles and a second plurality of invasion-primer extension cycles, wherein the reaction conditions for the first plurality of invasion-primer extension cycles are different than the second plurality of invasion-primer extension cycles.

Embodiment P42. The method of Embodiment P40 or Embodiment P41, wherein the reaction conditions for the first plurality of invasion-primer extension cycles comprise higher stringency hybridization conditions relative to the second plurality of invasion-primer extension cycles.

Embodiment P43. The method of Embodiment P40 or Embodiment P41, wherein the reaction conditions for the first plurality of invasion-primer extension cycles comprise incubation in a first denaturant, wherein the first denaturant is a buffered solution comprising about 0% to about 50% dimethyl sulfoxide (DMSO); about 0% to about 50% ethylene glycol; about 0% to about 20% formamide; or about 0 to about 3M betaine, or a mixture thereof.

Embodiment P44. The method of Embodiment P40 or Embodiment P41, wherein the reaction conditions for the first plurality of invasion-primer extension cycles comprise incubation in a first denaturant, wherein the first denaturant is a buffered solution comprising about 15% to about 50% dimethyl sulfoxide (DMSO); about 15% to about 50% ethylene glycol; about 10% to about 20% formamide; or about 0 to about 3M betaine, or a mixture thereof.

Embodiment P45. The method of Embodiment P40 or Embodiment P41, wherein the reaction conditions for the second plurality of invasion-primer extension cycles comprise incubation in a second denaturant, wherein the second denaturant is a buffered solution comprising about 0 to about 50% dimethyl sulfoxide (DMSO); about 0 to about 50% ethylene glycol; about 0 to about 20% formamide; or about 0 to about 3M betaine, or a mixture thereof.

Embodiment P46. The method of Embodiment P40 or Embodiment P41, wherein the reaction conditions for the second plurality of invasion-primer extension cycles comprise incubation in a second denaturant, wherein the second denaturant is a buffered solution comprising about 0% to about 15% dimethyl sulfoxide (DMSO); about 0 to about 15% ethylene glycol; about 0 to about 10% formamide; or about 0 to about 3M betaine, or a mixture thereof.

Embodiment P47. The method of Embodiment P45, wherein the first denaturant is a buffered solution comprising dimethyl sulfoxide (DMSO); and the second denaturant is a buffered solution comprising dimethyl sulfoxide (DMSO) and betaine.

Embodiment P48. The method of Embodiment P45, wherein the first denaturant is a buffered solution comprising about 25 to about 35% DMSO; and the second denaturant is a buffered solution comprising about 0 to about 10% DMSO and about 1M to about 4M betaine.

Embodiment P49. The method of Embodiment P45, wherein the first denaturant is a buffered solution comprising about 30% DMSO; and the second denaturant is a buffered solution comprising about 5% DMSO, about 2.5M betaine.

Embodiment P50. The method of any one of Embodiment P45 to Embodiment P49, wherein the reaction conditions for the second plurality of invasion-primer extension cycles further comprises incubation with a SSB protein.

Embodiment P51. The method of any one of Embodiment P1 to Embodiment P30, wherein generating the first or second invasion strand comprises contacting the double-stranded amplification product with a first invasion-reaction mixture followed by contacting the double-stranded amplification product with a second invasion-reaction mixture; said first invasion-reaction mixture comprising a plurality of invasion primers and no polymerase; and the second invasion-reaction mixture comprises a plurality of deoxyribonucleotide triphosphate (dNTPs) and a polymerase.

Embodiment P52. The method of any one of Embodiment P1 to Embodiment P51, wherein generating the first or second invasion strand comprises thermally cycling between (i) about 67-80° C. for about 5 seconds to about 30 seconds; and (ii) about 60-70° C. for about 30 to 90 seconds.

Embodiment P53. The method of any one of Embodiment P1 to Embodiment P52, wherein the template polynucleotide comprises genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

Embodiment P54. The method of any one of Embodiment P1 to Embodiment P52, wherein the template polynucleotide is about 100 to 1000 nucleotides in length.

Embodiment P55. The method of any one of Embodiment P1 to Embodiment P52, wherein the template polynucleotide is about 350 nucleotides in length.

Embodiment P56. The method of any one of Embodiment P1 to Embodiment P55, wherein the template polynucleotide and the double-stranded amplification product comprise known adapter sequences on the 5' and 3' ends.

Embodiment P57. The method of any one of Embodiment P1 to Embodiment P56, wherein generating a double-stranded amplification product comprises bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of said methods.

Embodiment P58. The method of any one of Embodiment P1 to Embodiment P56, wherein generating a double-stranded amplification product comprises a bridge polymerase chain reaction (bPCR) amplification.

Embodiment P59. The method of any one of Embodiment P1 to Embodiment P56, wherein generating a double-stranded amplification product comprises a thermal bridge polymerase chain reaction (t-bPCR) amplification.

Embodiment P60. The method of any one of Embodiment P1 to Embodiment P56, wherein generating a double-stranded amplification product comprises a chemical bridge polymerase chain reaction (c-bPCR) amplification.

Embodiment P61. The method of any one of Embodiment P1 to Embodiment P56, wherein generating a double-stranded amplification product comprises amplifying the template polynucleotide or complement thereof on a solid support comprising a plurality of primers attached to said solid support, wherein the plurality of primers comprise a plurality of forward primers with complementarity to the template polynucleotide and a plurality of reverse primers with complementarity to a complement of the template polynucleotide, and the amplifying comprises a plurality of cycles of strand denaturation, primer hybridization, and primer extension.

Embodiment P62. The method of Embodiment P61, wherein amplifying comprises incubation in a denaturant.

Embodiment P63. The method of Embodiment P62, wherein the denaturant is acetic acid, ethylene glycol, hydrochloric acid, nitric acid, formamide, guanidine, sodium salicylate, sodium hydroxide, dimethyl sulfoxide (DMSO), propylene glycol, urea, or a mixture thereof.

Embodiment P64. The method of any one of Embodiment P1 to Embodiment P63, wherein the double-stranded amplification product is provided in a clustered array.

Embodiment P65. The method of any one of Embodiment P1 to Embodiment P63, wherein the solid support is a bead.

Embodiment P66. The method of any one of Embodiment P1 to Embodiment P63, wherein the solid support is substantially planar.

Embodiment P67. The method of any one of Embodiment P1 to Embodiment P66, wherein the sequencing comprises sequencing by synthesis, sequencing by ligation, or pyrosequencing.

Embodiment P68. The method of any one of Embodiment P1 to Embodiment P67, wherein generating a first sequencing read or a second sequencing read comprises a sequencing by synthesis process.

Embodiment P69. The method of any one of Embodiment P1 to Embodiment P67, wherein generating a sequencing read comprises executing a plurality of sequencing cycles, each cycle comprising extending the sequencing primer by incorporating a nucleotide or nucleotide analogue using a polymerase and detecting a characteristic signature indicating that the nucleotide or nucleotide analogue has been incorporated.

Embodiment P70. The method of Embodiment P69, further comprising incorporating one or more unmodified dNTPs or one or more ddNTPs into the 3' end of the extended sequencing primer.

Embodiment P71. The method of Embodiment P6, wherein removing the invasion strand comprises digesting the invasion strand using an exonuclease enzyme.

Embodiment P72. The method of Embodiment P6 or Embodiment P71, wherein generating the second sequencing read comprises executing a plurality of sequencing cycles, each cycle comprising extending the invasion primer by incorporating a nucleotide or nucleotide analogue using a polymerase and detecting a characteristic signature indicating that the nucleotide or nucleotide analogue has been incorporated.

Embodiment P73. A substrate comprising: i) a first polynucleotide attached to the substrate; ii) a second polynucleotide attached to the substrate, wherein the second polynucleotide comprises a complementary sequence to the first polynucleotide; and iii) a third polynucleotide hybridized to the second polynucleotide, wherein the third polynucleotide is not covalently attached to the substrate.

Embodiment P74. The substrate of Embodiment P73, wherein the third polynucleotide comprises locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), or combinations thereof.

Embodiment P75. The substrate of Embodiment P73, wherein the third polynucleotide comprises a homologous recombination complex comprising a recombinase bound thereto.

Embodiment P76. The substrate of Embodiment P75, wherein the homologous recombination complex further comprises a loading factor, a single-stranded binding (SSB) protein, or both.

Embodiment P77. The substrate of claim any one of Embodiment P73 to Embodiment P76, further comprising a plurality of immobilized oligonucleotides attached to the substrate via a linker.

Embodiment P78. The substrate of any one of Embodiment P73 to Embodiment P77, wherein the substrate comprises a plurality of first polynucleotides attached to the substrate; a plurality of second polynucleotides attached to the substrate; and a plurality of third polynucleotides hybridized to each of the second polynucleotides, wherein the plurality of third polynucleotides are not covalently attached to the substrate.

Embodiment P79. The substrate of any one of Embodiment P73 to Embodiment P78, wherein the substrate comprises a glass surface comprising a polymer coating.

Embodiment P80. A method of reducing GC bias in a plurality of sequencing reads, said method comprising sequencing a template polynucleotide to generate a plurality of sequencing reads according to Embodiment P42.

Embodiment P81. A method of generating a template for a nucleic acid sequencing reaction, comprising: i) providing a solid support comprising a plurality of immobilized oligonucleotide primers attached to the solid support via a linker, wherein the plurality of oligonucleotide primers comprise a plurality of forward primers and a plurality of reverse primers; ii) amplifying a template nucleic acid by using the oligonucleotide primers attached to the solid support to generate a plurality of double-stranded amplification products, each double-stranded amplification product comprising a first strand hybridized to a second strand, wherein (a) each double-stranded amplification product comprises the template polynucleotide or complement thereof, and (b) the first strand and second strand are both attached to the solid support; and iii) generating a first invasion strand hybridized to the second strand by hybridizing one or more invasion primers to the second strand, and extending the one or more invasion primers, wherein the one or more invasion primers are not covalently attached to the solid support; thereby generating a template nucleic acid for a nucleic acid sequencing reaction.

Embodiment P82. The method of Embodiment P81, further comprising hybridizing one or more sequencing primers to the first strand.

Embodiment P83. A method comprising: i) amplifying a template nucleic acid by using a plurality of oligonucleotide primers attached to a solid support to generate a plurality of double-stranded amplification products, each double-stranded amplification product comprising a first strand hybridized to a second strand, wherein the first strand and second strand are both attached to the solid support; and ii) generating a first invasion strand hybridized to the second strand by hybridizing one or more invasion primers to the second strand, and extending the one or more invasion primers to produce a single-stranded first strand, wherein the one or more invasion primers are not covalently attached to the solid support.

ADDITIONAL EMBODIMENTS

The present disclosure provides the following additional illustrative embodiments.

Embodiment 1. A method of sequencing a double-stranded polynucleotide comprising a first strand hybridized to a second strand, wherein the first strand and second strand are both attached to a solid support, said method comprising: i) hybridizing an invasion primer to the second strand and extending the invasion primer with a polymerase, thereby generating an invasion strand; ii) hybridizing a sequencing primer to the first strand; iii) incorporating one or more nucleotides into the sequencing primer with a polymerase to create an extension strand; and iv) detecting the one or more incorporated nucleotides so as to identify each incorporated nucleotide in said extension strand, thereby sequencing the first strand of the double-stranded polynucleotide.

Embodiment 2. The method of embodiment 1, further comprising removing the first strand, removing the invasion strand, or both removing the first strand and removing the invasion strand.

Embodiment 3. The method of embodiment 1, further comprising removing the invasion strand and hybridizing a second invasion primer to the first strand and extending the second invasion primer with a polymerase, thereby generating a second invasion strand.

Embodiment 4. A method of forming a plurality of single-stranded polynucleotides attached to a solid support, said method comprising: contacting a plurality of double-stranded polynucleotides comprising a first strand hybridized to a second strand with a plurality of invasion primers, wherein the first strand and the second strand are attached to the solid support; hybridizing one or more invasion primers to the second strand; and extending one or more invasion primers hybridized to the second strand with a polymerase to generate one or more invasion strands, displacing the first strand, thereby forming a plurality of single-stranded polynucleotides attached to the solid support.

Embodiment 5. The method of embodiment 4, further comprising sequencing the single-stranded polynucleotides.

Embodiment 6. The method of embodiment 4 or 5, further comprising removing the invasion strand and sequencing the second strand.

Embodiment 7. The method of any one of embodiments 1 to 6, comprising hybridizing a second sequencing primer to the second strand and incorporating one or more nucleotides with a polymerase into the second sequencing primer to create a second extension strand; and detecting the one or more incorporated nucleotides so as to identify each incorporated nucleotide in said second extension strand.

Embodiment 8. The method of embodiment 1, comprising nicking the invasion strand to generate a 3' end and incorporating one or more nucleotides into the 3' end of the invasion primer with a polymerase to create an extension strand; and detecting the one or more incorporated nucleotides so as to identify each incorporated nucleotide in said extension strand.

Embodiment 9. The method of any one of embodiments 2 to 8, wherein removing the invasion strand comprises digesting the invasion strand using an exonuclease enzyme.

Embodiment 10. The method of any one of embodiments 1 to 8, wherein the first strand is covalently attached to the solid support via a first linker and the second strand is covalently attached to the solid support via a second linker.

Embodiment 11. The method of any one of embodiments 1 to 10, wherein the double-stranded polynucleotides comprise known adapter sequences on the 5' and 3' ends.

Embodiment 12. The method of any one of embodiments 1 to 11, wherein the solid support comprises a plurality of polynucleotides, wherein each polynucleotide is attached to the solid support at a 5' end of the polynucleotide.

Embodiment 13. The method of any one of embodiments 1 to 12, wherein the invasion primer comprises locked nucleic acids (LNAs), Bis-locked nucleic acids (bisLNAs), twisted intercalating nucleic acids (TINAs), bridged nucleic acids (BNAs), 2'-O-methyl RNA:DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, or combinations thereof.

Embodiment 14. The method of any one of embodiments 1 to 12, wherein the invasion primer comprises one or more locked nucleic acids (LNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids.

Embodiment 15. The method of any one of embodiments 1 to 14, wherein the invasion primer is about 15 to about 35 nucleotides in length.

Embodiment 16. The method of any one of embodiments 1 to 15, wherein the invasion primer comprises one or more locked nucleic acids (LNAs) at the 3' end of the invasion primer sequence.

Embodiment 17. The method of any one of embodiments 1 to 16, further comprising contacting the invasion primer with a recombinase, a crowding agent, a loading factor, a single-stranded binding (SSB) protein, or a combination thereof.

Embodiment 18. The method of any one of embodiments 1 to 17, wherein generating the invasion strand comprises contacting the polynucleotide with one or more invasion-reaction mixtures.

Embodiment 19. The method of embodiment 18, wherein each of the plurality of invasion-reaction mixtures comprise a plurality of invasion primers, a plurality of deoxyribonucleotide triphosphate (dNTPs), a polymerase, or a combination thereof.

Embodiment 20. The method of embodiment 18 or 19, wherein each of the plurality of invasion-reaction mixtures comprise a denaturant, single-stranded DNA binding protein (SSB), or both a denaturant and single-stranded DNA binding protein (SSB).

Embodiment 21. The method of any one of embodiments 1 to 17, wherein generating the invasion strand comprises a first plurality of invasion-primer extension cycles followed by a second plurality of invasion-primer extension cycles, wherein the reaction conditions for the first plurality of invasion-primer extension cycles are different than the second plurality of invasion-primer extension cycles.

Embodiment 22. The method of embodiment 21, wherein the reaction conditions for the first plurality of invasion-primer extension cycles comprise higher stringency hybridization conditions relative to the second plurality of invasion-primer extension cycles.

Embodiment 23. The method of any one of embodiments 1 to 17, wherein generating the invasion strand comprises contacting the polynucleotide with a buffered solution comprising dimethyl sulfoxide (DMSO), betaine, or a combination of dimethyl sulfoxide (DMSO) and betaine.

Embodiment 24. The method of any one of embodiments 1 to 23, wherein prior to hybridizing the invasion primer the method comprises amplifying the double-stranded polynucleotides with bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR, or combinations of said methods.

Embodiment 25. The method of any one of embodiments 1 to 24, wherein sequencing comprises sequencing by synthesis, sequencing by binding, sequencing by ligation, or pyrosequencing.

Embodiment 26. The method of any one of embodiments 1 to 25, further comprising terminating extension by incorporating one or more unmodified dNTPs or one or more ddNTPs into the 3' end of the extension strand.

Embodiment 27. The method of any one of embodiments 1 to 26, comprising hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand.

Embodiment 28. The method of any one of embodiments 1 to 25, comprising: terminating extension by incorporating one or more unmodified dNTPs or one or more ddNTPs into the 3' end of the extension strand; hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand; terminating extension by incorporating one or more unmodified dNTPs or one or more ddNTPs into the 3' end of the second extension strand; removing the invasion strand; hybridizing a third sequencing primer to the first strand and incorporating one or more nucleotides into the third sequencing primer with a polymerase to create a third extension strand; and detecting the one or more incorporated nucleotides so as to identify each incorporated nucleotide in said third extension strand; terminating extension by incorporating one or more unmodified dNTPs or one or more ddNTPs into the 3' end of the third extension strand; and hybridizing a fourth sequencing primer to the first strand and incorporating one or more nucleotides into the fourth sequencing primer with a polymerase to create a fourth extension strand; and detecting the one or more incorporated nucleotides so as to identify each incorporated nucleotide in said fourth extension strand.

Embodiment 29. A substrate comprising: i) a first polynucleotide attached to the substrate; ii) a second polynucleotide attached to the same substrate, wherein the second polynucleotide comprises a complementary sequence to the first polynucleotide; and iii) a third polynucleotide hybridized to the second polynucleotide, wherein the third polynucleotide is not covalently attached to the substrate.

Embodiment 30. A method of sequencing a template polynucleotide, the method comprising: (A) generating a double-stranded amplification product comprising a first strand hybridized to a second strand, wherein (i) the double-stranded amplification product comprises the template polynucleotide or complement thereof, and (ii) the first strand and second strand are both attached to a solid support; (B) generating a first invasion strand hybridized to the second strand by hybridizing an invasion primer to the second strand, and extending the invasion primer, wherein the invasion primer is not covalently attached to the solid support; and (C) generating a first sequencing read by hybridizing one or more sequencing primers to the first strand, and extending the one or more first sequencing primers.

EXAMPLES

Example 1. An Efficient Approach to Sequencing Two Strands of the Same Polynucleotide Before a target nucleic acid is sequenced, some degree of DNA pre-processing and converting it to a library molecule is typically required. For example, these steps may involve fragmenting input polynucleotides into an appropriate platform-specific size range, followed by an end-polishing step to generate blunt-ended DNA fragments. Common nucleic acid sequences (referred to as adapter sequences) on the 3' and 5' ends are then ligated to these fragments. A functional library molecule typically includes the target molecule with specific adapter sequences added to the 3' and 5' ends, e.g., Illumina's P5 and P7 adapters/primers, to ensure compatibility with the underlying flow cell, so it may be amplified appropriately. For example, typical platform primers include 5'-AATGATACGGCGACCACCG (P5) (SEQ ID NO:34), or the complement thereof, and 5'-CAAGCAGAAGACGG-CATACGA (P7) (SEQ ID NO:60), or the complement thereof. An example of an adapter ligation protocol includes phosphorylated template oligos at the 5' end using a T4 polynucleotide kinase in 1× T4 ligase buffer for 30 minutes at 37° C. in a thermocycler. The kinase is then denatured (e.g., by heating) and the oligo reaction mixture is slowly cooled to 20° C. (e.g., by slowly changing the temperature by 0.1° C. every 2 seconds).

Current SBS platforms require clonal amplification of the initial template library molecules to create clusters (i.e., polonies), each containing 100s to 10,000s of forward and reverse copies of an initial template library molecule, to increase the signal-to-noise ratio because the systems are not sensitive enough to detect the extension of one base at the individual DNA template molecule level. Standard amplification methods employed in commercial sequencing devices (e.g., solid-phase bridge amplification) typically amplify a template using surface immobilized primers to produce a plurality of double-stranded nucleic acid molecules, wherein at least one strand of each double-stranded nucleic acid molecule is attached to the solid support at its 5' ends. A common method of doing solid-phase amplification involves bridge amplification methodologies (referred to as bridge PCR) as exemplified by the disclosures of U.S. Pat. Nos. 5,641,658; 7,115,400; 7,790,418; U.S. Patent Publ. No. 2008/0009420, each of which is incorporated herein by reference in its entirety. In sum, bridge amplification methods allow amplification products (e.g., amplicons) to be immobilized on a solid support in order to form arrays comprised of colonies (or "clusters") of immobilized nucleic acid molecules. Each cluster or colony on such an array is formed from a plurality of identical immobilized polynucleotide strands and a plurality of identical immobilized complementary polynucleotide strands. The products of solid-phase amplification reactions are referred to as "bridged" structures when formed by annealed pairs of immobilized polynucleotide strands and immobilized complementary strands, both strands being immobilized on the solid support at the 5' end, preferably via a covalent attachment. During bridge PCR, additional chemical additives may be included in the reaction mixture, in which the DNA strands are denatured by flowing a denaturant such as formamide or NaOH over the DNA, which chemically denatures complementary strands. This is followed by washing out the denaturant and reintroducing a polymerase in buffer conditions that allow primer annealing and extension.

Sequencing two strands of the sample dsDNA template, referred to as paired-end, paired-strand, linked-strand, or dual-read sequencing, is a powerful technique to improve sequencing accuracy and is commonly performed in next-generation sequencing (NGS) workflows. Sequencing by synthesis (SBS) is a common implementation of NGS and paired-end sequencing is typically performed on monoclonal clusters generated by a clonal amplification process. For example, nucleic acid libraries that have common nucleic acid sequences (referred to as adapter sequences) on the 3' and 5' ends of every library molecule are delivered into a flow cell. Within the flow cell are nucleic acid sequences (referred to as primers) that are complementary to one or both of the adapter sequences of the library molecules. The primers may be immobilized to a solid support (e.g., a flow cell or a bead); a solid support encompasses any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). After hybridization of the adapter region of a library nucleic acid molecule to the immobilized oligonucleotides (i.e., primers) on the solid phase, a polymerase will make an initial copy of the library nucleic acid molecule by extending the primer. The complement of the initial library molecule is now attached to a solid support, and the initial library nucleic acid molecules can either be removed from the flow cell, or can stay present during subsequent steps, depending on which clonal amplification method is used. Next, spatially localized amplification of the initial single seed molecule will occur by means of a solid-phase clonal amplification process. Examples of clonal amplification techniques include, but are not limited to, bridge PCR, solid-phase rolling circle amplification (RCA), solid-phase exponential rolling circle amplification, solid-phase recombinase polymerase amplification (RPA), solid-phase helicase dependent amplification (HDA), template walking amplification, emulsion PCR on particles (beads), or combinations of the aforementioned methods. Optionally, during clonal amplification, additional solution-phase primers can be supplemented in the flow cell for enabling or accelerating amplification.

It is typical for solid-phase clonal amplification to generate monoclonal clusters that each consist of many double-stranded DNA (dsDNA) copies (10s to 100,000s) of the initially seeded library nucleic acid molecule. In SBS workflows, clusters of dsDNA are difficult to sequence effectively with high accuracy and read length, especially as miniaturization pushes the clusters to become more densely arranged on a solid support. To initiate an SBS sequencing reaction, a sequencing primer needs to hybridize to a single-stranded region in the dsDNA and be extended by a polymerase. Individual strands in dsDNA clusters are difficult to access for hybridization of sequencing primers. Additionally, the polymerases used during SBS to incorporate 3' reversibly terminated nucleotides (dNTPs) or native dNTPs (for example in pyrosequencing) typically do not have strand-displacement capabilities, and so even if one is successful in incorporating sequencing primers into dsDNA molecules, it is still challenging to extend said sequencing primers when the vast majority of DNA molecules are in dsDNA format.

Due to these constraints, dsDNA amplicons in clusters are typically processed into single-stranded DNA (ssDNA), sometimes referred to as linearization, by a variety of methods. The dsDNA structures may be linearized by cleavage of one or both strands with a restriction endonuclease or by cleavage of one strand with a nicking endonuclease. Other methods of cleavage can be used as an alternative to restriction enzymes or nicking enzymes, including chemical cleavage (e.g., cleavage of a diol linkage with periodate), cleavage of abasic sites by cleavage with endonuclease, by exposure to heat or alkali, cleavage of ribonucleotides incorporated into amplification products otherwise comprised of deoxyribonucleotides, photochemical cleavage, or cleavage of a peptide linker. Alternatively, the primers may be attached to the solid support with a cleavable linker, such that upon exposure to a cleaving agent, all or a portion of the primer is removed from the surface. For example, one linearization method requires one or both of the immobilized primers to have a cleavable site, such as a uracil, diol, 8-oxoG, disulfide, photocleavable moieties, an RNA base or an endonuclease cleaving site. After the solid phase clonal amplification process is complete, one of the two species of solid phase primers (either forward or reverse) can be cleaved (chemically, enzymatically or optically), followed by a denaturation step to remove the cleaved molecules. This transforms the dsDNA molecules into ssDNA molecules within the cluster and provides a region available for hybridization of a sequencing primer to initiate a sequencing reaction. The monoclonal clusters can proceed to any necessary post-processing steps such as blocking of free 3' ends, removal of select amplicons, or hybridization of a sequencing primer.

In conventional workflows, once ssDNA molecules are generated a first sequencing read is performed by hybridizing a first sequencing primer to a complementary region (e.g., a region within the adapter portion) of the ssDNA molecule. In the presence of an enzyme (e.g., a DNA polymerase), nucleotides (e.g., labeled nucleotides) are incorporated and detected such that the identity of the incorporated nucleotides allows for the identification of the first strand. When the first read is complete (i.e., the first strand is read to a sufficient length with sufficient accuracy) the second strand that was initially cleaved during linearization must be regenerated prior to starting the second read. This can be done by additional amplification steps, such as additional rounds of bridge PCR or another amplification process. Following an additional amplification step after the first sequencing read, the second strand may then be sequenced. All of these steps add complexity and time to the DNA sequencing workflow and can also introduce additional errors made by the polymerase used during solid phase amplification. Highly accurate sequencing methods would greatly benefit from novel methods that bypass the need for additional amplification steps between the two sequencing reads of conventional paired-end sequencing workflows.

In accordance with various embodiments, the methods disclosed herein permit reading of the original first and second strands (e.g., the first and second strand of the amplicons), reducing the time, reagents, expense, and risk of polymerase error inherent in previous methods. Importantly, methods described herein prevent the need for additional solid phase amplification between the two sequencing reads. In embodiments, methods disclosed herein utilize strand invasion using invasion primers into dsDNA amplicons bound to a solid phase, followed by polymerase extension of the invasion primers. Strand invasion into dsDNA can be challenging in general, but can be particularly challenging in dense monoclonal clusters of dsDNA where DNA molecules are packed tightly together in a spatially localized fashion on a solid phase. Because the local concentration of full-length complementary strands is very high, insertion of a traditional primer oligonucleotide is thermodynamically unfavorable.

The invasion primers are oligonucleotide sequences that binds to one strand of the dsDNA molecule in the cluster. For example, the invasion primer may bind to a portion of the common adapter sequence of only the forward, or only the reverse amplicons in clusters. These invasion oligonucleotides may include nucleic acids having a binding affinity higher than the binding affinity of standard or canonical DNA oligonucleotides, such as locked nucleic acids (LNA), peptide nucleic acids (PNAs), 2'-O-methyl RNA:DNA chimeras, minor groove binder probes (MGB), or morpholino probes. The invasion primers are introduced into a flow cell that contains monoclonal dsDNA clusters generated using a known amplification method or an amplification method described herein. Some of these invasion primers can undergo spontaneous strand invasion into dsDNA, as is the case for example for PNA invasion primers under low ionic strength conditions, while other invasion primers may need assistance of additives such as DMSO, ethylene glycol, formamide, betaine, or other denaturants that assist strand invasion by inducing more breathability within dsDNA amplicons. For example, such additives may include a buffered solution containing about 0 to about 50% DMSO, about 0 to about 50% ethylene glycol, about 0 to about 20% formamide, or about 0 to about 3M betaine. In order to achieve sufficient "breathability" within dsDNA amplicons that are bound to a solid phase, it is helpful to include additives that can assist the "fraying" of the dsDNA molecules, particularly at the 5' and 3' ends.

The invasion oligonucleotide can be introduced without a polymerase and allowed to invade and anneal to the complementary region, or it may be introduced together with a polymerase for runoff extension. Examples of polymerases that can be used for runoff extension are strand-displacing polymerases such as Bst large fragment, Bst2.0 (New England Biolabs), Bsm DNA polymerase, Bsu polymerase, SD polymerase, Vent exo-polymerase or Phi29 polymerase. In certain experiments, it is preferable to introduce the invasion oligonucleotide (e.g., a 15-75 bp invasion primer) together with a polymerase in the same reaction mixture. Because of the close physical proximity of the forward and reverse strands of the dsDNA molecules within a cluster, the hybridization of the invasion oligo to one of the DNA strands is often transient, and can be outcompeted easily by the reannealing of the full-length forward and reverse strands of the dsDNA molecules. To efficiently extend the invasion oligos that transiently hybridize, it is useful to have the polymerase within the same reaction mixture such that the polymerase can immediately extend the invasion oligo during the transient hybridizations that occur. For example, we found that particular reaction conditions (30% DMSO and in presence of Bst LF polymerase and dNTPs) can enable efficient invasion and runoff extension of the invasion oligo.

An example of the strand invasion and runoff method outlined above was executed on dsDNA clusters that were generated with bridge PCR. A *Salmonella* genomic dsDNA library with an average library molecule size of approximately 350 bp was generated by using standard library preparation techniques. The dsDNA genomic library was introduced into a proprietary flow cell at a 1 µM concentration in presence of 5×SSC buffer and 30% ethylene glycol. The flow cell was heated to 95° C. to denature the dsDNA library molecules, followed by cooling the flow cell to 45° C. to allow the denatured library molecules to bind to the immobilized primers on the surface of the flow cell. A strand displacing (SD) polymerase (with SD polymerase buffer, 3 mM $MgCl_2$, and 0.2 mM of each dNTP) was subsequently introduced into the flow cell and heated to 60° C. for 10 min to make an initial first copy of the library molecules that were hybridized to the flow cell primers. The initial library molecules were subsequently removed from the flow cell by flushing 0.1M NaOH through the lanes. This was followed by 45 bridge PCR cycles with a Bst LF polymerase and formamide as a chemical denaturant, which were cyclically introduced into the flow cell. A positive control lane was subsequently treated with USER enzyme mix which cleaved the forward amplicons which contained a uracil base and were formed by extending the forward flow cell primers from the flow cell surface. A second lane of the flow cell did not go through cleavage protocols and instead went through a strand invasion and runoff protocol, according to the following steps.

For strand invasion and runoff, dsDNA clusters immobilized in a lane of the flow cell were exposed to a reagent mix that contained a plurality of LNA invasion oligos (at 1 uM concentration) capable of invading and hybridizing to a portion of the common adapter sequence, 0.56 units/uL of Bst polymerase, 30% DMSO, and 0.2 mM of each dNTP. This reaction mix was incubated at 65° C. for 5 min, followed by flowing in fresh reagent mix. A total of four distinct 5 min incubations with fresh invasion-reagent mixtures containing the LNA invasion oligonucleotides, Bst polymerase, DMSO and dNTPs was performed. Subsequently, we probed the 3' end of the ssDNA molecule of the cleaved positive control lane and the single-stranded fragment in the lanes that went through strand invasion and runoff with a FAM-labeled DNA probe. For the strand invasion and runoff conditions, we expect to see fluorescent signal if strand invasion and runoff is successful, since non-treated dsDNA clusters do not allow hybridization of the labeled DNA probe due to inaccessibility of the region to which the FAM-labeled probe would hybridize.

Figure 2A:
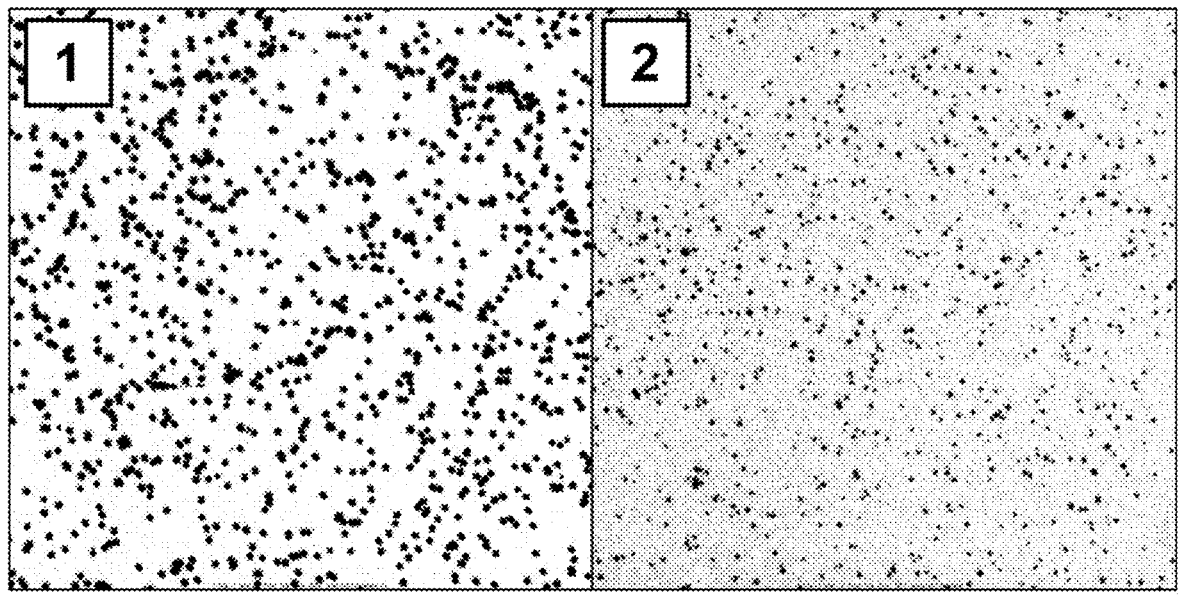
FIGS. 2A-2B show fluorescence images and data showing monoclonal DNA clusters examined under four conditions: 1) non-cleaved, invaded/extended; 2) invasion oligo, no extension; 3) non-cleaved, no invasion/extension; 4) cleaved control.
Figure 2A:
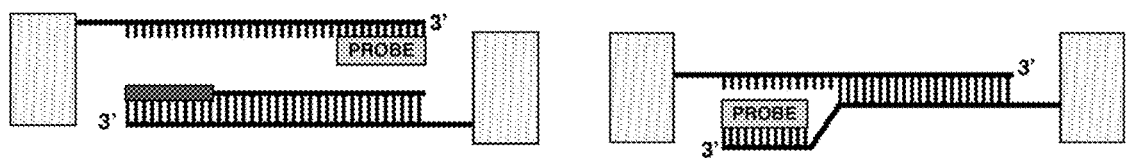
Figure 2A:
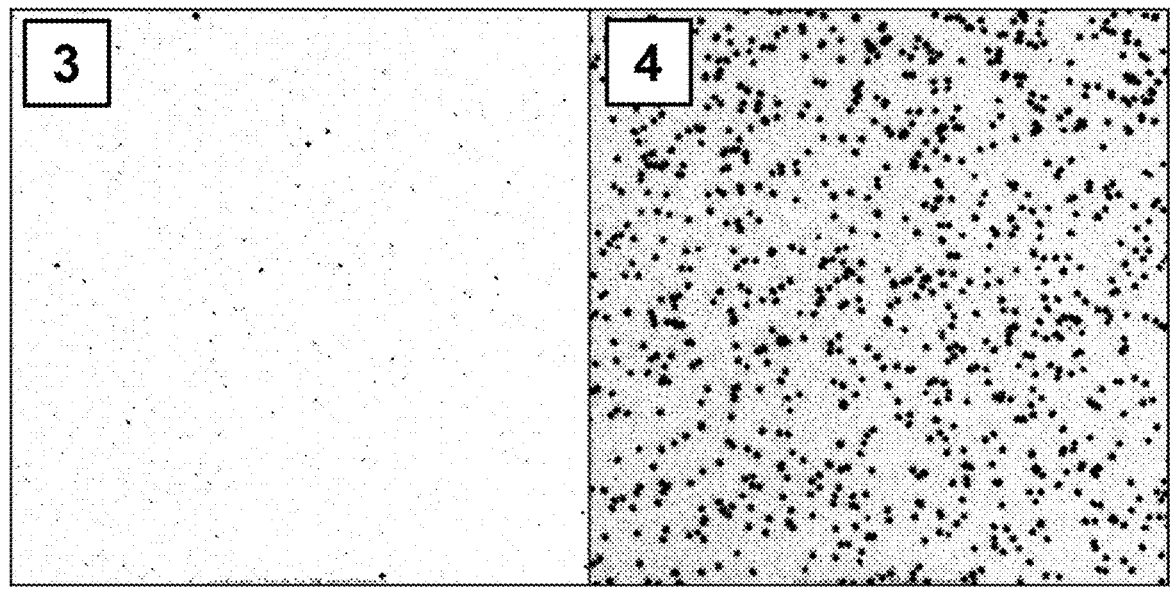
Figure 2A:
Figure 2B:
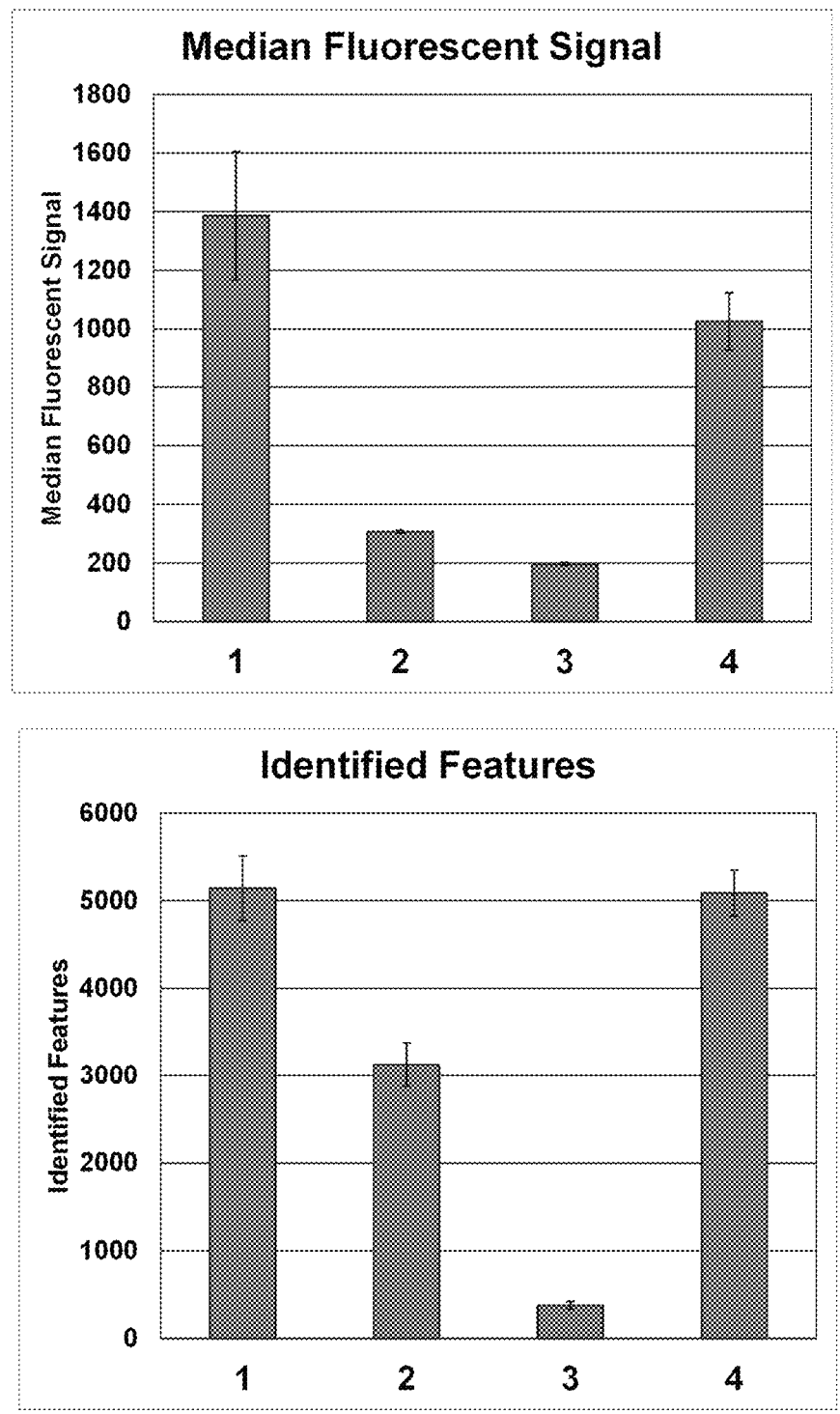

FIG. 2A shows fluorescence images of monoclonal clusters after FAM-probe labeling described above. Together, FIGS. 2A-2B show fluorescence images and data showing monoclonal DNA clusters examined under four conditions: 1) non-cleaved, invaded/extended; 2) invasion oligo, no extension; 3) non-cleaved, no invasion/extension; 4) cleaved control. Condition 4 is a positive control whereby the clusters were converted into ssDNA by cleaving and removing one of the strands from the flow cell surface, followed by labeling the resulting ssDNA molecules with a complementary FAM-labeled DNA probe. Condition 3 is a negative control whereby the amplicon clusters are not subjected to an invasion primer nor extension conditions. Condition 2 reveals that an invasion primer is capable of invading the double-stranded amplification product, but without extension of the invasion primer, the amplicons are not completely accessible to FAM-labeled probes. Condition 1 shows dsDNA clusters that were not cleaved, but were subjected to a method described herein, such as strand invasion and extension, followed by hybridization of a complementary FAM-labeled DNA probe to the liberated ssDNA strand. The probe is only able to hybridize if a complementary single-stranded region is available. Following probe excitation and image acquisition, Condition 1 and condition 4 show the presence of punctate clusters indicative of successful ssDNA formation using the methods described herein. The dsDNA clusters in condition 1 and condition 4 (positive control) show clusters with similar fluorescence intensities and the number of identified features indicating successful probe binding to ssDNA molecules in the monoclonal clusters; see FIG. 2B. For the dsDNA clusters subjected to the strand invasion conditions, the observed fluorescent signals are indicative of successful strand invasion and runoff extension by a polymerase.

As described above, the amplification methods produced clusters of oligonucleotides for sequencing. The initiation point for the first sequencing reaction was provided by annealing a sequencing primer complementary to a region within one of the strands. In the presence of an enzyme (e.g., a DNA polymerase), nucleotides (e.g., labeled nucleotides) are incorporated and detected such that the identity of the incorporated nucleotides allows for the identification of the first strand. Thus, the first sequencing reaction may include hybridizing a sequencing primer to a region of an amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand. Note, the second sequenced strand is present while sequencing the first strand, albeit the second strand it hybridized to the invasion strand.

Figure 3:
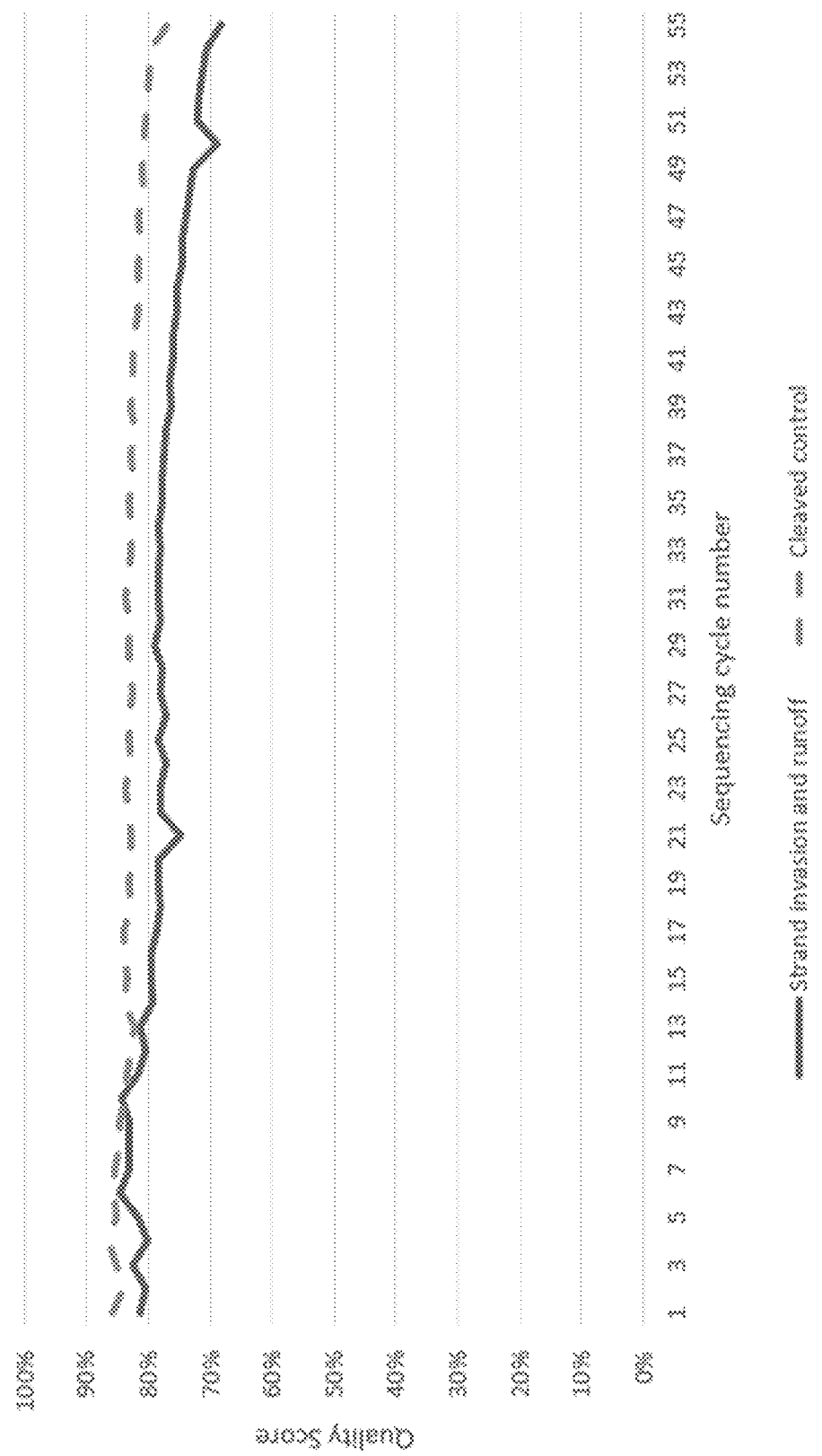
FIG. 3 reports the quality scores for sequencing the positive control Condition 4 (i.e., intentionally formed ssDNA clusters as shown in FIGS. 2A-2B) and for dsDNA clusters subjected to the methods described herein.

The sequencing quality of the above-mentioned conditions were compared to demonstrate the capability of the strand invasion and runoff conditions for generating sequenceable amplicons. To that end, the clusters of the cleaved control conditions and strand invasion/runoff conditions were compared in an SBS experiment. The appropriate sequencing primers were hybridized to the amplicons in lanes with cleaved control and strand invasion/runoff conditions, followed by a plurality of sequencing cycles on a proprietary sequencing instrument. Sequencing quality scores assign confidence to a particular base within a sequencing read by quantifying the probability that a base is called incorrectly. As observed in FIG. 3, the quality scores remained relatively invariant for a plurality of sequencing cycles using the invasion and sequencing methods as described herein. Quality scores were slightly lower for sequencing on dsDNA clusters that went through strand invasion and runoff as compared to sequencing on ssDNA amplicons that were generated by cleaving one of the two amplicons strands. The calculated accuracy for 55 cycles was 99.85% accuracy for the cleaved control condition versus 99.80% for the strand invasion/runoff condition.

Another example and subsequent experiment of the strand invasion and runoff method outlined above was executed on dsDNA clusters that were generated with bridge PCR. In this experiment, following the first sequencing read, the first strand is cleaved and removed prior to sequencing the second strand. A *Salmonella* genomic dsDNA library with an average library molecule size of approximately 350 bp was generated by using standard library preparation techniques. The dsDNA genomic library was introduced into a proprietary flow cell at a 1 pM concentration in presence of 5×SSC buffer and 30% ethylene glycol. The flow cell was heated to 95° C. to denature the dsDNA library molecules, followed by cooling the flow cell to 45° C. to allow the denatured library molecules to bind to the immobilized primers on the surface of the flow cell. A SD polymerase (with SD polymerase buffer, 3 mM $MgCl_2$, and 0.2 mM of each dNTP) was subsequently introduced into the flow cell and heated to 60° C. for 10 min to make an initial first copy of the library molecules that were hybridized to the flow cell primers. The initial library molecules were subsequently removed from the flow cell by flushing 0.1 M NaOH through the lanes. This was followed by 45 bridge PCR cycles with a Bst LF polymerase and formamide as a chemical denaturant, which were cyclically introduced into the flow cell. For strand invasion and runoff, dsDNA clusters in a lane of the flow cell were exposed to a reagent mix that contained a plurality of LNA invasion oligo (at 1 uM concentration) capable of invading and hybridizing to a portion of the common adapter sequence, 0.56 units/uL of Bst polymerase, 30% DMSO, and 0.2 mM of each dNTP. This reaction mix was incubated at 65° C. for 5 min, followed by flowing in a reagent mixture containing LNA invasion oligo (at 1 uM concentration) capable of invading and hybridizing to a portion of the common adapter sequence, 0.56 units/uL of Bst polymerase, 5% DMSO, 2.5M betaine, 25 ng/uL ET-SSB and 0.2 mM of each dNTP. These latter two steps were repeated once more.

Figure 7A:
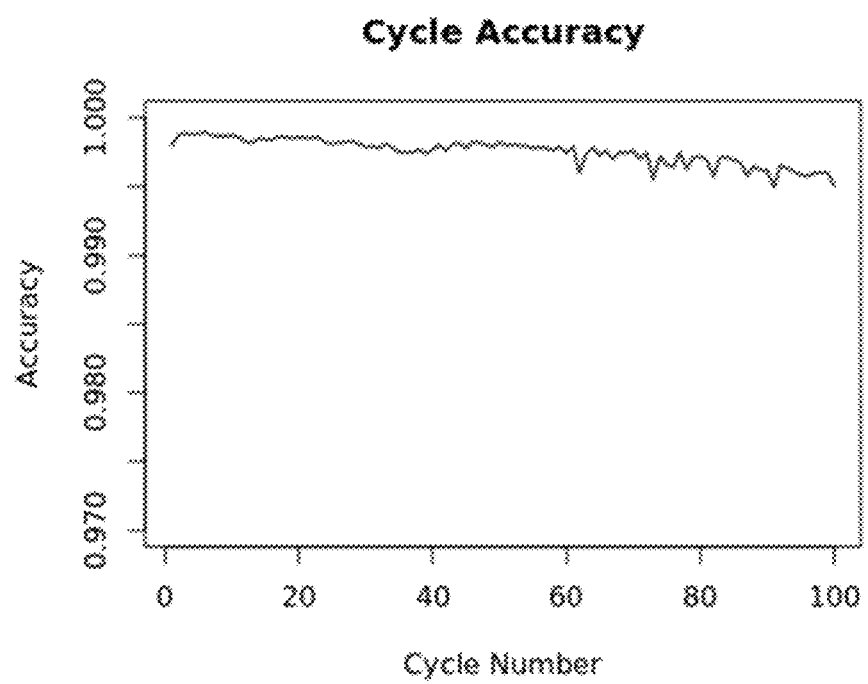
FIGS. 7A-7B are graphs depicting the accuracy per cycle for a first sequencing read (FIG. 7A) and a second sequencing read (FIG. 7B).
Figure 7B:
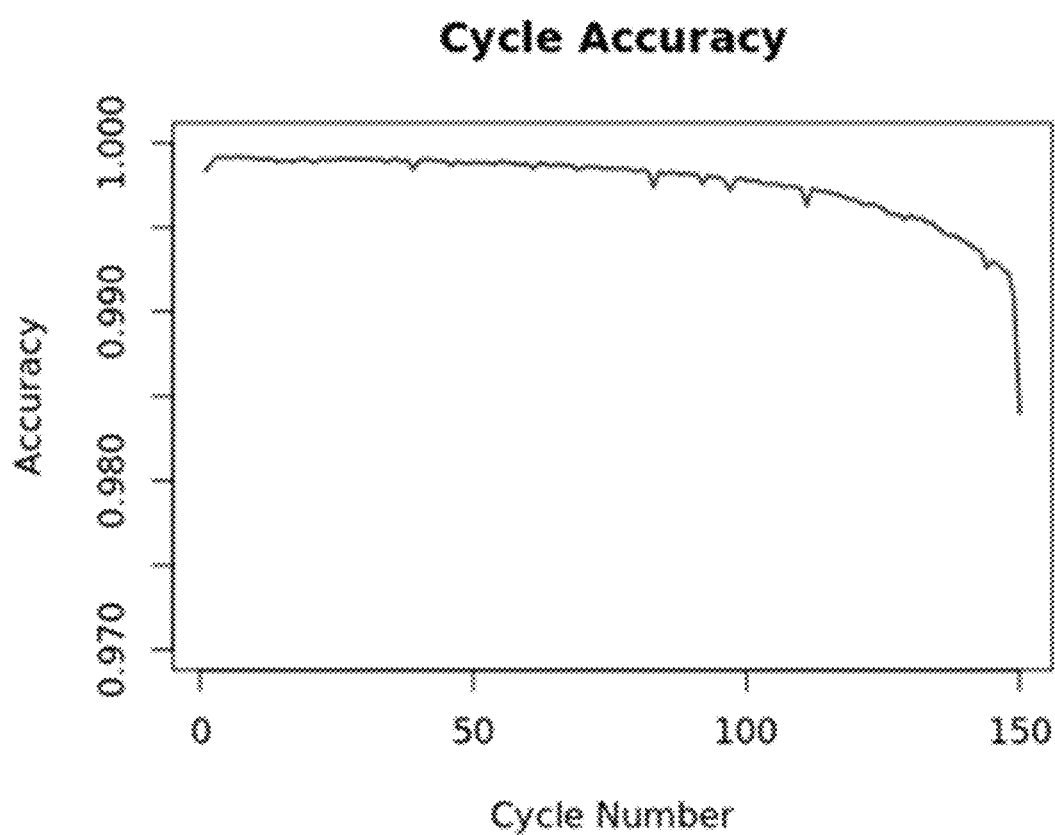

The clusters underwent strand invasion and runoff steps, were hybridized with sequencing primers, and were sequenced for 100 bp to generate a first sequencing read (i.e., a 100 bp sequencing read). This first sequencing read was followed by USER-based cleavage of the strand (i.e., the strand that was sequenced for the first sequencing read is cleaved), and denaturation of the strand together with the invasion/runoff product that was hybridized to the reverse complement of the strand that was sequenced. Next, a second sequencing primer was hybridized to the remaining amplicons on the flow cell surface, followed by a 150 bp second sequencing read. The accuracy of the first sequencing read was 99.756% with 99.3% of the reads mapped to the reference genome. The accuracy of the second sequencing read was 99.767% for the second sequencing read while 99.7% of the reads mapped to the reference genome; see FIGS. 7A-7B. This example shows the capability of obtaining high-quality paired-end sequencing reads with the methodology described herein.

Example 2: PNAs within Invasion Primers

Peptide nucleic acids (PNAs) can be used as invasion oligonucleotides in another example of this invention; see the schematic illustrated in FIGS. 4A-4B. Peptide nucleic acids consist of a pseudopeptide backbone, which has been shown to be capable of invading dsDNA. MiniPEG-γPNAs are particularly beneficial because they have better water solubility (Bahal et al. ChemBioChem, 13(1), 56-60). PNAs typically do not have a 3'-OH that is extendible by a DNA polymerase, though one can consider PNA-DNA chimeras that have 3-7 bp of canonical DNA nucleotides at the 3' end of the oligonucleotide to be extendable by a DNA polymerase. MiniPEG-γPNAs can be designed to invade into dsDNA clusters by targeting a sequence region in the common adapter sequence of all clusters. PNAs can be designed for strand invasion into any part of the common adapter sequences, but targeting near the 5' end of one of the amplicons is beneficial because it renders the complementary strand available for hybridization of another oligonucleotide, as shown in FIG. 4A. A second invasion oligonucleotide that hybridizes on the "liberated" ssDNA fragment opposite of the PNA invasion site can then be extended by a strand-displacing DNA polymerase. As a result, one of the two strands of every dsDNA duplex has now been rendered into a ssDNA fragment that can be sequenced by hybridizing a sequencing primer followed a plurality of sequencing reactions.

Example 3: Recombinase-Assisted Invasion

Figure 5A:
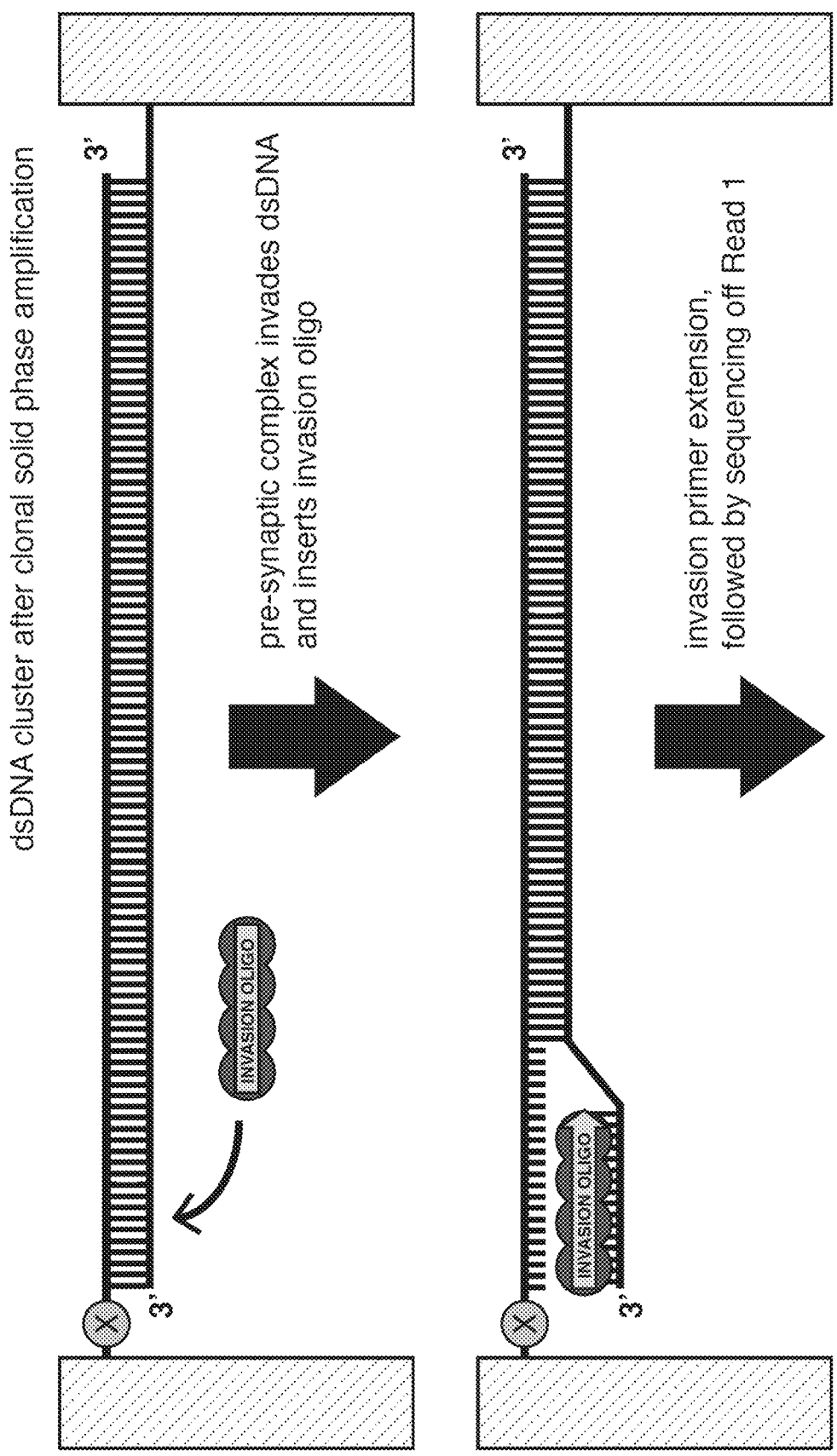
FIGS. 5A-5B illustrate an embodiment of strand invasion into dsDNA monoclonal clusters by using a recombinase and an invasion oligonucleotide. The pre-synaptic filament (alternatively referred to as a pre-synaptic complex), consisting of an invasion oligonucleotide complexed with recombinase enzymes searches dsDNA fragments for homology. The invasion oligonucleotide can be inserted to its complementary sequence in the dsDNA amplicons, after which the invasion oligonucleotide can be extended by a strand-displacing polymerase. This renders one of the two strands of the original dsDNA amplicon available for hybridization of a sequencing primer to initiate the SBS process. The sequenced strand may further be cleaved at a cleavable site (represented as 'X') and removed, thus leaving the complementary strand available for sequencing, as illustrated in FIG. 5B.
Figure 5B:
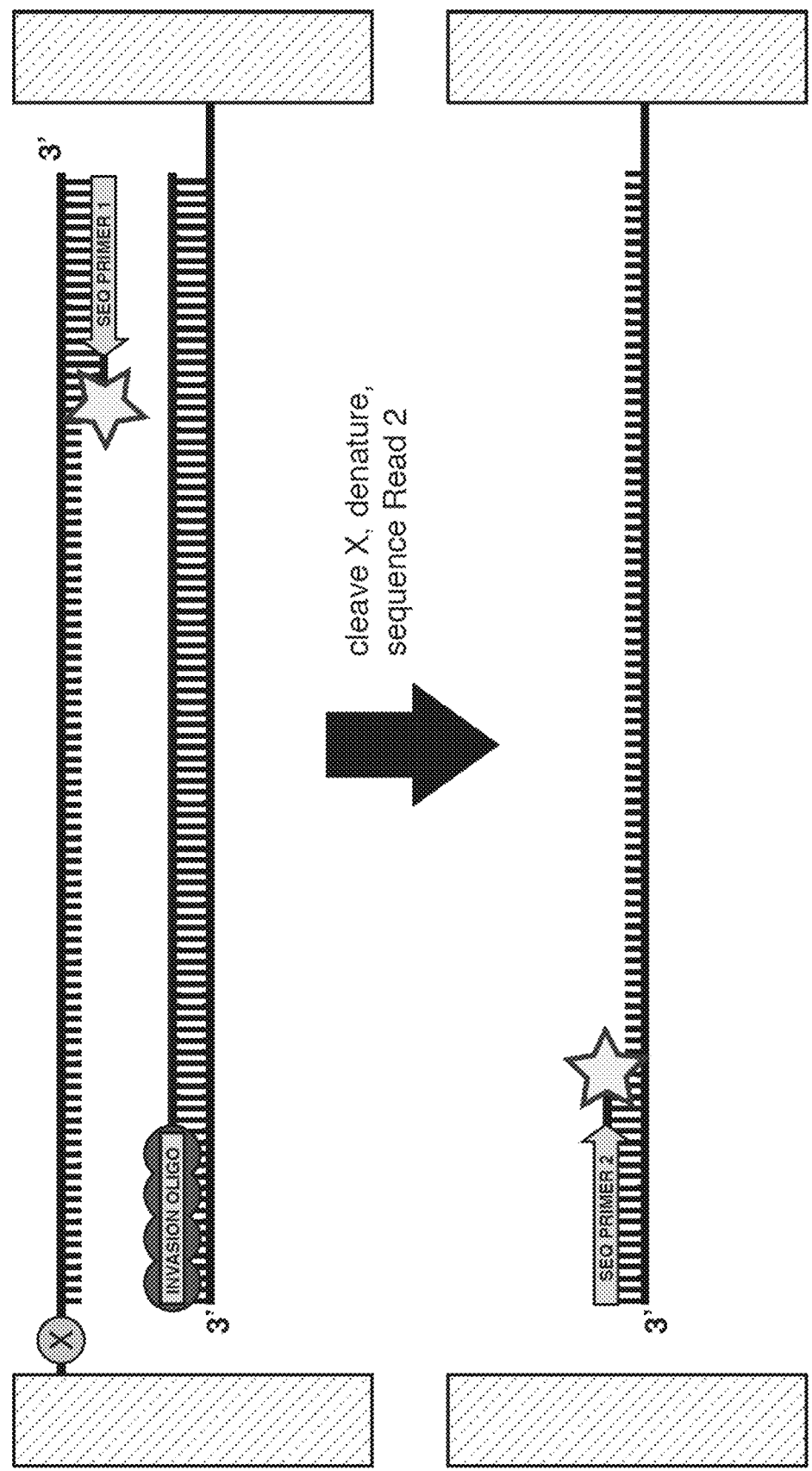

Another possibility for enabling strand invasion into dsDNA molecules in monoclonal clusters is by using a recombinase enzyme that enables the insertion of a DNA oligonucleotide complementary to part of the common adapter sequence; see FIGS. 5A-5B. A reagent mixture consisting of an invasion oligonucleotide, a recombinase, and necessary cofactors for forming a pre-synaptic filament (i.e. an oligonucleotide complexed with recombinase enzymes) is flowed into the flow cell that contains dsDNA clusters. The pre-synaptic filaments search the dsDNA molecules in monoclonal clusters until homology is found, after which the invasion oligonucleotide is inserted into the dsDNA to form a D-loop. After strand invasion, a strand-displacing polymerase can be introduced that extends the invasion oligonucleotide, thereby rendering the opposite strand of the original dsDNA duplex into a single-stranded form. The ssDNA molecule that is generated is then available for hybridization of a sequencing primer and the subsequent start of a first sequencing read. Examples of recombinases include, but are not limited to, T4 UvsX (and possibly its cofactor UvsY, and single-stranded binding protein gp32), Rad51, and RecA. The recombinase can be present in the same reaction mix as the strand-displacing polymerase, or the strand-displacing polymerase can be introduced after strand invasion with the recombinase has been done first.

Example 4. Limiting GC Bias in Sequencing Reads

When generating sequencing reads it is advantageous to obtain as broad a representation of the genome as possible. It is known that PCR amplification can introduce artifacts into sequencing libraries. In addition to nucleotide misincorporation, PCR amplification tends to be uneven, so that some sequence species become overrepresented in the resulting library. This situation is exacerbated by templates with GC-biased compositions. It is well known that extreme base compositions, i.e., GC-poor or GC-rich sequences, lead to uneven coverage or even no coverage of reads across the entirety of genome (see, for example Quail et al. Nat Methods. 2008 December; 5(12):1005-10). For example, read coverage of sequenced regions may be biased depending on the GC content of the library, when it was found the highest read density was found in intervals with elevated GC content (Dohm et al. Nucleic Acids Res. 2008 September; 36(16):e105). This GC bias can be introduced during PCR amplification of the library, cluster amplification, and the sequencing reactions. New experimental designs and optimized amplification protocols have been developed to reduce GC bias, and so it is preferable that sequencing reactions do not introduce any GC bias.

To minimize any GC bias, we discovered that it is beneficial to use at least two distinct invasion-reaction mixtures in order to obtain a recipe that works well for invasion/runoff for a wide range of GC % within the inserts of the sequencing library. For example, invasion/runoff with 30% DMSO may generate runoff extension products that are stable enough to stay hybridized in presence of 30% DMSO, whereas invasion/runoff products for inserts that have <30% GC content may not be stable enough to stay hybridized in that particular reaction mixture. In order to mitigate this and enable successful invasion/runoff across a wider range of GC % for the inserts of the sequencing library, one can exchange the solution of 30% DMSO, invasion oligonucleotide and polymerase for a solution that contains 5% DMSO, invasion oligonucleotide and polymerase, for example. In some experiments, cycling through different invasion-reaction mixtures (e.g., a first invasion-reaction mixture, followed by a second invasion-reaction mixture, followed by the first invasion-reaction mixture, etc.) limited the GC bias.

Figure 6:
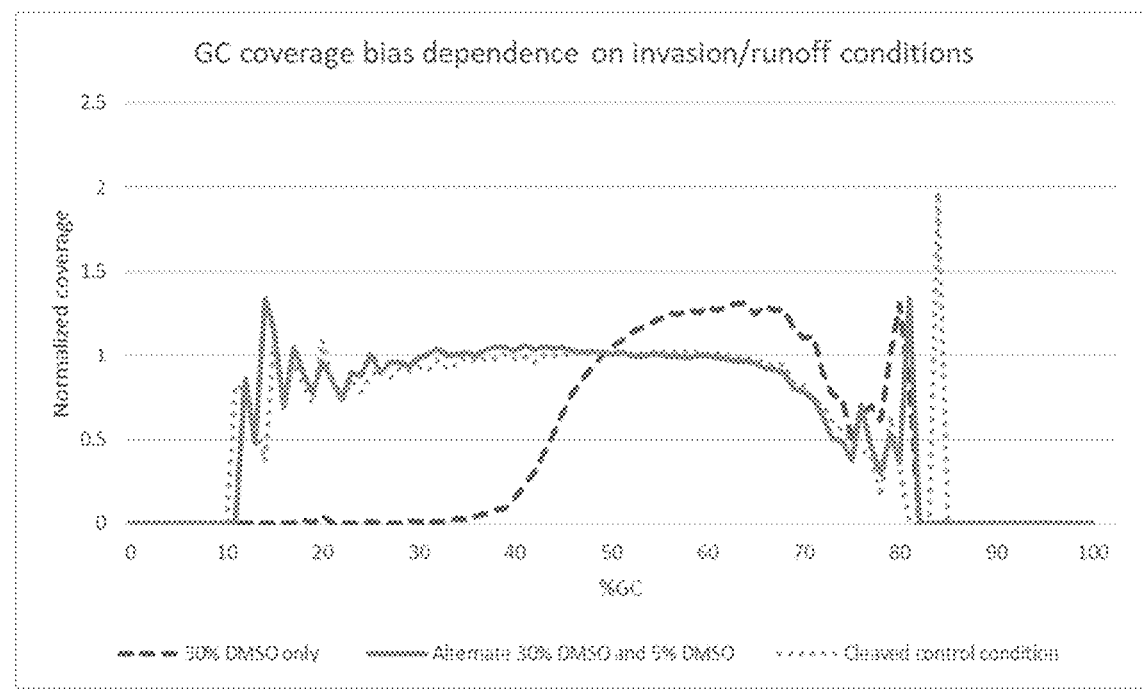
FIG. 6 shows a graph depicting the GC coverage bias dependence on invasion-reaction conditions. Shown in the graph are results for a 100×150 bp paired-strand sequencing run on dsDNA clusters that were subjected to the methods described herein. The GC graph is for the first 100 cycles of the 100×150 bp paired-strand sequencing experiment. Utilizing one invasion-reaction mixture (e.g., 30% DMSO only) skews the sequencing reads to cover 40-80% GC content. Alternating cycles of two invasion-reaction mixtures, that is a first invasion-reaction mixture containing 30% DMSO and a second invasion-reaction mixture containing 5% DMSO, results in greater coverage of all GC content.

An example demonstrating the importance of modulating the invasion and runoff condition for obtaining even GC coverage representation in DNA sequencing is shown in FIG. 6. The same experimental conditions as outlined in the examples above were used in two lanes of the flow cell: (i) a positive control lane (lane #1) was treated with USER enzyme mix after cluster amplification, which cleaved the forward amplicons (which contained a uracil base and were formed by extending the forward flow cell primers) from the flow cell surface, and (ii) another lane (lane #2) of the flow did not go through cleavage of any of the flow cell primers and instead went through a strand invasion and runoff protocol, based on strand invasion and runoff in presence of 30% DMSO, as mentioned above. In a third lane (lane #3) of the flow cell, the invasion and runoff reaction was split up into two different steps: (i) one step was identical to the invasion and runoff conditions in lane #2, and this was followed by (ii) an additional step of invasion and runoff conditions with 5% DMSO and 2.5M betaine. The resulting data in FIG. 6 shows the benefit of performing a plurality of distinct invasion reaction cycles, resulting in a much broader coverage of the range of GC content. The invasion and runoff reactions performed first in 30% DMSO, and followed by an additional invasion and runoff step in 5% DMSO and 2.5M betaine (lane #3), showed a similar GC coverage bias profile compared to the positive control lane that received cleavage of the forward amplicons (lane #1), and had much more even coverage compared to the condition that used 30% DMSO only (lane #2). The *Salmonella* genomic library, which was used for this experiment, has a genome with a GC content ranging from approximately 15% to approximately 85%, and the GC coverage is targeted to be as uniform as possible (normalized to 1) across this range. The spikes that are observed at the low and high ends of the GC-range are due to the relatively low coverage (low sampling) in this particular experiment and the low representation of the extreme GC content fragments (<20% and >75%) in this genome. Having greater coverage of reads across the entirety of the genome aids mapping and SNP calling, and makes assembly more straightforward.

Example 5. Additional Approaches to Sequencing Two Strands of the Same Polynucleotide Sequencing two strands of the sample dsDNA template is a powerful technique to improve sequencing accuracy and is commonly performed in next-generation sequencing (NGS) workflows. Sequencing by synthesis (SBS) is a common implementation of NGS and paired-end sequencing is typically performed on monoclonal clusters generated by a clonal amplification process. It is typical for solid-phase clonal amplification to generate monoclonal clusters that each consist of many double-stranded DNA (dsDNA) copies (10s to 100,000s) of the initially seeded library nucleic acid molecule. In SBS workflows, clusters of dsDNA are difficult to sequence effectively with high accuracy and read length, especially as miniaturization pushes the clusters to become more densely arranged on a solid support. To initiate an SBS sequencing reaction, a sequencing primer needs to hybridize to a single-stranded region in the dsDNA and be extended by a polymerase. Individual strands in dsDNA clusters are difficult to access for hybridization of sequencing primers. Additionally, the polymerases used during SBS to incorporate 3' reversibly terminated nucleotides (dNTPs) or native dNTPs (for example in pyrosequencing) typically do not have strand-displacement capabilities, and so even if one is successful in incorporating sequencing primers into dsDNA molecules, it is still challenging to extend said sequencing primers when the vast majority of DNA molecules are in dsDNA format.

Due to these constraints, dsDNA amplicons in clusters are typically processed into single-stranded DNA (ssDNA), sometimes referred to as linearization, by a variety of methods. The dsDNA structures may be linearized by cleavage of one or both strands with a restriction endonuclease or by cleavage of one strand with a nicking endonuclease. Other methods of cleavage can be used as an alternative to restriction enzymes or nicking enzymes, including chemical cleavage (e.g., cleavage of a diol linkage with periodate), cleavage of abasic sites by cleavage with endonuclease, by exposure to heat or alkali, cleavage of ribonucleotides incorporated into amplification products otherwise comprised of deoxyribonucleotides, photochemical cleavage, or cleavage of a peptide linker. Alternatively, the primers may be attached to the solid support with a cleavable linker, such that upon exposure to a cleaving agent, all or a portion of the primer is removed from the surface. For example, one linearization method requires one or both of the immobilized primers to have a cleavable site, such as a uracil, diol, 8-oxoG, disulfide, photocleavable moieties, an RNA base or an endonuclease cleaving site. After the solid phase clonal amplification process is complete, one of the two species of solid phase primers (either forward or reverse) can be cleaved (chemically, enzymatically or optically), followed by a denaturation step to remove the cleaved molecules. This transforms the dsDNA molecules into ssDNA molecules within the cluster and provides a region available for hybridization of a sequencing primer to initiate a sequencing reaction. The monoclonal clusters can proceed to any necessary post-processing steps such as blocking of free 3'-OH ends, removal of select amplicons, or hybridization of a sequencing primer.

In conventional workflows, once ssDNA molecules are generated a first sequencing read is performed by hybridizing a first sequencing primer to a complementary region (e.g., a region within the adapter portion) of the ssDNA molecule. In the presence of an enzyme (e.g., a DNA polymerase), nucleotides (e.g., labeled nucleotides) are incorporated and detected such that the identity of the incorporated nucleotides allows for the identification of the first strand. When the first read is complete (i.e., the first strand is read to a sufficient length with sufficient accuracy) the second strand that was initially cleaved during linearization must be regenerated prior to starting the second read. This can be done by additional amplification steps, such as additional rounds of bridge PCR or another amplification process. Following an additional amplification step after the first sequencing read, the second strand may then be sequenced. All of these steps add complexity and time to the DNA sequencing workflow and can also introduce additional errors made by the polymerase used during solid phase amplification. Highly accurate sequencing methods would greatly benefit from novel methods that bypass the need for additional amplification steps between the two sequencing reads of conventional paired-end sequencing workflows.

In accordance with various embodiments, the methods disclosed herein permit reading of the original first and second strands (e.g., the first and second strand of the amplicons), reducing the time, reagents, expense, and risk of polymerase error inherent in previous methods. Importantly, methods described herein prevent the need for additional solid phase amplification between the two sequencing reads. In embodiments, methods disclosed herein utilize strand invasion using invasion primers into dsDNA amplicons bound to a solid phase, followed by polymerase extension of the invasion primers. Strand invasion into dsDNA can be challenging in general, but can be particularly challenging in dense monoclonal clusters of dsDNA where DNA molecules are packed tightly together in a spatially localized fashion on a solid phase. Because the local concentration of full-length complementary strands is very high, insertion of a traditional primer oligonucleotide is thermodynamically unfavorable.

The invasion primers are oligonucleotide sequences that binds to one strand of the dsDNA molecule in the cluster. For example, the invasion primer may bind to a portion of the common adapter sequence of only the forward, or only the reverse amplicons in clusters. These invasion oligonucleotides may include nucleic acids having a binding affinity higher than the binding affinity of standard or canonical DNA oligonucleotides, such as locked nucleic acids (LNA), peptide nucleic acids (PNAs), 2'-O-methyl RNA:DNA chimeras, minor groove binder probes (MGB), or morpholino probes. The invasion primers may include one or more deoxyuracils (dUs). The invasion primers may include one or more phosphorothioate groups. The invasion primers are introduced into a flow cell that contains monoclonal dsDNA clusters generated using a known amplification method or an amplification method described herein. Some of these invasion primers can undergo spontaneous strand invasion into dsDNA, as is the case for example for PNA invasion primers under low ionic strength conditions, while other invasion primers may need assistance of additives such as DMSO, ethylene glycol, formamide, betaine, or other denaturants or additives that assist strand invasion by inducing more breathability within dsDNA amplicons. For example, such additives may include a buffered solution containing about 0 to about 50% DMSO, about 0 to about 50% ethylene glycol, about 0 to about 20% formamide, or about 0 to about 3M betaine. In order to achieve sufficient "breathability" within dsDNA amplicons that are bound to a solid phase, it is helpful to include additives that can assist the "fraying" of the dsDNA molecules, particularly at the 5' and 3' ends.

As described herein and in Example 1, the invasion oligonucleotide can be introduced without a polymerase and allowed to invade and anneal to the complementary region, or it may be introduced together with a polymerase for runoff extension. In certain experiments, it is preferable to introduce the invasion oligonucleotide (e.g., a 15-75 bp invasion primer) together with a polymerase in the same reaction mixture. Because of the close physical proximity of the forward and reverse strands of the dsDNA molecules within a cluster, the hybridization of the invasion oligo to one of the DNA strands is often transient, and can be outcompeted easily by the reannealing of the full-length forward and reverse strands of the dsDNA molecules. To efficiently extend the invasion oligos that transiently hybridize, it is useful to have the polymerase within the same reaction mixture such that the polymerase can immediately extend the invasion oligo during the transient hybridizations that occur.

The initiation point for the first sequencing reaction is provided by annealing a sequencing primer complementary to a region within one of the strands. In the presence of an enzyme (e.g., a DNA polymerase), nucleotides (e.g., labeled nucleotides) are incorporated and detected such that the identity of the incorporated nucleotides allows for the identification of the first strand. Thus, the first sequencing reaction may include hybridizing a sequencing primer to a region of an amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand. Note, the second sequenced strand is present while sequencing the first strand, albeit the second strand is hybridized to the invasion strand.

Figure 8A:
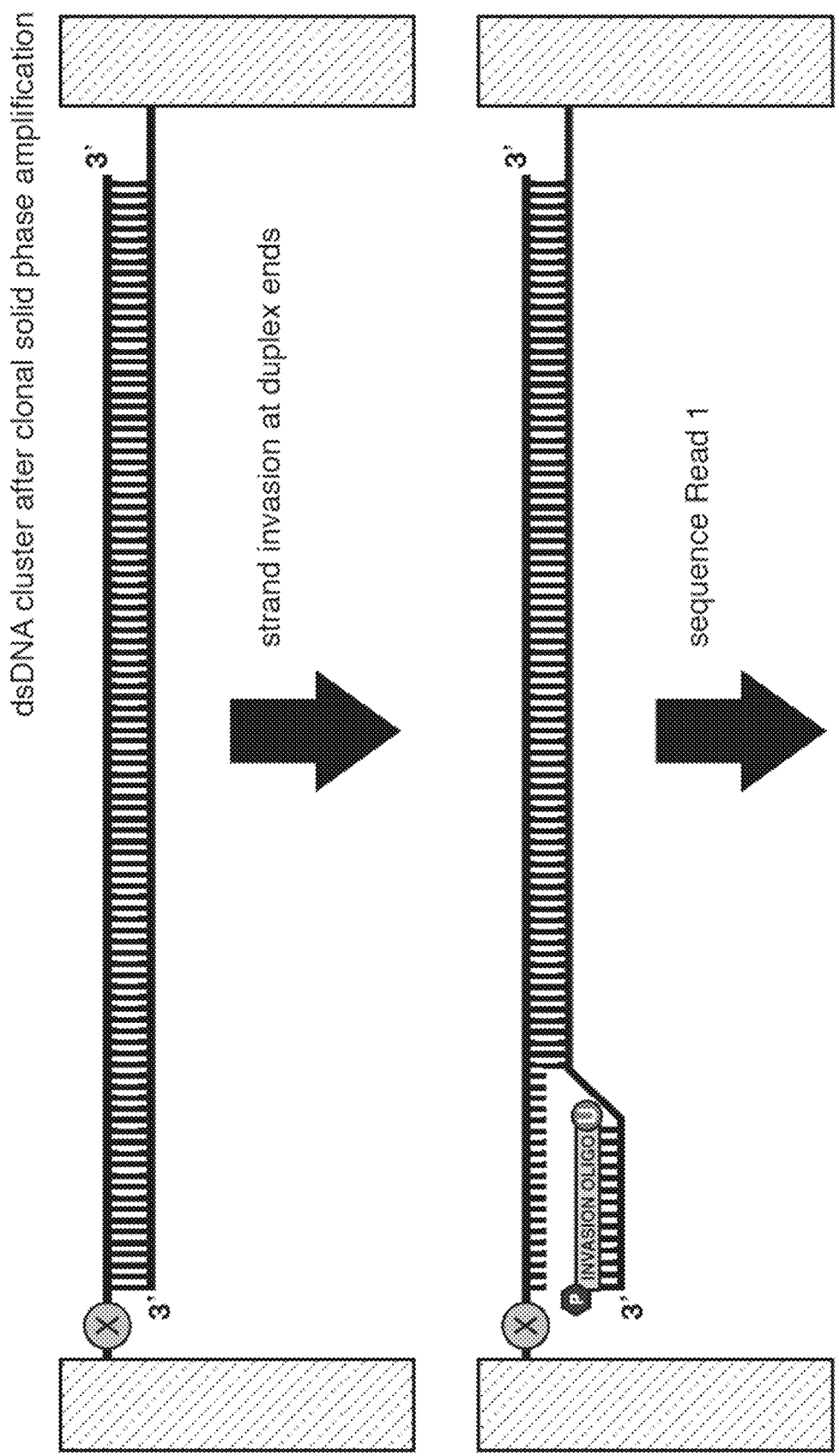
FIGS. 8A-8D illustrate an embodiment of paired-strand sequencing by strand invasion of an invasion primer at the 3' end of a first strand of a duplex, followed by runoff extension of the invasion primer by a strand-displacing polymerase.
Figure 8B:
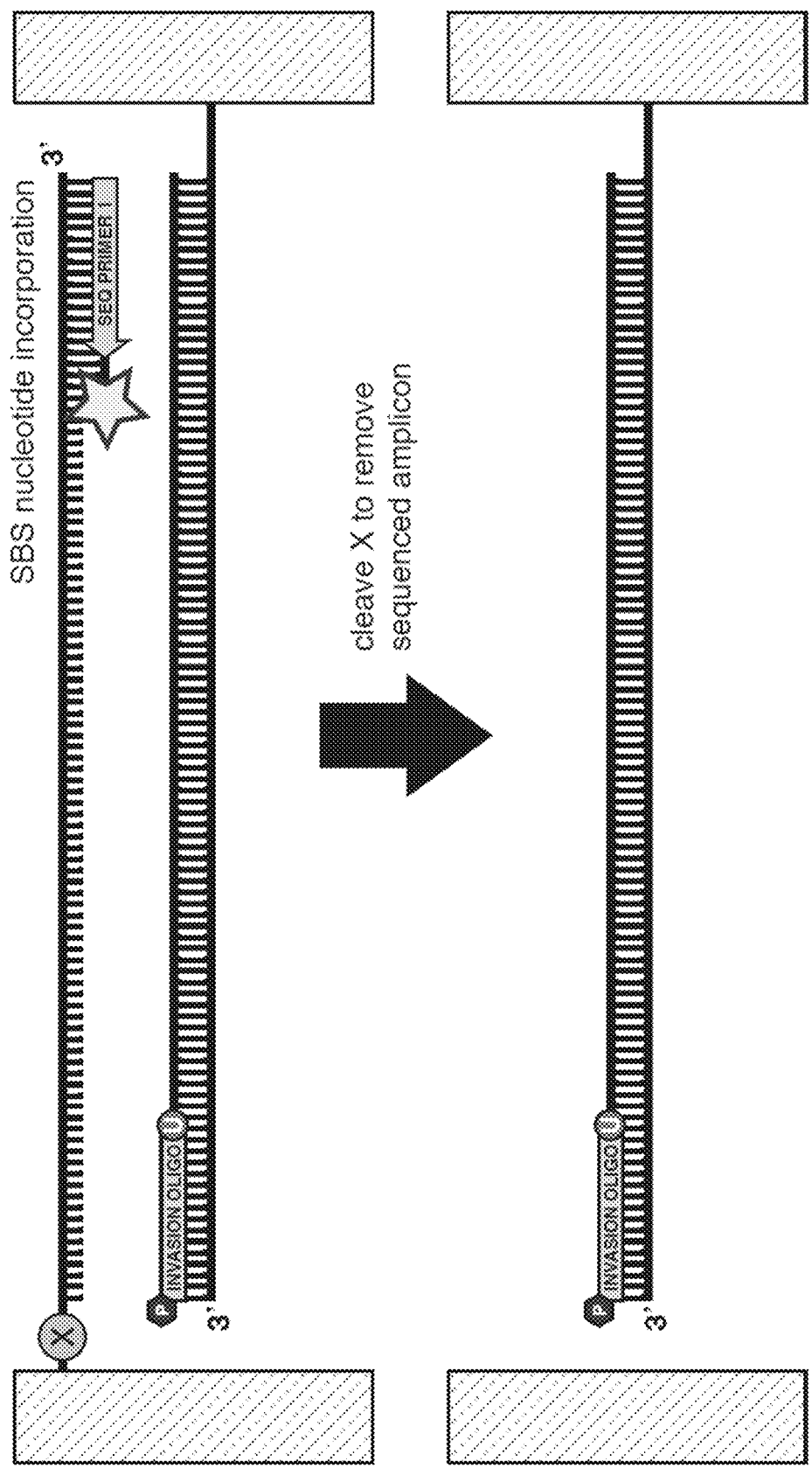
Figure 8C:
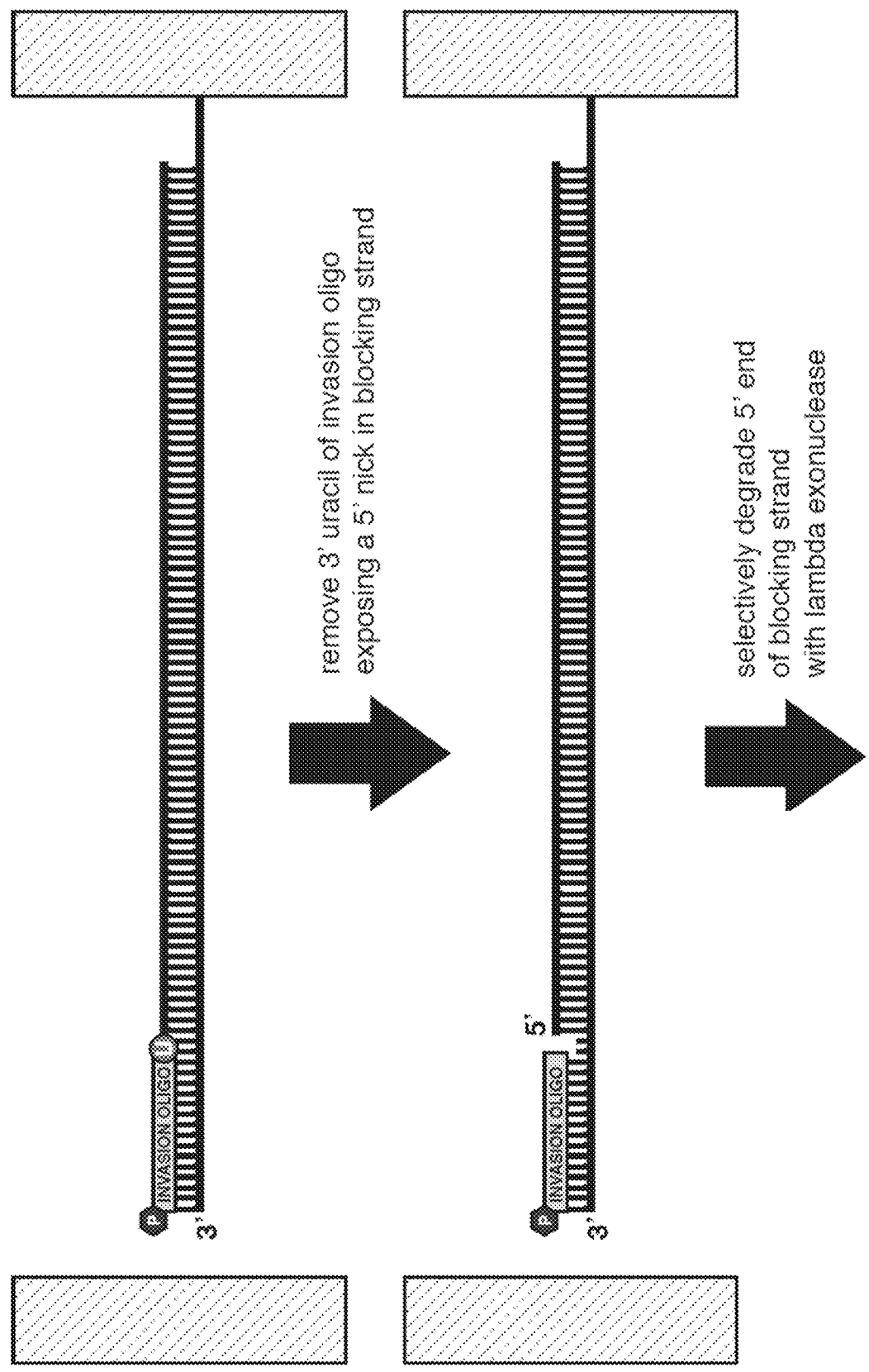
Figure 8D:
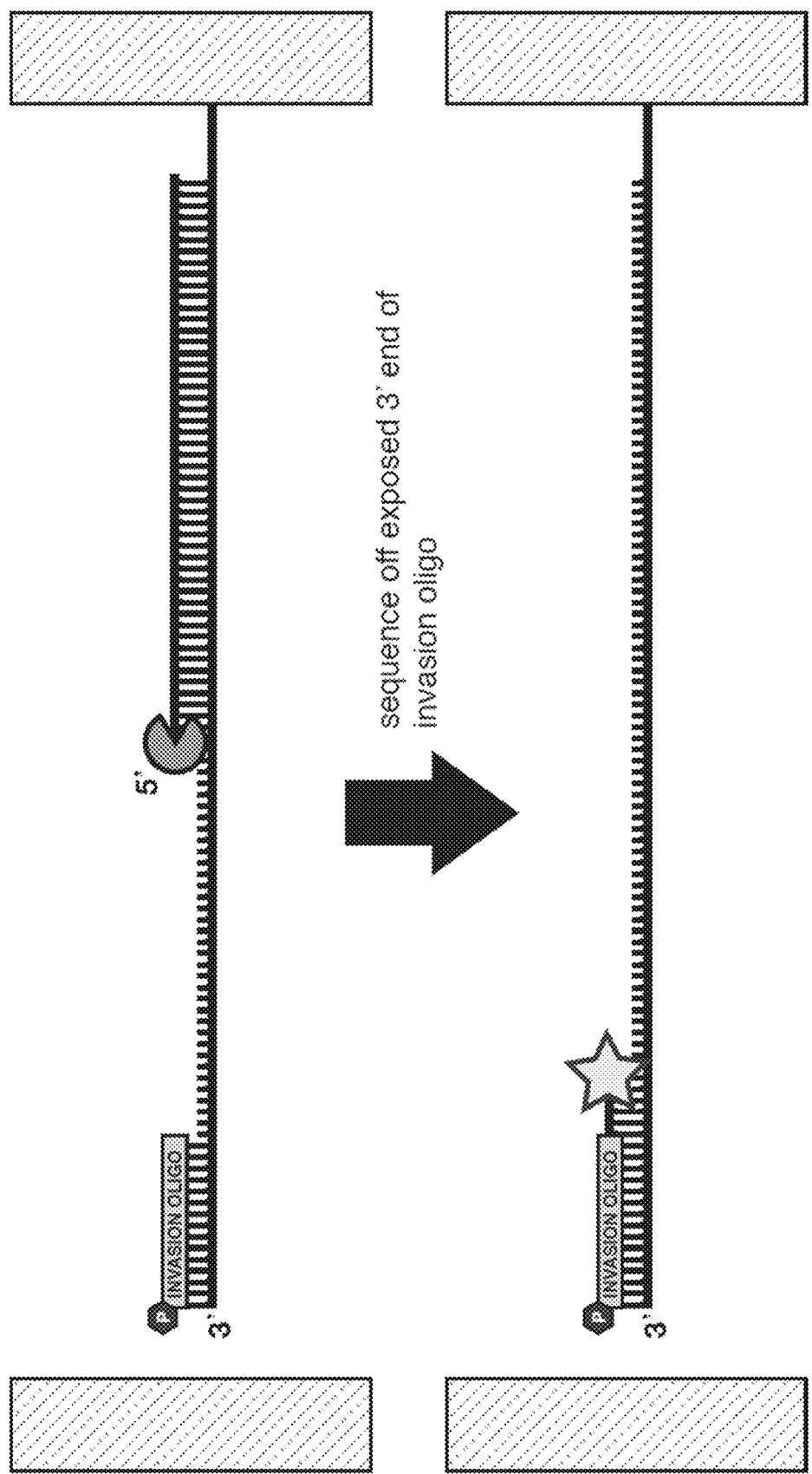

Additional embodiments of methods of paired-strand sequencing by strand invasion of an invasion primer are disclosed herein. FIG. 8A illustrates an invasion primer annealed to the 3' end of one of the strands. In embodiments, the invasion primer includes one or more 5' phosphorothioate groups (e.g., 3-5 phosphorothioate linking groups) to protect from exonuclease digestion. In embodiments, the invasion primer further includes a cleavable site (e.g., a 3' deoxyuracil triphosphate (dUTP)). After runoff extension of the invasion oligonucleotide has been completed, one strand of the initial dsDNA molecule is now single-stranded and available for a first sequencing read, as shown in FIG. 8B. This renders one of the two strands of the original dsDNA amplicon available for hybridization of a sequencing primer to initiate the SBS process. The sequenced strand may optionally further be cleaved at a cleavable site (represented as 'X') and removed, thus leaving the complementary strand available for sequencing, as illustrated in FIG. 8B. Subsequently, the 3' end of the invasion primer may be cleaved at a cleavable site (e.g., nicked at the dU), leaving behind a 5'-phosphate in the extended part of the invasion strand that can subsequently be degraded with a 5' to 3' exonuclease, allowing for the invasion primer to serve as a sequencing primer for the second strand, as illustrated in FIGS. 8C-8D. In some embodiments, the invasion primer is treated with a 3' phosphatase (for example Endonuclease IV or PNK) to generate a 3' hydroxyl group prior to sequencing.

Figure 9A:
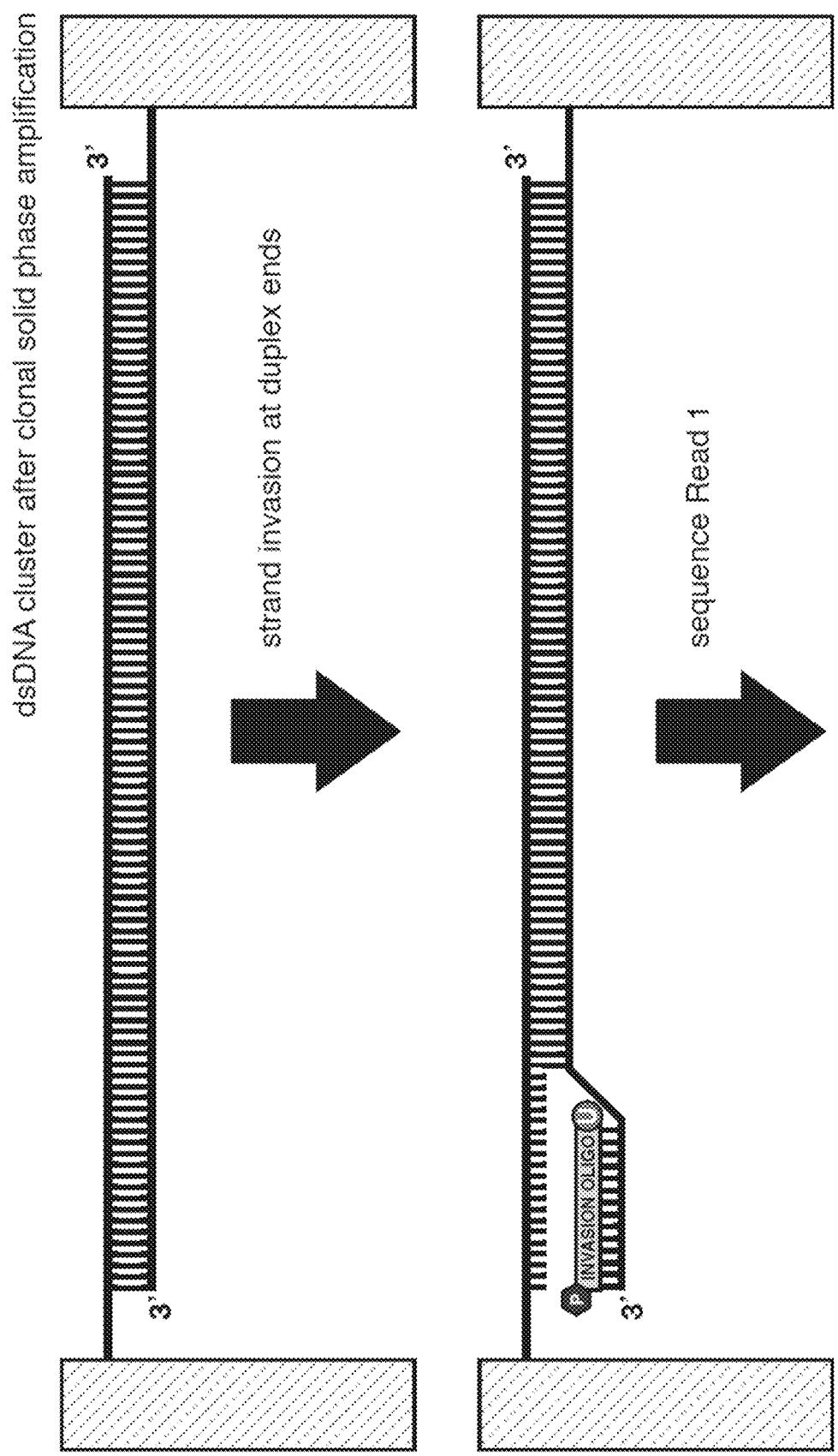
FIGS. 9A-9D illustrate an embodiment of paired-strand sequencing by strand invasion of an invasion primer at the 3' end of a first strand of a duplex, followed by runoff extension of the invasion primer by a strand-displacing polymerase.
Figure 9B:
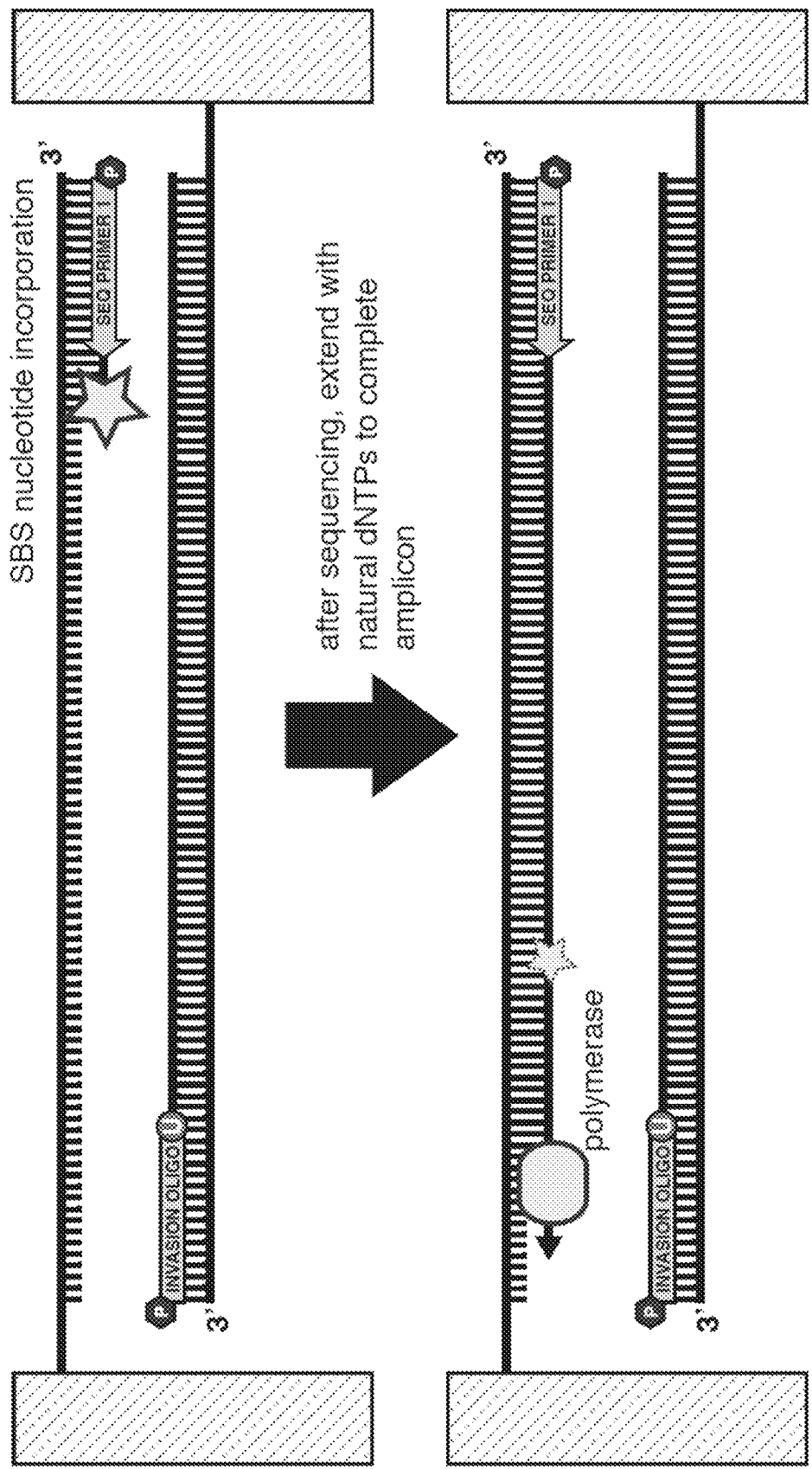
Figure 9C:
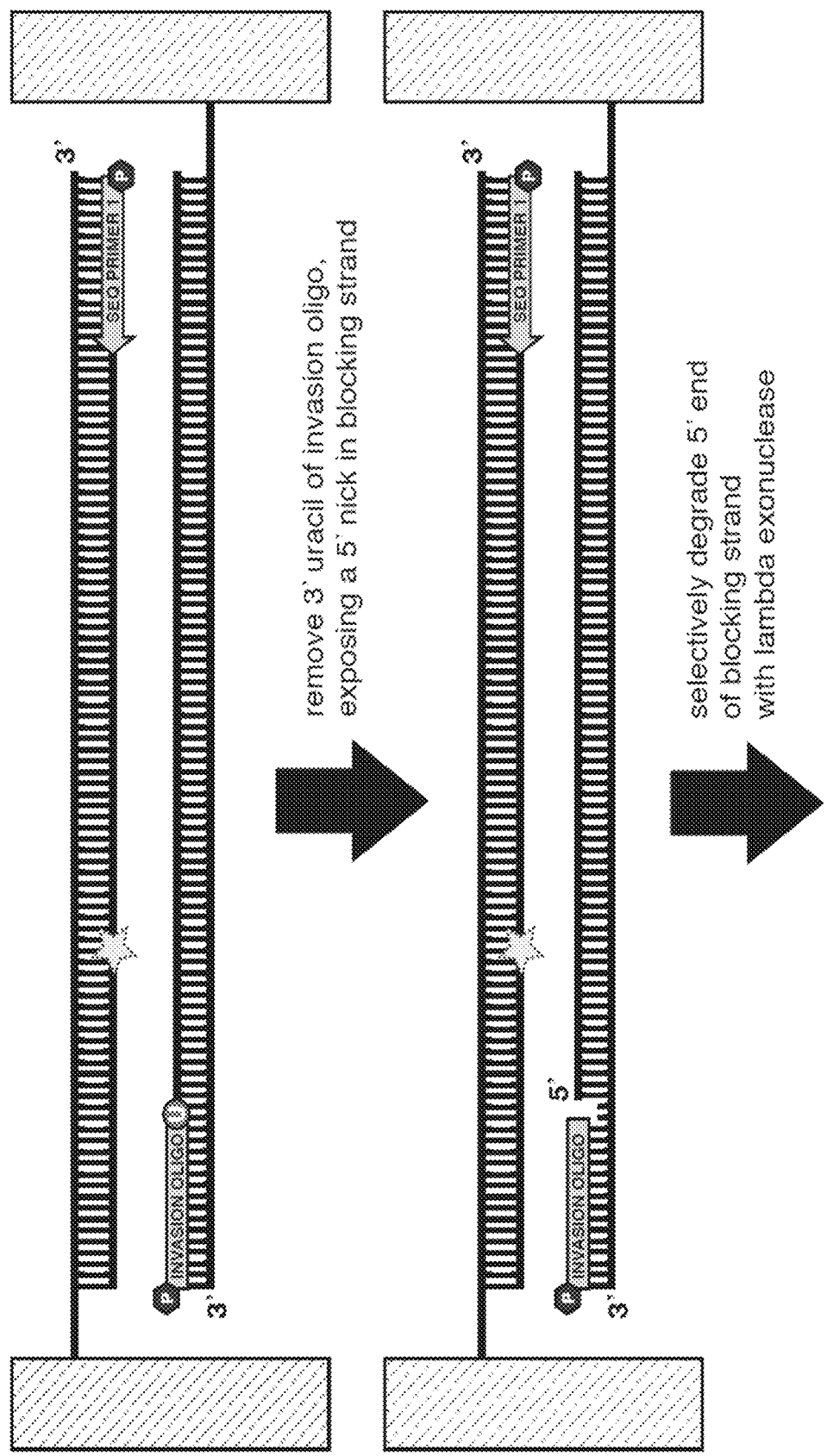
Figure 9D:
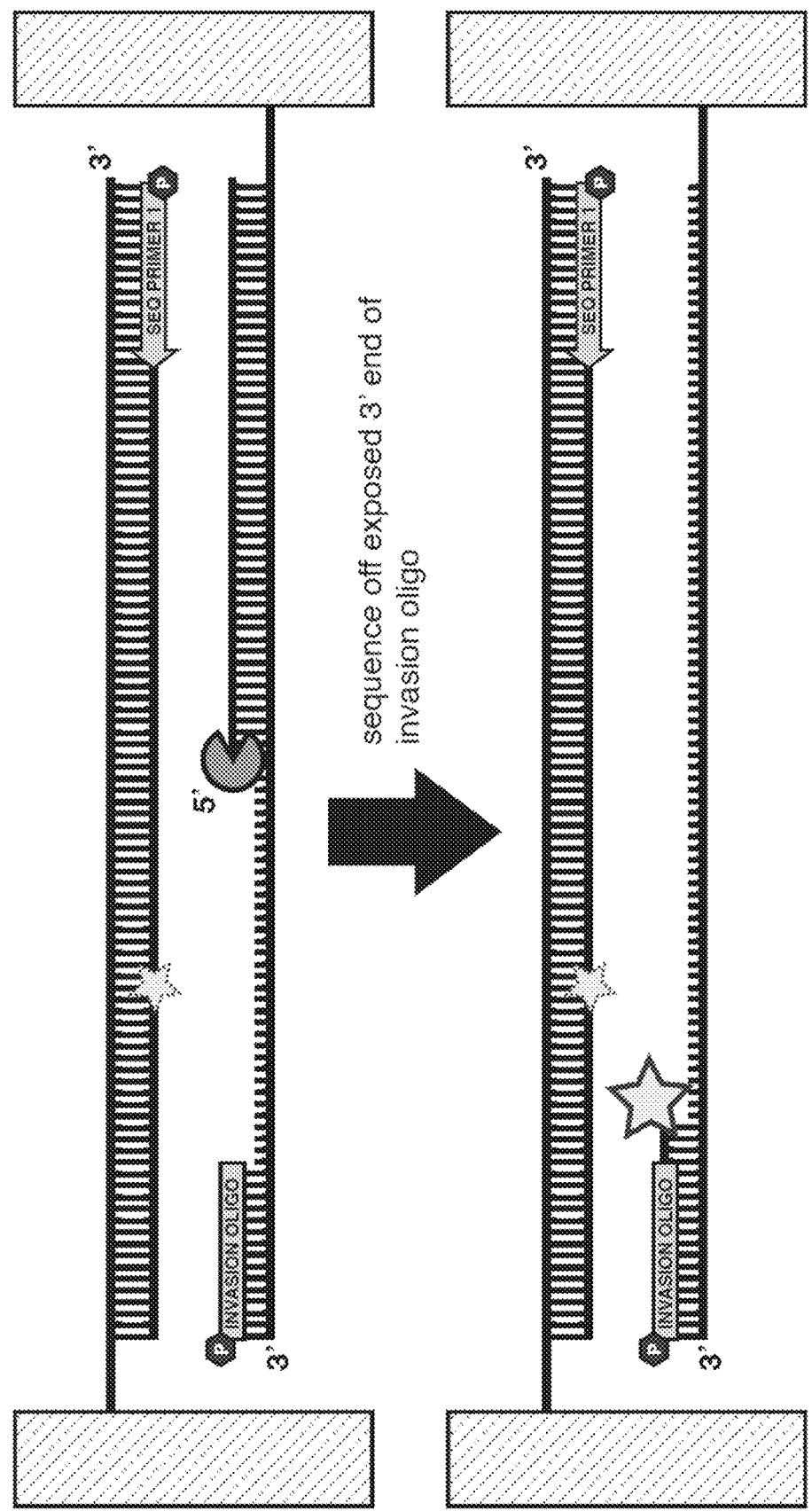
Figure 10A:
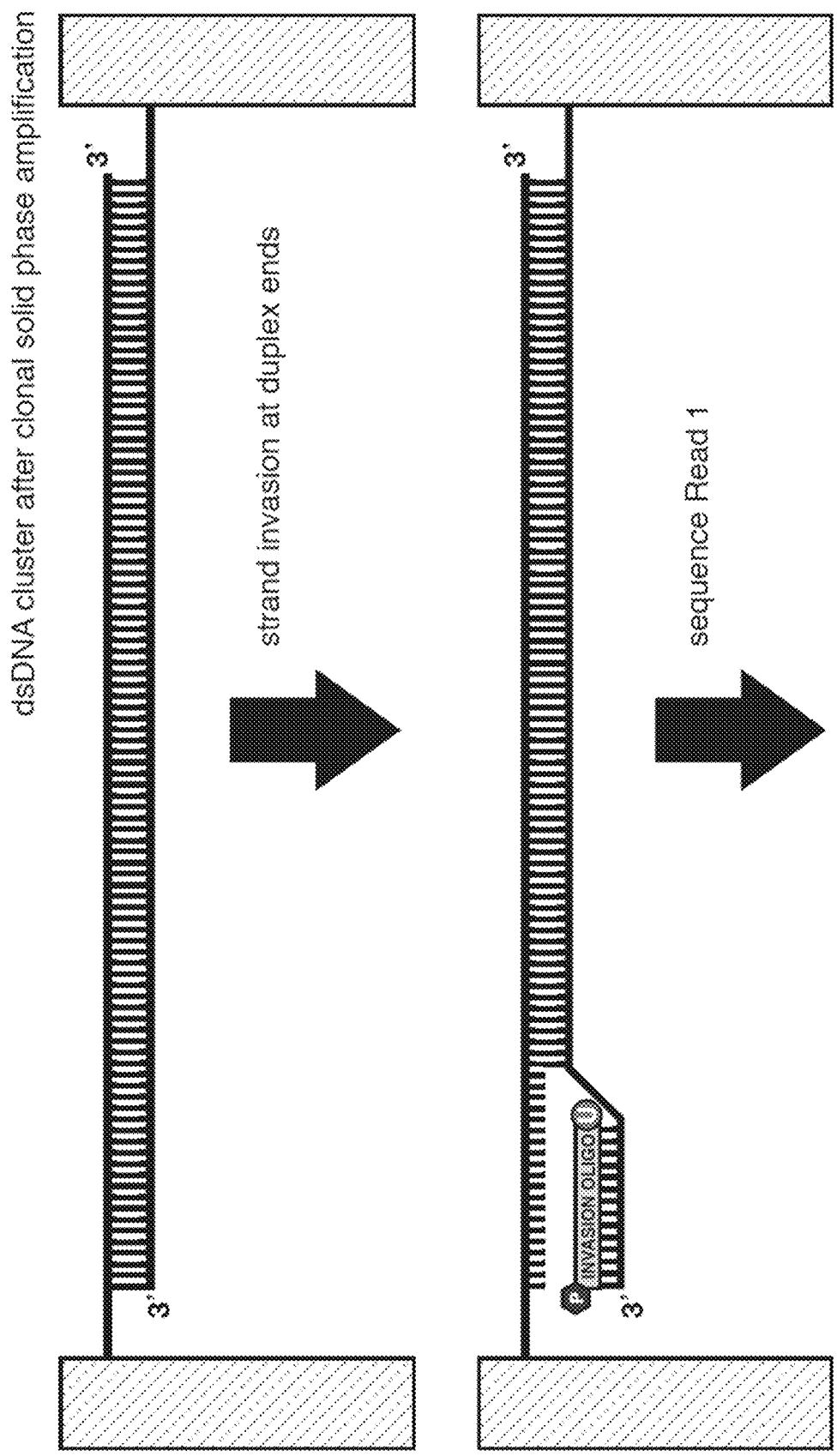
FIGS. 10A-10D illustrate an embodiment of paired-strand sequencing by strand invasion of an invasion primer at the 3' end of a first strand of a duplex, followed by runoff extension of the invasion primer by a strand-displacing polymerase.
Figure 10B:
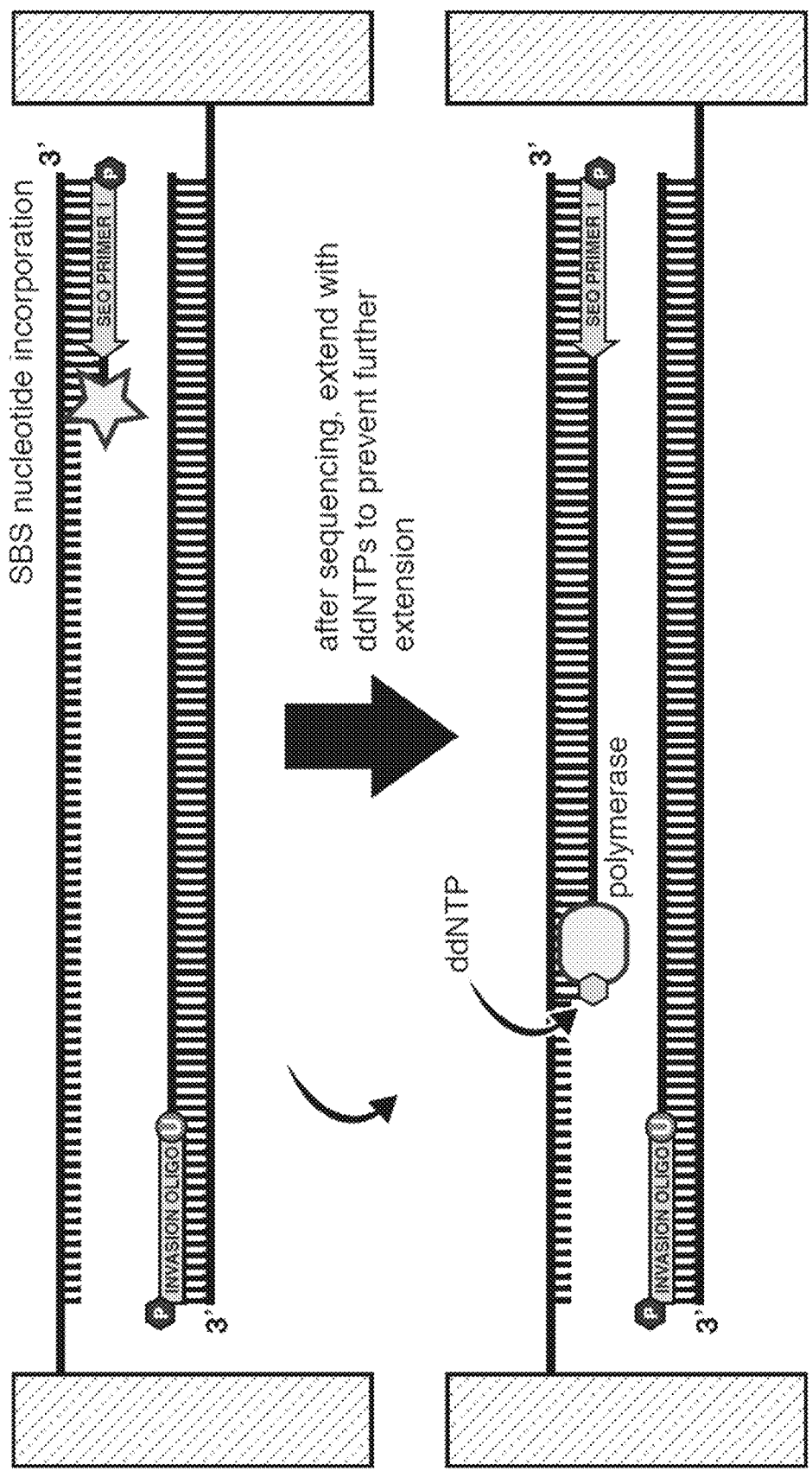
Figure 10C:
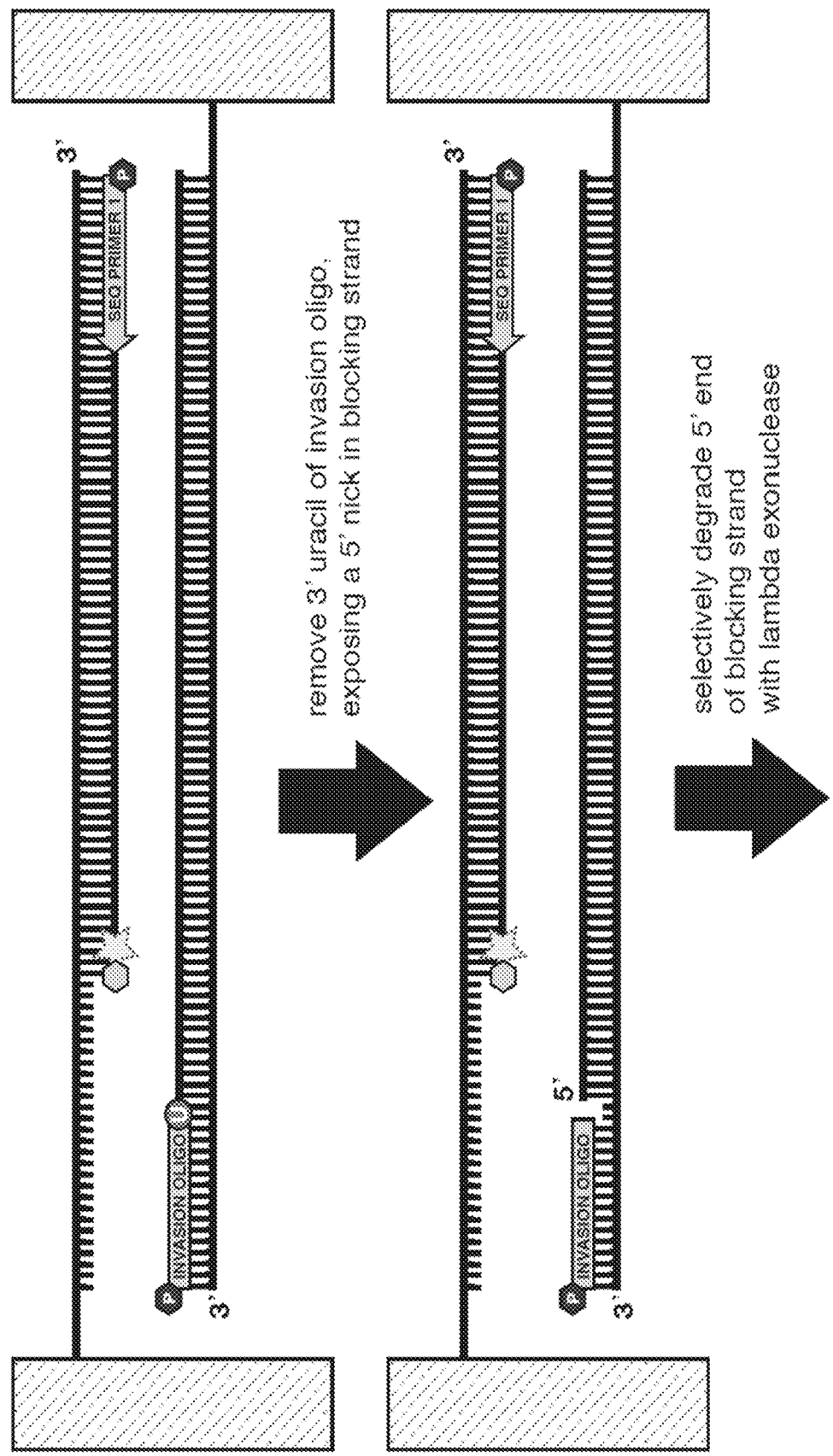
Figure 10D:
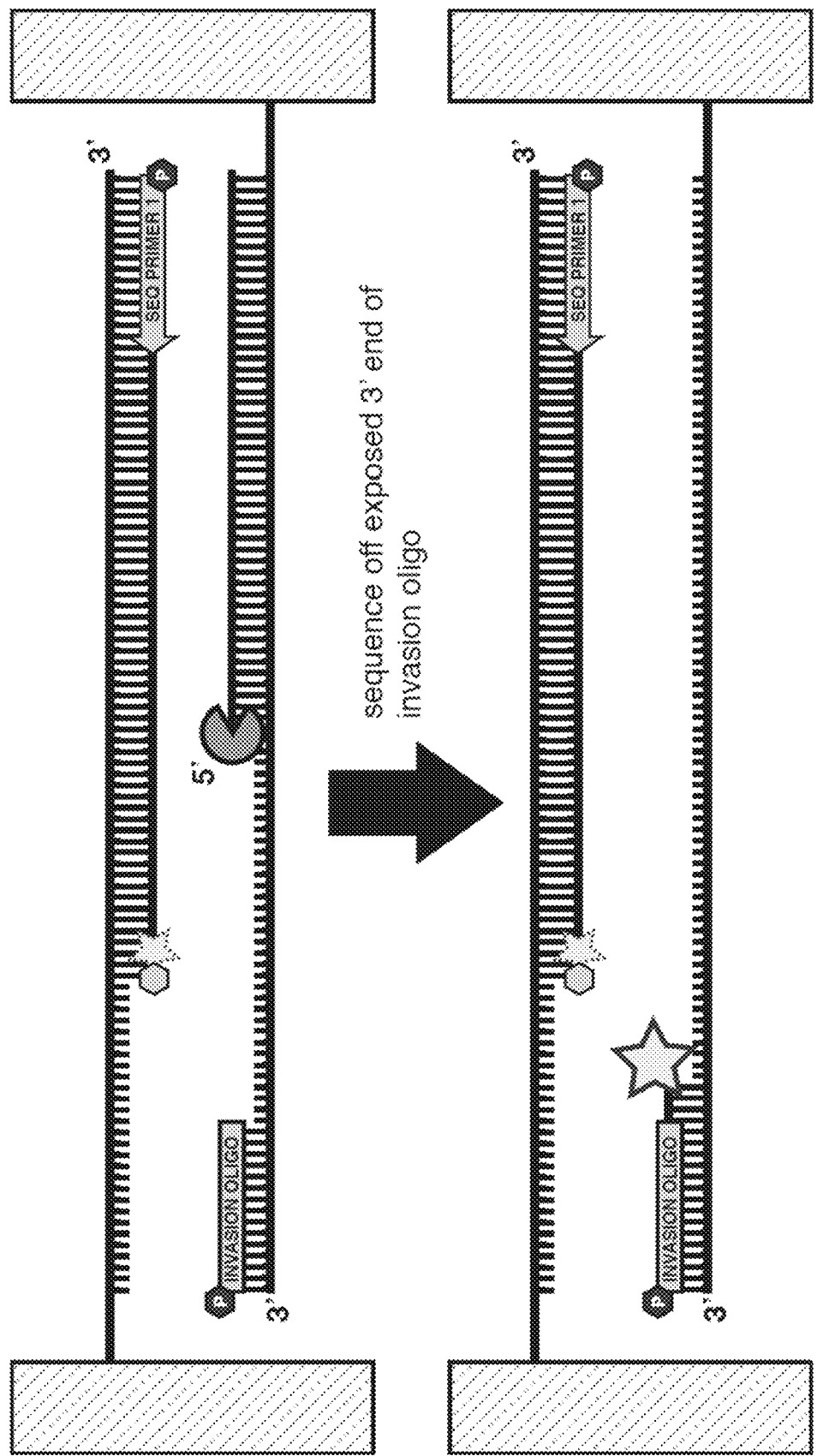

In a modified embodiment of the above method, once runoff extension of the invasion oligonucleotide has been completed, one strand of the initial dsDNA molecule is now single-stranded and available for a first sequencing read, as shown in FIG. 9B. This renders one of the two strands of the original dsDNA amplicon available for hybridization of a sequencing primer to initiate the SBS process. The sequenced strand may further be extended with natural dNTPs after sequencing the first read to complete the extension of the sequenced strand, as illustrated in FIG. 9B, thereby preventing any rehybridization of any non-sequenced amplicon to the complement. Subsequently, the 3' end of the invasion primer may be cleaved at a cleavable site (e.g., nicked at the dU and removed), leaving behind a 5'-phosphate in the invasion strand that can subsequently be degraded with a 5' to 3' exonuclease, allowing for the invasion primer to serve as a sequencing primer for the second strand, as illustrated in FIGS. 9C-9D. Alternatively, the sequenced strand may further be extended with a one or more ddNTPs to prevent further extension, as illustrated in FIG. 10B. Subsequently, the 3' end of the invasion primer may be cleaved at a cleavable site (e.g., nicked at the dU and removed), leaving behind a 5'-phosphate in the invasion strand that can subsequently be degraded with a 5' to 3' exonuclease, allowing for the invasion primer to serve as a sequencing primer for the second strand, as illustrated in FIGS. 10C-10D. In some embodiments, the invasion primer is treated with a 3' phosphatase (for example Endonuclease IV or PNK) to generate a 3' hydroxyl group prior to sequencing. Advantageously, neither of these two embodiments require the removal of the first sequenced strand, further reducing cost and time required for high-accuracy paired-strand sequencing.

Figure 11A:
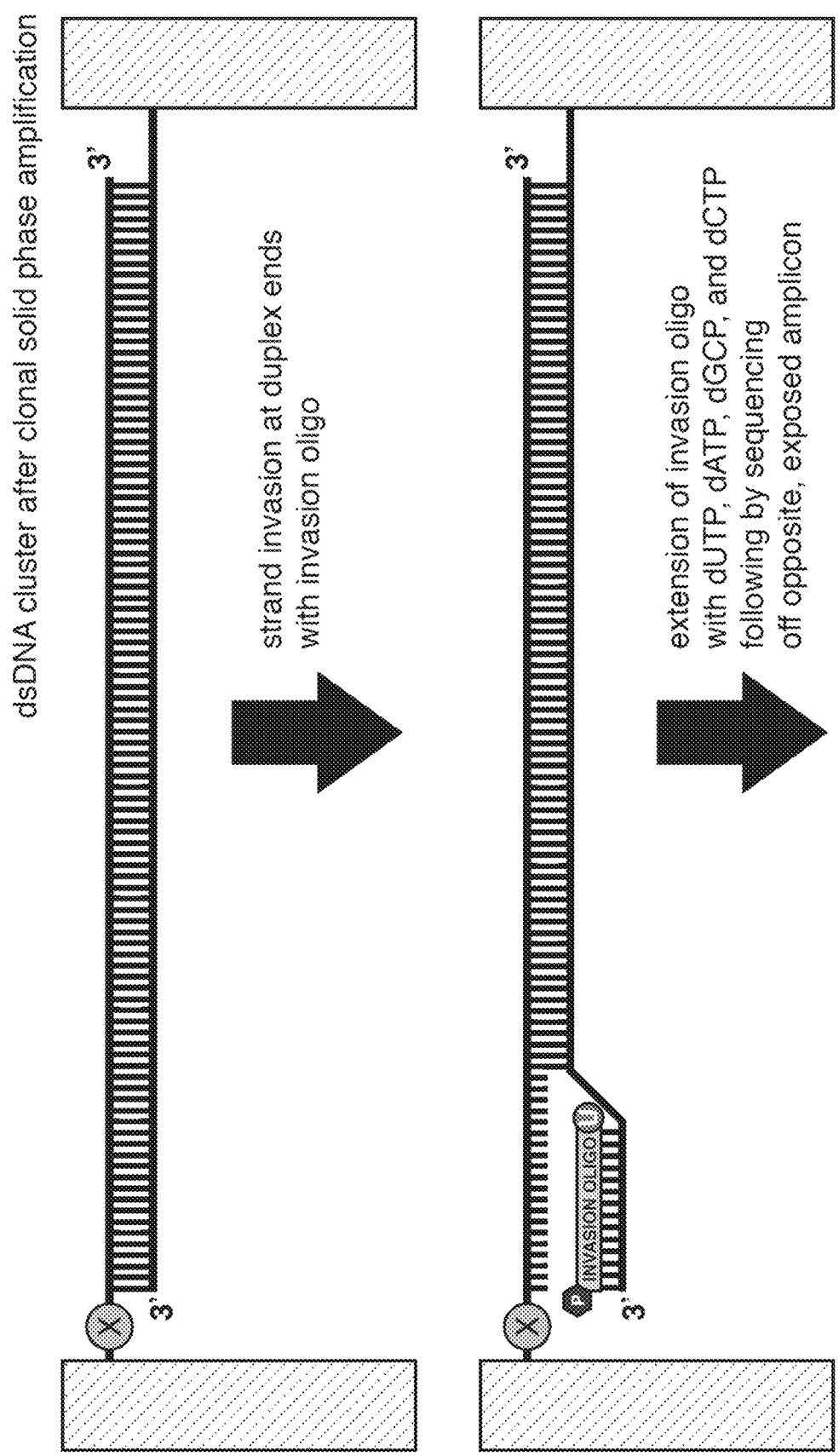
FIGS. 11A-11D illustrate an embodiment of paired-strand sequencing by strand invasion of an invasion primer at the 3' end of a first strand of a duplex, followed by runoff extension of the invasion primer by a strand-displacing polymerase.
Figure 11B:
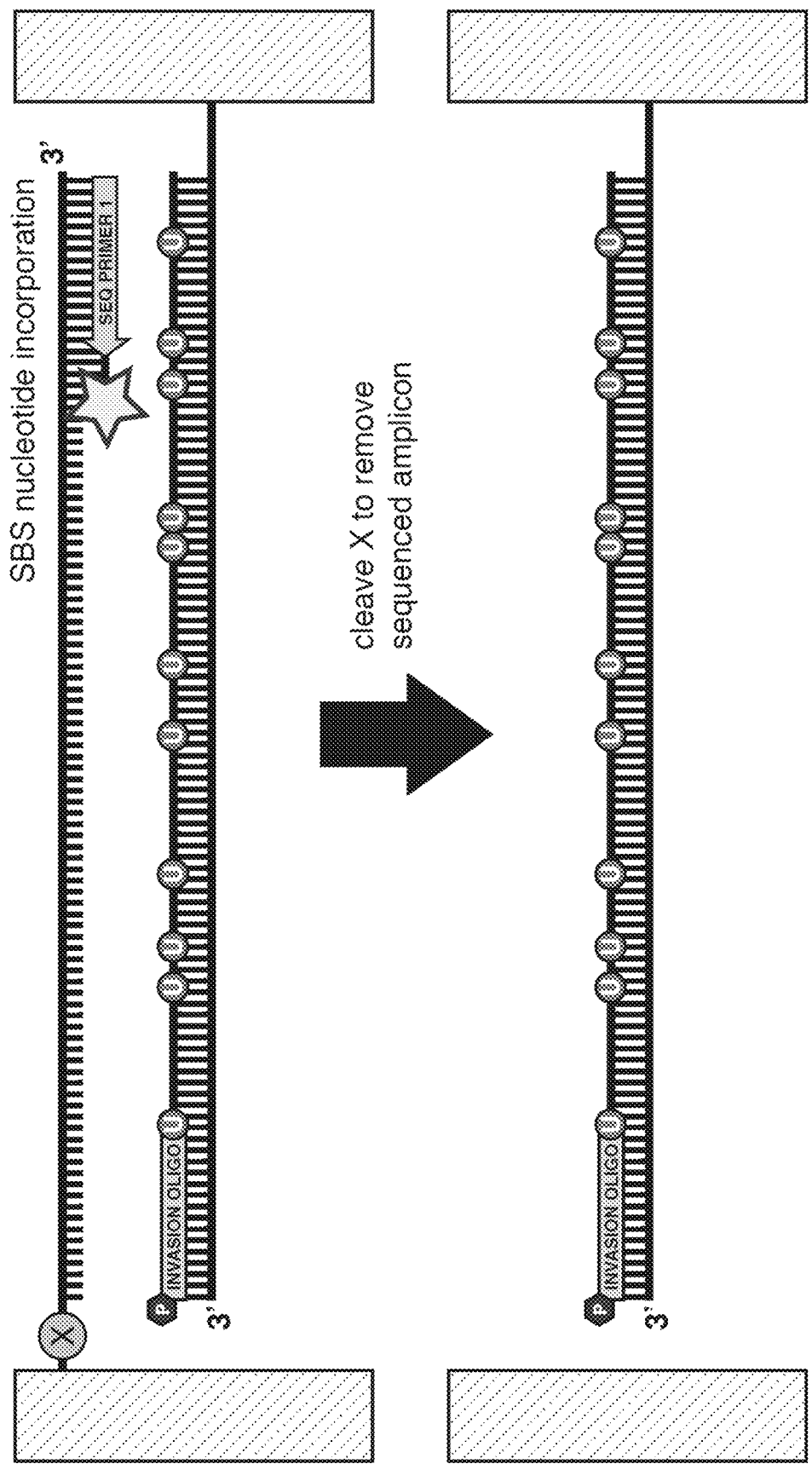
Figure 11C:
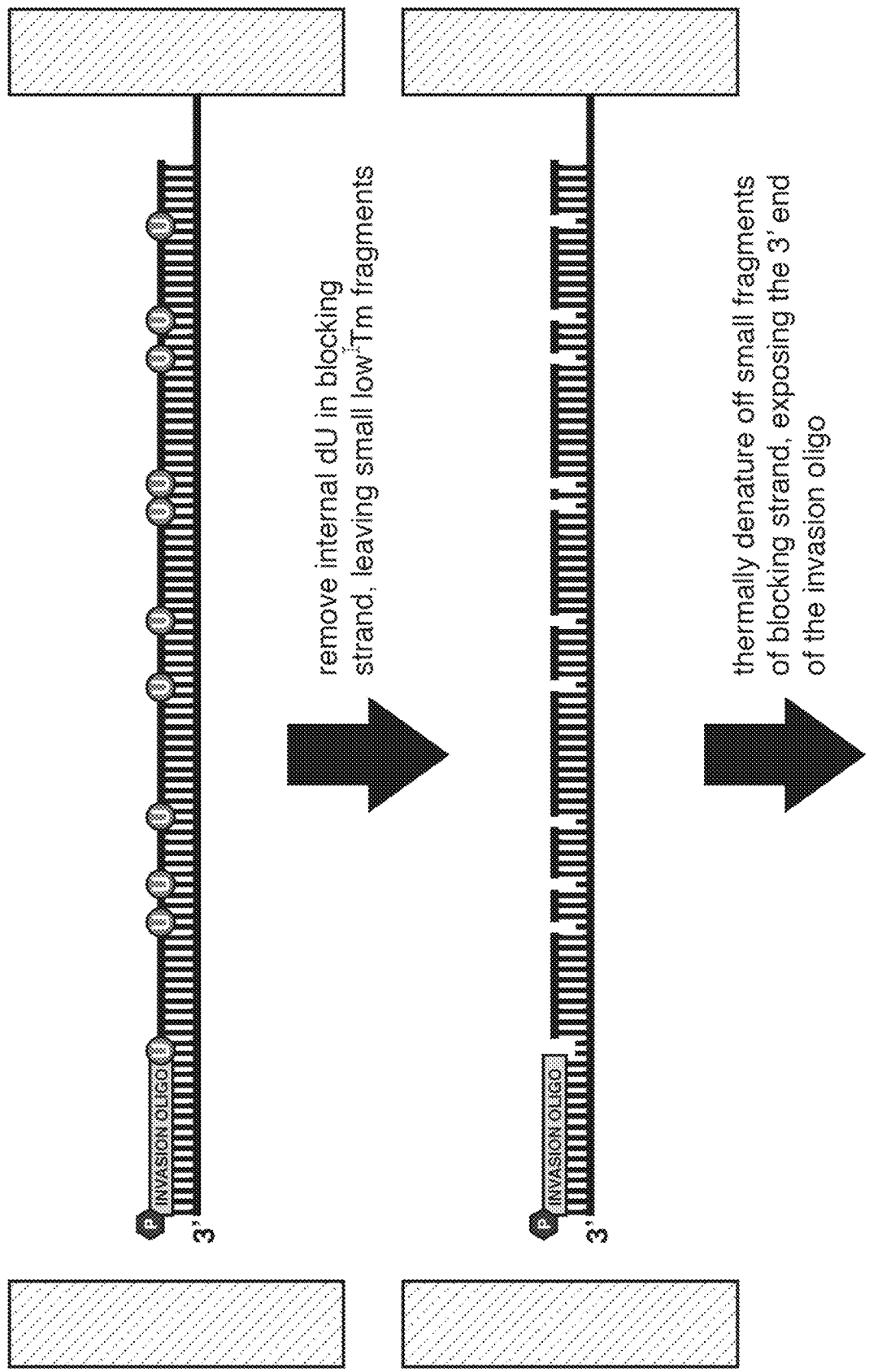
Figure 11D:
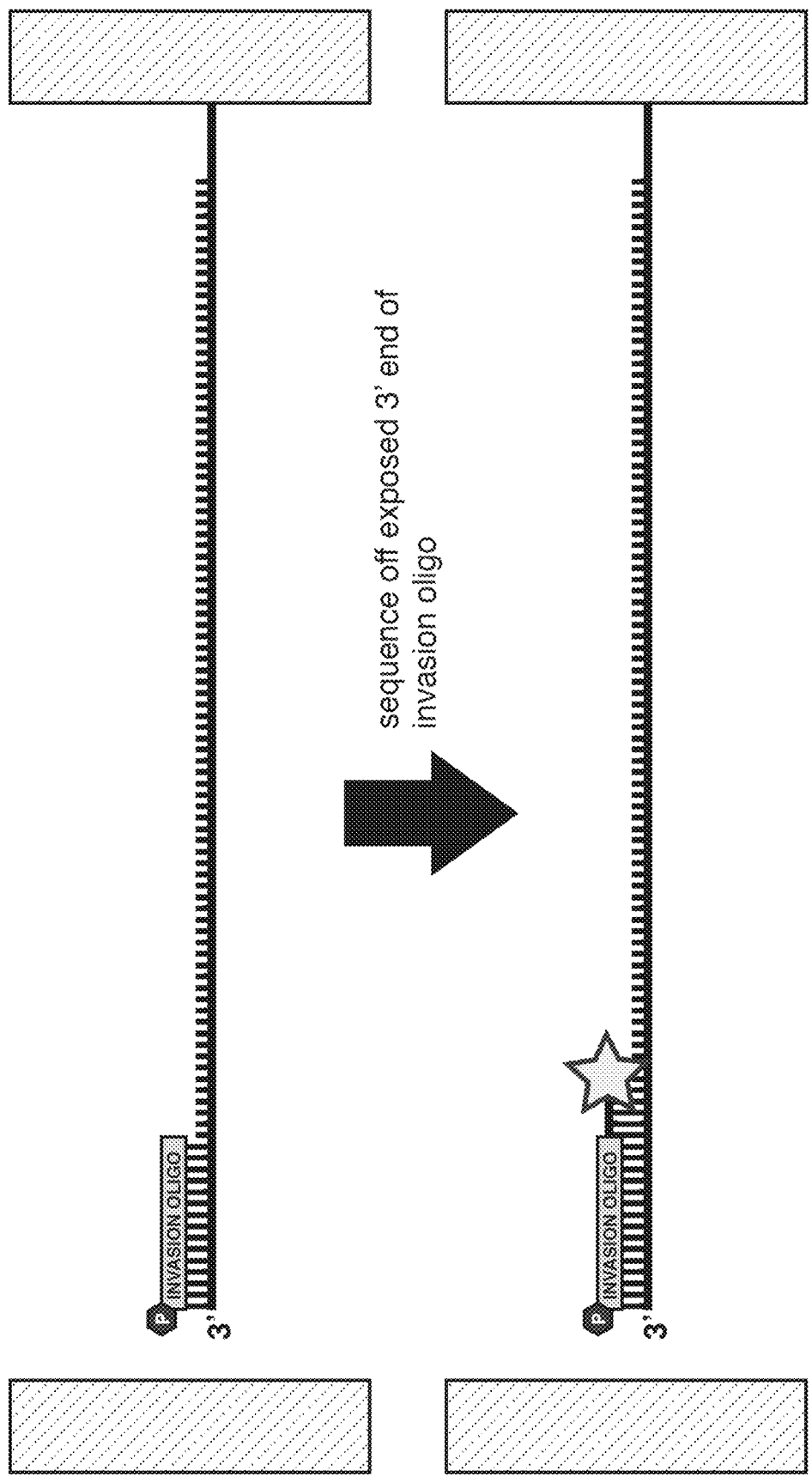

As an alternative to digesting away the invasion strand prior to sequencing the second strand, internal cleavable sites (e.g., cleavable internucleosidic bonds) may be introduced into the invasion strand. As in the methods shown supra, FIG. 11A illustrates an embodiment wherein the invasion primer is annealed to the 3' end of one of the strands. In the embodiment depicted in FIG. 11A, the invasion primer includes one or more phosphorothioate nucleic acids at the 5' end to protect from exonuclease digestion, and a cleavable site at the 3' end (e.g., one or more deoxyuracil nucleobases). Runoff extension of the invasion oligonucleotide is then performed with an amplification mixture that provides cleavable sites (e.g., a mixture of dUTP, dATP, dGTP, and dCTP nucleotides) leaving one strand of the initial dsDNA molecule single-stranded and available for a first sequencing read, as shown in FIG. 11B. The sequenced strand may optionally further be cleaved at a cleavable site (represented as 'X') and removed, thus leaving the complementary strand available for sequencing, as illustrated in FIG. 11B. Subsequently, the invasion strand may be cleaved at internal cleavable sites (e.g., cleaved at the dU sites), leaving behind small, low Tm fragments (e.g., melting temperatures in the range of 0° C. to about 60° C.) that may be thermally denatured away, as shown in FIG. 11C. Additionally, this cleavage and denaturation step exposes the 3' end of the invasion oligo, allowing for the invasion primer to serve as a sequencing primer for the second strand, as illustrated in FIGS. 11C-11D. In some embodiments, the invasion primer is treated with a 3' phosphatase (for example Endonuclease IV or PNK) to generate a 3' hydroxyl group prior to sequencing.

Figure 12A:
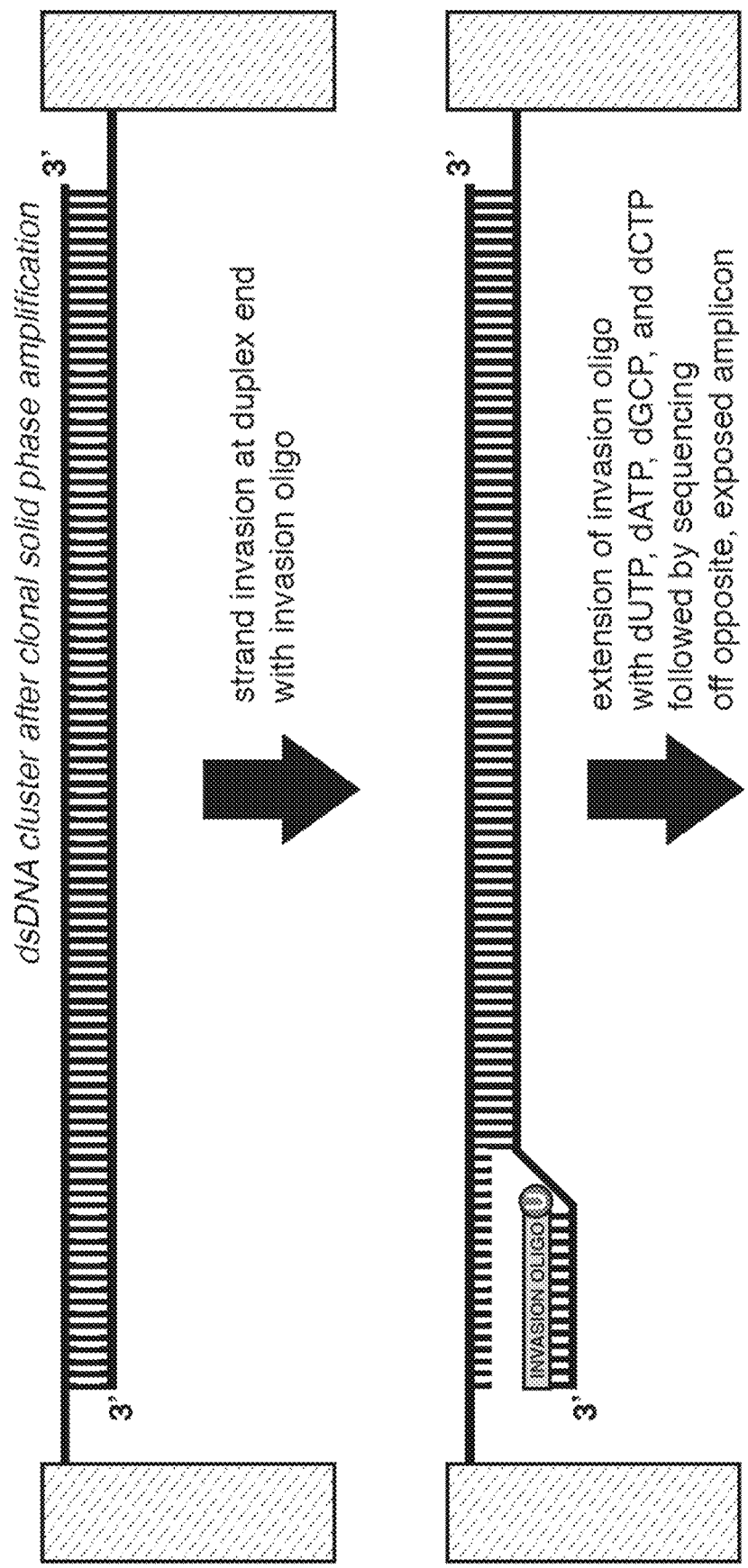
FIGS. 12A-12E illustrate an embodiment of paired-strand sequencing by strand invasion of an invasion primer at the 3' end of a first strand of a duplex, followed by runoff extension of the invasion primer by a strand-displacing polymerase.
Figure 12B:
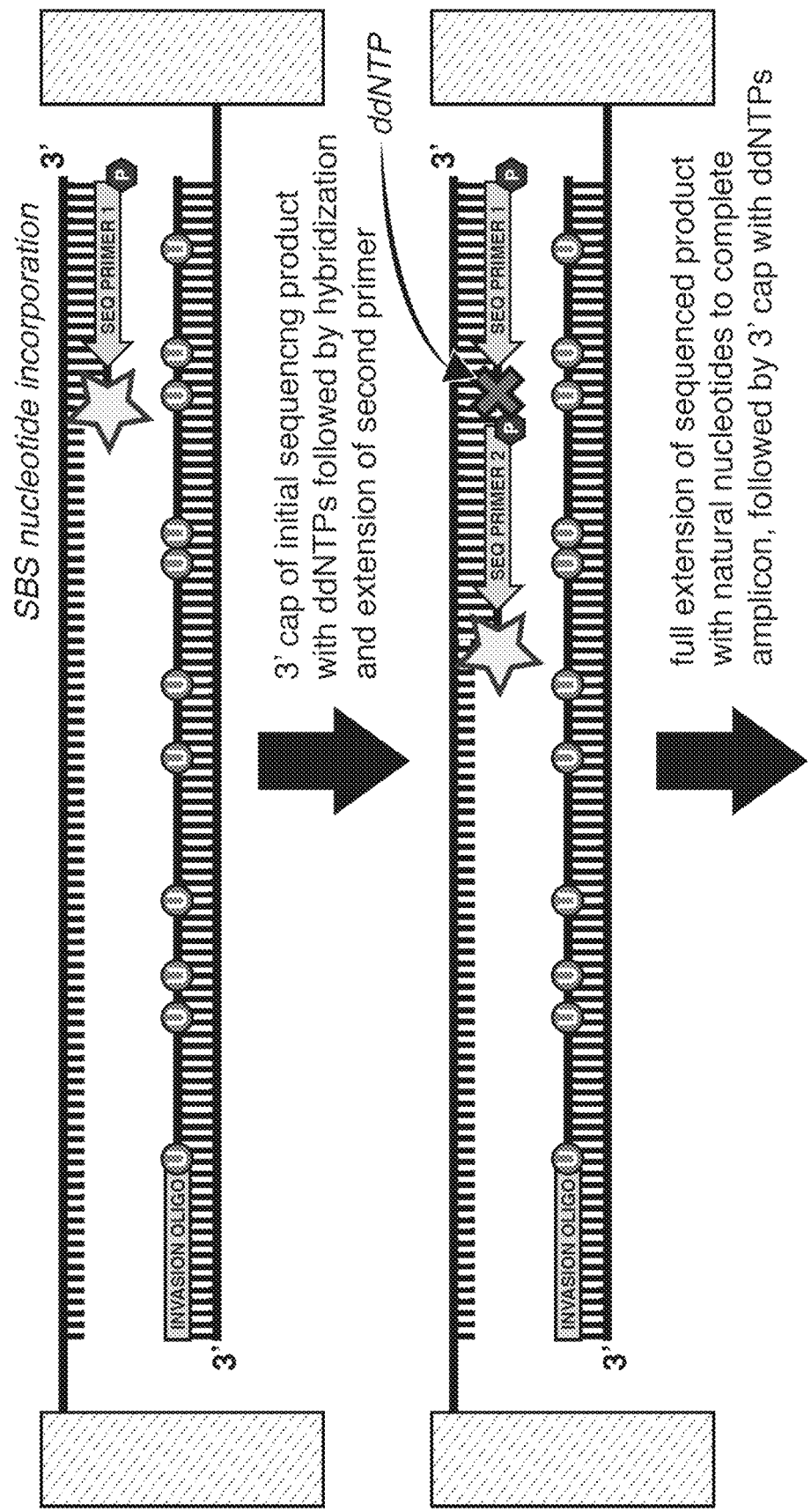
Figure 12C:
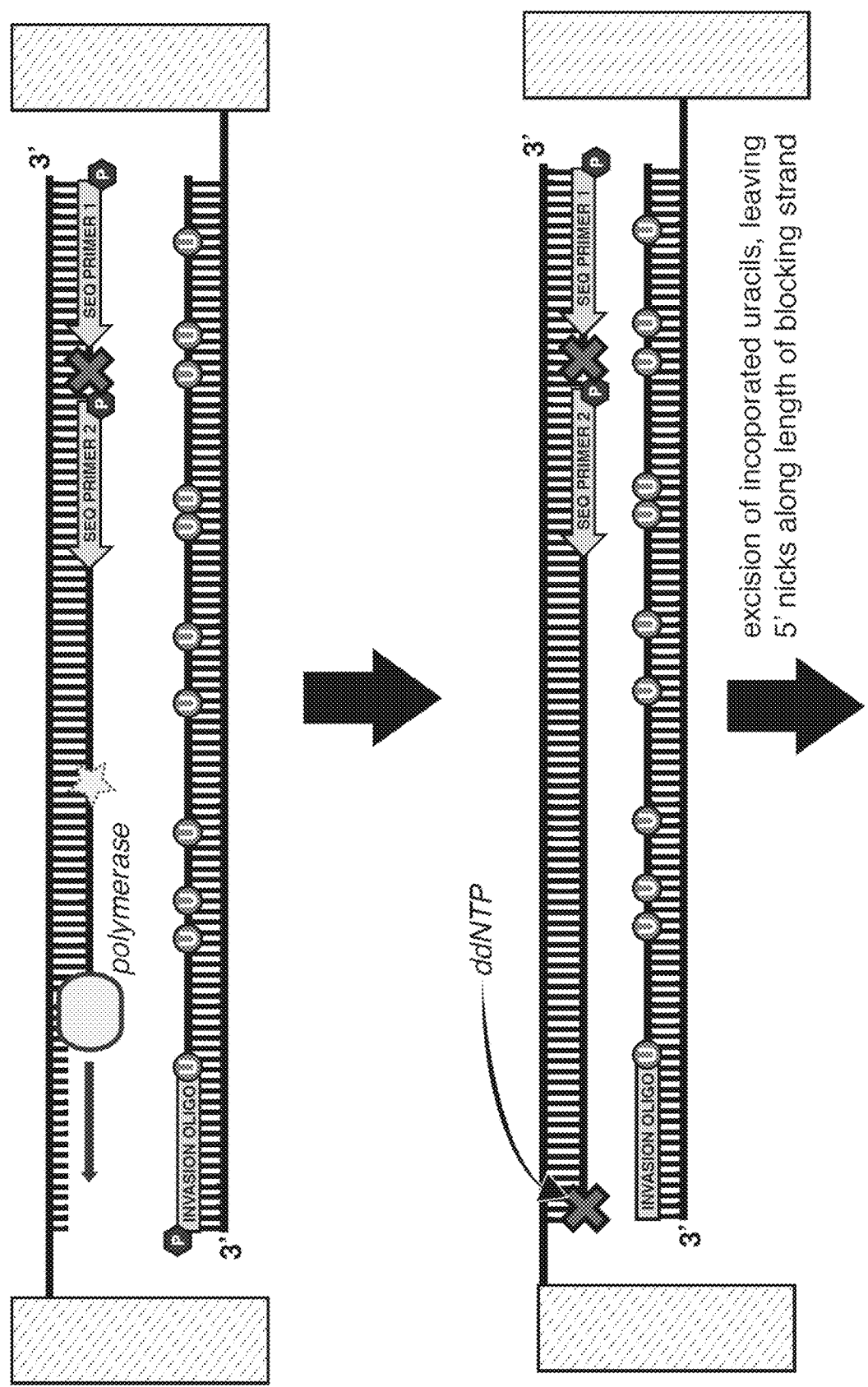
Figure 12D:
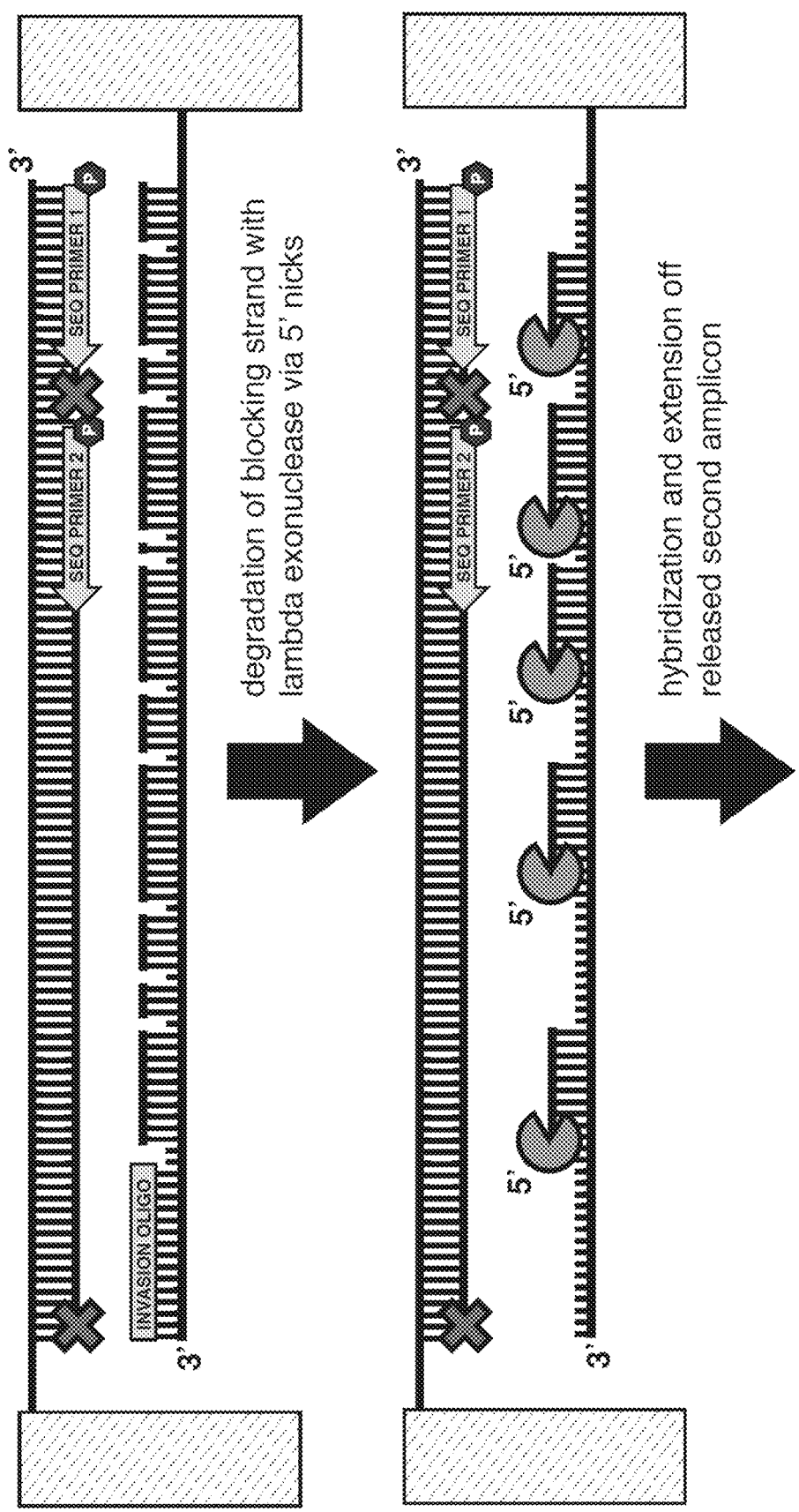
Figure 12E:
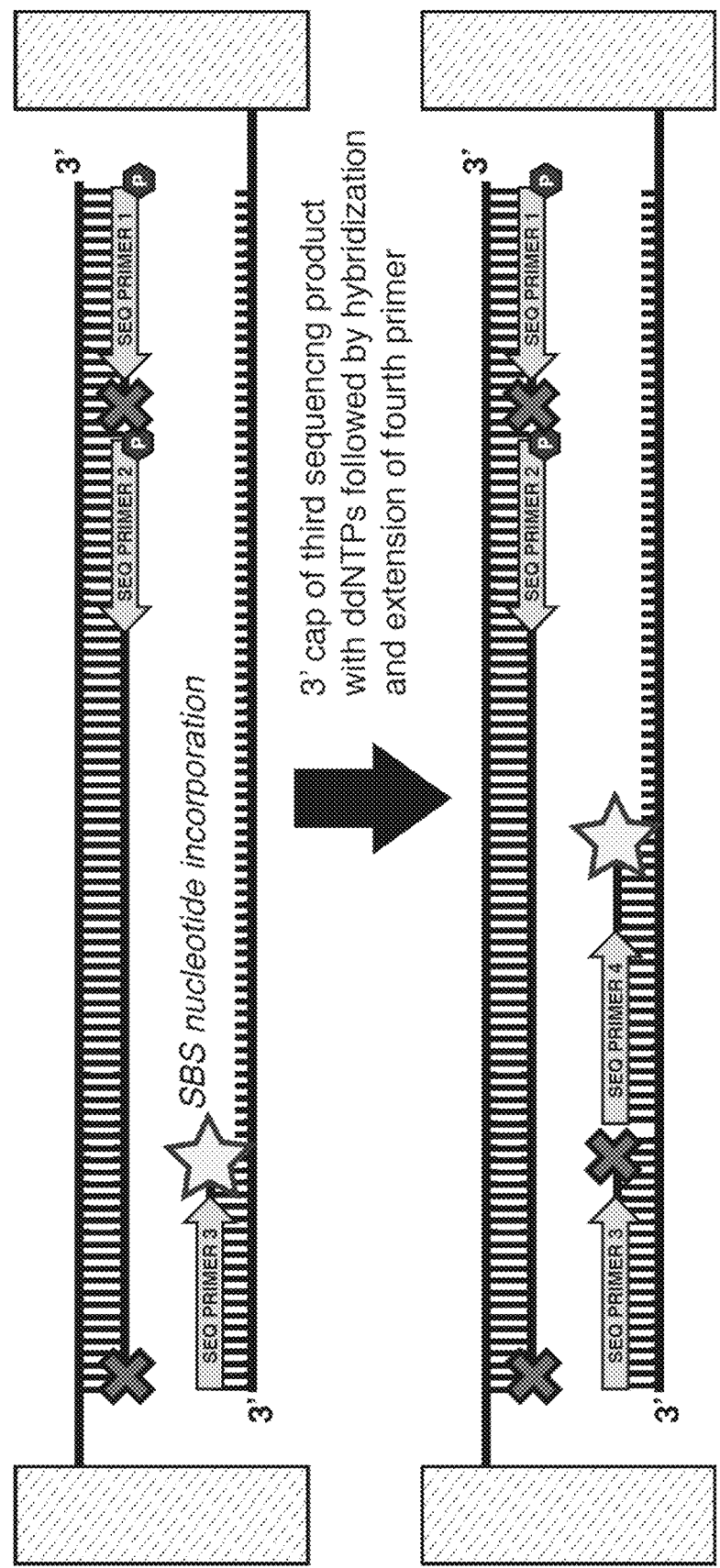

As an additional alternative to digesting away the invasion strand prior to sequencing the second strand, internal cleavable sites (e.g., cleavable internucleosidic bonds) may be introduced into the invasion strand. Following cleavage, the small products annealed to the second strand may then be digested away. As in the methods shown supra, FIG. 12A illustrates an invasion primer annealed to the 3' end of one of the strands. In embodiments, the invasion primer includes one or more phosphorothioate group(s) towards the 5' end to protect the invasion primer from 5' to 3' exonuclease digestion. In embodiments, the invasion primer also includes a cleavable site (also referred to herein as a scissile linkage). For example, as depicted as a 'U', the cleavable site may be a deoxyuracil (dU) towards the 3' end of the invasion oligo. Runoff extension of the invasion oligonucleotide is then performed with dUTP, dATP, dGTP, and dCTP, leaving one strand of the initial dsDNA molecule single-stranded and available for a first sequencing read, as shown in FIG. 12B. Once the first sequencing read has been obtained, the 3' end of the first sequencing read is capped by ddNTP incorporation. A second sequencing read is then obtained by annealing and extending a second sequencing primer 3' of the terminated first sequencing read. Subsequently, a ddNTP is incorporated into the 3' end of the second sequencing read, and thereafter the invasion strand may be nicked at internal scissile sites (e.g., resulting from amplification with the dUTP), leaving behind small fragments with exposed 5' ends that may be removed under suitable conditions, for example, by lambda exonuclease digestion, as shown in FIGS. 12C-12D. This cleavage and removal step exposes the 3' end of the second strand, making it available for a third sequencing read, as shown in FIG. 12E. Once the third sequencing read has been obtained, the 3' end of the third sequencing read is capped by ddNTP incorporation. A fourth sequencing read is then obtained by annealing and extending a fourth sequencing primer 3' of the terminated third sequencing read, as illustrated in FIG. 12E.

What is claimed is:

1. A method of sequencing a polynucleotide comprising a first strand hybridized to a second strand, wherein the first strand and second strand are both attached to a solid support, said method comprising:
  i) hybridizing an invasion primer to the second strand and extending the invasion primer with a polymerase, thereby generating an invasion strand and a single-stranded first strand, wherein the invasion primer is not covalently attached to the solid support;
  ii) hybridizing a sequencing primer to the single-stranded first strand;
  iii) incorporating one or more nucleotides into the sequencing primer with a polymerase to create an extension strand; and
  iv) detecting the one or more incorporated nucleotides so as to identify each incorporated nucleotide in said extension strand, thereby sequencing the first strand of the polynucleotide.

2. The method of claim 1, further comprising removing the first strand, removing the invasion strand, or both removing the first strand and removing the invasion strand.

3. The method of claim 1, further comprising removing the invasion strand and hybridizing a second invasion primer to the first strand and extending the second invasion primer with a polymerase, thereby generating a second invasion strand and a single-stranded second strand, wherein the second invasion primer is not covalently attached to the solid support.

4. The method of claim 1, further comprising nicking the invasion strand at a cleavable site to generate a 3' end and incorporating one or more nucleotides into the 3' end of the nicked invasion strand with a polymerase to create a second extension strand; and detecting the one or more incorporated nucleotides so as to identify each incorporated nucleotide in said second extension strand.

5. The method of claim 2, wherein removing the invasion strand comprises digesting the invasion strand using an exonuclease enzyme.

6. The method of claim 1, wherein the first strand is covalently attached to the solid support via a first linker and the second strand is covalently attached to the solid support via a second linker.

7. The method of claim 1, wherein the polynucleotide comprise known adapter sequences on the 5' and 3' ends.

8. The method of claim 1, wherein the solid support comprises a plurality of polynucleotides, wherein each polynucleotide is attached to the solid support at a 5' end of the polynucleotide.

9. The method of claim 1, wherein the invasion primer comprises locked nucleic acids (LNAs), Bis-locked nucleic acids (bisLNAs), twisted intercalating nucleic acids (TI-NAs), bridged nucleic acids (BNAs), 2'-O-methyl RNA: DNA chimeric nucleic acids, minor groove binder (MGB) nucleic acids, morpholino nucleic acids, C5-modified pyrimidine nucleic acids, peptide nucleic acids (PNAs), phosphorothioate nucleic acids, or combinations thereof.

10. The method of claim 1, wherein the invasion primer comprises one or more locked nucleic acids (LNAs), 2-amino-deoxyadenosine (2-amino-dA), trimethoxystilbene-functionalized oligonucleotides (TFOs), Pyrene-functionalized oligonucleotides (PFOs), peptide nucleic acids (PNAs), or aminoethyl-phenoxazine-dC (AP-dC) nucleic acids.

11. The method of claim 1, wherein the invasion primer is about 15 to about 35 nucleotides in length.

12. The method of claim 1, wherein the invasion primer comprises one or more locked nucleic acids (LNAs) at the 3' end of the invasion primer sequence.

13. The method of claim 1, further comprising contacting the invasion primer with a recombinase, a crowding agent, a loading factor, a single-stranded binding (SSB) protein, or a combination thereof.

14. The method of claim 1, wherein generating the invasion strand comprises contacting the polynucleotide with one or more invasion-reaction mixtures.

15. The method of claim 14, wherein each of the plurality of invasion-reaction mixtures comprise a plurality of invasion primers, a plurality of deoxyribonucleotide triphosphate (dNTPs), a polymerase, or a combination thereof.

16. The method of claim 14, wherein each of the plurality of invasion-reaction mixtures comprise a denaturant, single-stranded DNA binding protein (SSB), or both a denaturant and single-stranded DNA binding protein (SSB).

17. The method of claim 1, wherein generating the invasion strand comprises a first plurality of invasion-primer extension cycles followed by a second plurality of invasion-primer extension cycles, wherein the reaction conditions for the first plurality of invasion-primer extension cycles are different than the second plurality of invasion-primer extension cycles.

18. The method of claim 17, wherein the first plurality of invasion-primer extension cycles comprises incubation in a first denaturant and the second plurality of invasion-primer extension cycles comprises incubation in a second denaturant, wherein each of the first and second denaturant comprises additives, and wherein the concentrations of the additives in the first denaturant is higher than the concentrations of the additives in the second denaturant.

19. The method of claim 1, wherein generating the invasion strand comprises contacting the polynucleotide with a buffered solution comprising dimethyl sulfoxide (DMSO), betaine, or a combination of dimethyl sulfoxide (DMSO) and betaine.

20. The method of claim 1, wherein prior to hybridizing the invasion primer the method comprises amplifying the polynucleotide with bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR, or combinations of said methods.

21. The method of claim 1, wherein sequencing comprises sequencing by synthesis, sequencing by binding, sequencing by ligation, or pyrosequencing.

22. The method of claim 1, further comprising terminating extension by incorporating one or more unmodified dNTPs or one or more ddNTPs into the 3' end of the extension strand.

23. The method of claim 1, further comprising removing said invasion strand; hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand.

24. The method of claim 1, comprising:
terminating extension by incorporating one or more unmodified dNTPs or one or more ddNTPs into the 3' end of the extension strand;
hybridizing a second sequencing primer to the second strand and incorporating one or more nucleotides into the second sequencing primer with a polymerase to create a second extension strand; and detecting the one or more incorporated nucleotides so as to identify each incorporated nucleotide in said second extension strand;
terminating extension by incorporating one or more unmodified dNTPs or one or more ddNTPs into the 3' end of the second extension strand;
removing the invasion strand;
hybridizing a third sequencing primer to the first strand and incorporating one or more nucleotides into the third sequencing primer with a polymerase to create a third extension strand;
and detecting the one or more incorporated nucleotides so as to identify each incorporated nucleotide in said third extension strand;
terminating extension by incorporating one or more unmodified dNTPs or one or more ddNTPs into the 3' end of the third extension strand; and
hybridizing a fourth sequencing primer to the first strand and incorporating one or more nucleotides into the fourth sequencing primer with a polymerase to create a fourth extension strand; and detecting the one or more incorporated nucleotides so as to identify each incorporated nucleotide in said fourth extension strand.

25. The method of claim 3, further comprising hybridizing a second sequencing primer to the single-stranded second strand and incorporating one or more nucleotides into the second sequencing primer with a polymerase to create a second extension strand; and detecting the one or more incorporated nucleotides so as to identify each incorporated nucleotide in said second extension strand.

26. The method of claim 1, further comprising removing the first strand by cleaving the first strand at a cleavable site, washing away the cleaved strand, and generating a second sequencing read by hybridizing one or more second sequencing primers to the second strand; and extending the one or more second sequencing primers.

27. The method of claim 1, wherein the solid support comprises a plurality of immobilized primers.

28. The method of claim 27, wherein prior to generating the first invasion strand, the method comprises removing immobilized primers that do not contain a first or a second strand.

29. The method of claim 1, wherein extending the invasion primer comprises incorporating one or more deoxyuracil nucleobases.

30. A method of sequencing a polynucleotide comprising a first strand hybridized to a second strand, wherein the first strand and second strand are both attached to a solid support, said method comprising:
i) hybridizing a first invasion primer to the second strand and extending the first invasion primer with a polymerase, thereby generating a first invasion strand and a single-stranded first strand, wherein the first invasion primer is not covalently attached to the solid support;
ii) hybridizing a first sequencing primer to the single-stranded first strand;
iii) incorporating one or more nucleotides into the sequencing primer with a polymerase to create a first extension strand;
iv) detecting the one or more incorporated nucleotides so as to identify each incorporated nucleotide in said first extension strand, thereby sequencing the first strand of the polynucleotide;
v) removing the first invasion strand and hybridizing a second invasion primer to the first strand and extending the second invasion primer with a polymerase, thereby generating a second invasion strand and a single-stranded second strand, wherein the second invasion primer is not covalently attached to the solid support;
vi) hybridizing a second sequencing primer to the single-stranded second strand;
vii) incorporating one or more nucleotides into the second sequencing primer with a polymerase to create a second extension strand; and
viii) detecting the one or more incorporated nucleotides so as to identify each incorporated nucleotide in said second extension strand, thereby sequencing the second strand of the polynucleotide.

* * * * *

SEQUENCE LISTING

```
<160> NUMBER OF SEQ ID NOS: 60

<210> SEQ ID NO 1
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 2,4,6,8,11,14, 19,24, 26,31,32,33 are LNA
      nucleotides

<400> SEQUENCE: 1
tttttctcca gcgagatgac cctcaccaac cac                                   33

<210> SEQ ID NO 2
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 4,6,8,11,14,19,24,26,29,31,32,33 are LNA
      nucleotides

<400> SEQUENCE: 2
tttttctcca gcgagatgac cctcaccaac cac                                   33

<210> SEQ ID NO 3
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 6,8,11,14,19,21,24,26,29,31,32,33 are LNA
      nucleotide
<220> FEATURE:
<221> NAME/KEY: misc_feature
<222> LOCATION: (33)..(33)
<223> OTHER INFORMATION: 6,8,11,14,19,21,24,26,29,31,32,33 are LNA
      nucleotides

<400> SEQUENCE: 3
tttttctcca gcgagatgac cctcaccaac cac                                   33

<210> SEQ ID NO 4
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 8,11,14,16,19,21,24,26,29,31,32,33 are LNA
      nucleotides
```

```
<400> SEQUENCE: 4
tttttctcca gcgagatgac cctcaccaac cac                                33

<210> SEQ ID NO 5
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 2,4,6,8,11,14,19,24,26,28,31,32,33 are LNA
      nucleotides

<400> SEQUENCE: 5
tttttctcca gcgagatgac cctcaccaac cac                                33

<210> SEQ ID NO 6
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 2,4,6,8,11,14,19,21,24,26,28,31,32,33 are LNA
      nucleotides

<400> SEQUENCE: 6
tttttctcca gcgagatgac cctcaccaac cac                                33

<210> SEQ ID NO 7
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 2,4,6,8,11,14,16,19,21,24,26,28,31,32,33 are
      LNA nucleotides

<400> SEQUENCE: 7
tttttctcca gcgagatgac cctcaccaac cac                                33

<210> SEQ ID NO 8
<211> LENGTH: 34
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(34)
<223> OTHER INFORMATION: 2,4,10,12,13,14,20,26,27,28,30,31 are LNA
      nucleotides

<400> SEQUENCE: 8
tttttcucca gcgagaugac ccucaccaac cacu                               34

<210> SEQ ID NO 9
<211> LENGTH: 33
<212> TYPE: DNA
<213> ORGANISM: Artificial Sequence
<220> FEATURE:
```

<223> OTHER INFORMATION: Synthetic Polynucleotide
<220> FEATURE:
<221> NAME/KEY: misc_feature
<222> LOCATION: (33)..(33)
<223> OTHER INFORMATION: 2,5,8,11,14,16,20,23,27 are LNA nucleotides

<400> SEQUENCE: 9
acactctttc cctacacgac gctcttccga tct                                33

<210> SEQ ID NO 10
<211> LENGTH: 34
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (34)..(34)
<223> OTHER INFORMATION: 2,4,6,8,11,14,19,24,26,31 are LNA nucleotides

<400> SEQUENCE: 10
gtgactggag ttcagacgtg tgctcttccg atct                               34

<210> SEQ ID NO 11
<211> LENGTH: 33
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(33)
<223> OTHER INFORMATION: 2,4,6,8,11,14,19,24,26,31,32,33 are LNA
      nucleotides

<400> SEQUENCE: 11
gtgactggag ttcagacgtg tgctcttccg atc                                33

<210> SEQ ID NO 12
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,16,18,23,24,25 are LNA nucleotides

<400> SEQUENCE: 12
cagcgagatg accctcacca accac                                         25

<210> SEQ ID NO 13
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,16,18,21,23,24,25 are LNA nucleotides

<400> SEQUENCE: 13
cagcgagatg accctcacca accac                                         25

<210> SEQ ID NO 14
<211> LENGTH: 25
<212> TYPE: DNA

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,13,16,18,21,23,24,25 are LNA
      nucleodtides

<400> SEQUENCE: 14
cagcgagatg accctcacca accac                                          25

<210> SEQ ID NO 15
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,8,11,13,16,18,21,23,24,25 are LNA
      nucleotides

<400> SEQUENCE: 15
cagcgagatg accctcacca accac                                          25

<210> SEQ ID NO 16
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,16,18,20,23,24,25 are LNA nucleotides

<400> SEQUENCE: 16
cagcgagatg accctcacca accac                                          25

<210> SEQ ID NO 17
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,13,16,18,20,23,24,25 are LNA nucleotides

<400> SEQUENCE: 17
cagcgagatg accctcacca accac                                          25

<210> SEQ ID NO 18
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,8,11,13,16,18,20,23,24,25 are LNA
      nucleotides

<400> SEQUENCE: 18
cagcgagatg accctcacca accac                                          25
```

```
<210> SEQ ID NO 19
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(26)
<223> OTHER INFORMATION: 2,4,5,6,12,18,19,20,22,23 are LNA nucleotides

<400> SEQUENCE: 19
cagcgagaug acccucacca accacu                                              26

<210> SEQ ID NO 20
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(26)
<223> OTHER INFORMATION: 1,4,7,9,13,16,20 are LNA nucleotides

<400> SEQUENCE: 20
ttccctacac gacgctcttc cgatct                                              26

<210> SEQ ID NO 21
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(26)
<223> OTHER INFORMATION: 3,6,11,16,18,23 are LNA nucleotides

<400> SEQUENCE: 21
agttcagacg tgtgctcttc cgatct                                              26

<210> SEQ ID NO 22
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 3,6,11,16,18,23,24,25 are LNA nucleotides

<400> SEQUENCE: 22
agttcagacg tgtgctcttc cgatc                                               25

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2,4,6,8,11,14 are LNA nucleotides

<400> SEQUENCE: 23
tttttctcca gcgagatg                                                       18
```

```
<210> SEQ ID NO 24
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 4,6,8,11,14 are LNA nucleotides

<400> SEQUENCE: 24
tttttctcca gcgagatg                                               18

<210> SEQ ID NO 25
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 6,8,11,14 are LNA nucleotides

<400> SEQUENCE: 25
tttttctcca gcgagatg                                               18

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 8,11,14,16 are LNA nucleotides

<400> SEQUENCE: 26
tttttctcca gcgagatg                                               18

<210> SEQ ID NO 27
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2,4,6,8,11,14 are LNA nucleotides

<400> SEQUENCE: 27
tttttctcca gcgagatg                                               18

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2,4,6,8,11,14 are LNA nucleotides

<400> SEQUENCE: 28
```
tttttctcca gcgagatg                                                  18

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2,4,6,8,11,14,16 are LNA nucleotides

<400> SEQUENCE: 29
tttttctcca gcgagatg                                                  18

<210> SEQ ID NO 30
<211> LENGTH: 18
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (18)..(18)
<223> OTHER INFORMATION: 2,4,10,12,13,14 are LNA nucleotides

<400> SEQUENCE: 30
tttttcucca gcgagaug                                                  18

<210> SEQ ID NO 31
<211> LENGTH: 16
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (16)..(16)
<223> OTHER INFORMATION: 2,5,8,11,14,16 are LNA nucleotides

<400> SEQUENCE: 31
acactctttc cctaca                                                    16

<210> SEQ ID NO 32
<211> LENGTH: 14
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (14)..(14)
<223> OTHER INFORMATION: 2,4,6,8,11,14 are LNA nucleotides

<400> SEQUENCE: 32
gtgactggag ttca                                                      14

<210> SEQ ID NO 33
<211> LENGTH: 14
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (14)..(14)
<223> OTHER INFORMATION: 2,4,6,8,11,14 are LNA nucleotides

<400> SEQUENCE: 33
gtgactggag ttca                                                    14

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 34
aatgatacgg cgaccaccg                                               19

<210> SEQ ID NO 35
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 35
caagcagaag acggcatacg agat                                         24

<210> SEQ ID NO 36
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 36
cggtggtcgc cgtatcatt                                               19

<210> SEQ ID NO 37
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 37
atctcgtatg ccgtcttctg cttg                                         24

<210> SEQ ID NO 38
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(32)
<223> OTHER INFORMATION: 1,3,5,7,10,13,18,23,25,30,31,32 are LNA
      nucleotides

<400> SEQUENCE: 38
ttttctccag cgagatgacc ctcaccaacc ac                                32

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (30)..(30)
<223> OTHER INFORMATION: 1,3,5,8,11,16,21,23,26,28,29,30 are LNA nucleotides

<400> SEQUENCE: 39
ttctccagcg agatgaccct caccaaccac                                              30

<210> SEQ ID NO 40
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (28)..(28)
<223> OTHER INFORMATION: 1,3,6,9,14,16,19,21,24,26,27,28 are LNA
      nucleotides

<400> SEQUENCE: 40
ctccagcgag atgaccctca ccaaccac                                                28

<210> SEQ ID NO 41
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(26)
<223> OTHER INFORMATION: 1,4,7,9,12,14,17,19,22,24,25,26 are LNA
      nucleotides

<400> SEQUENCE: 41
ccagcgagat gaccctcacc aaccac                                                  26

<210> SEQ ID NO 42
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(32)
<223> OTHER INFORMATION: 1,3,5,7,10,13,18,23,25,27,30,31,32 are LNA
      nucleotides

<400> SEQUENCE: 42
ttttctccag cgagatgacc ctcaccaacc ac                                           32

<210> SEQ ID NO 43
<211> LENGTH: 32
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (32)..(32)
<223> OTHER INFORMATION: 1,3,5,7,10,13,18,20,23,25,27,30,31,32 are LNA
      nucleotides

<400> SEQUENCE: 43
ttttctccag cgagatgacc ctcaccaacc ac                                           32

<210> SEQ ID NO 44
<211> LENGTH: 32
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (32)..(32)
<223> OTHER INFORMATION: 1,3,5,7,10,13,15,18,20,23,25,27,30,31,32 are
      LNA nucleotides

<400> SEQUENCE: 44
ttttctccag cgagatgacc ctcaccaacc ac                                32

<210> SEQ ID NO 45
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 9,13,19 are LNA nucleotides

<400> SEQUENCE: 45
aatgatacgg cgaccaccg                                               19

<210> SEQ ID NO 46
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 3,6,12,18,19 are LNA nucleotides

<400> SEQUENCE: 46
aatgatacgg cgaccaccg                                               19

<210> SEQ ID NO 47
<211> LENGTH: 19
<212> TYPE: RNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 1,4,8,11,16,18 are LNA nucleotides

<400> SEQUENCE: 47
aaugauacgg cgaccaccg                                               19

<210> SEQ ID NO 48
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: 24 is LNA nucelotide

<400> SEQUENCE: 48
caagcagaag acggcatacg agat                                         24

<210> SEQ ID NO 49
<211> LENGTH: 24
```

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: 5,9,11,21 are LNA nucleotides

<400> SEQUENCE: 49
caagcagaag acggcatacg agat                                              24

<210> SEQ ID NO 50
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 4,10,18,19,20,23,25 are LNA nucleotides

<400> SEQUENCE: 50
tcaagcagaa gacggcatac gagat                                             25

<210> SEQ ID NO 51
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (26)..(26)
<223> OTHER INFORMATION: 2,5,6,14,24,25 are LNA nucelotides

<400> SEQUENCE: 51
ttcaagcaga agacggcaua cgagau                                            26

<210> SEQ ID NO 52
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 18,19 are LNA nucleotides

<400> SEQUENCE: 52
cggtggtcgc cgtatcatt                                                    19

<210> SEQ ID NO 53
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 2,5,12 are LNA nucelotides

<400> SEQUENCE: 53
cggtggucgc cgtaucauu                                                    19

<210> SEQ ID NO 54
```

```
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (22)..(22)
<223> OTHER INFORMATION: 3,8,11,21,22 are LNA nucleotides

<400> SEQUENCE: 54
tttcggtggt cgccgtatca tt                                              22

<210> SEQ ID NO 55
<211> LENGTH: 19
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (19)..(19)
<223> OTHER INFORMATION: 1,3,13,18 are LNA nucleotides

<400> SEQUENCE: 55
cggtggucgc cgtatcatt                                                  19

<210> SEQ ID NO 56
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: 2,5,8,13,17,24 are LNA nucleotides

<400> SEQUENCE: 56
atctcgtatg ccgtcttctg cttg                                            24

<210> SEQ ID NO 57
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: 4,23,24 are LNA nucleotides

<400> SEQUENCE: 57
atctcgtatg ccgtcttctg cttg                                            24

<210> SEQ ID NO 58
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (24)..(24)
<223> OTHER INFORMATION: 6,9,12,15,19,22,24 are LNA nucleotides

<400> SEQUENCE: 58
atctcgtatg ccgtcttctg cttg                                            24
```

```
<210> SEQ ID NO 59
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (25)..(25)
<223> OTHER INFORMATION: 4,12,25 are LNA nucleotides

<400> SEQUENCE: 59
atctcguaug ccgtctutcu gcuug                                          25

<210> SEQ ID NO 60
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 60
caagcagaag acggcatacg a                                              21
```